US011883580B2

(12) United States Patent
Dunne et al.

(10) Patent No.: US 11,883,580 B2
(45) Date of Patent: Jan. 30, 2024

(54) NEBULIZER AND CARTRIDGE

(71) Applicant: Boehringer Ingelheim International GmbH, Ingelheim am Rhein (DE)

(72) Inventors: Stephen Terence Dunne, Ipswich (GB); Joachim Carl Herbert Eicher, Ingelheim am Rhein (DE); Herbert Graessl, Murrhardt (DE); Andree Jung, Ingelheim am Rhein (DE); Gilbert Wuttke, Ingelheim am Rhein (DE)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 1200 days.

(21) Appl. No.: 16/470,298

(22) PCT Filed: Dec. 21, 2017

(86) PCT No.: PCT/EP2017/084137
§ 371 (c)(1),
(2) Date: Jun. 17, 2019

(87) PCT Pub. No.: WO2018/115306
PCT Pub. Date: Jun. 28, 2018

(65) Prior Publication Data
US 2020/0009333 A1 Jan. 9, 2020

(30) Foreign Application Priority Data
Dec. 21, 2016 (EP) .................................. 16020507

(51) Int. Cl.
*A61M 11/00* (2006.01)
*B05B 15/33* (2018.01)
(Continued)

(52) U.S. Cl.
CPC ...... *A61M 11/007* (2014.02); *A61M 15/0065* (2013.01); *B05B 11/0054* (2013.01);
(Continued)

(58) Field of Classification Search
CPC ............ A61M 11/007; A61M 15/0065; A61M 2205/123; A61M 2205/8281; B05B 15/33; B05B 11/0054
See application file for complete search history.

(56) References Cited

U.S. PATENT DOCUMENTS

| 4,083,476 A | 4/1978 | Schwartz et al. |
| 5,527,577 A | 6/1996 | Walters |

(Continued)

FOREIGN PATENT DOCUMENTS

| CA | 2481148 A1 | 10/2003 |
| CA | 2513167 A1 | 10/2004 |

(Continued)

OTHER PUBLICATIONS

International Search Report and Written Opinion for corresponding PCT Application No. PCT/EP2017/084137, 11 pages, dated Apr. 16, 2018.

(Continued)

*Primary Examiner* — Vishal Pancholi
*Assistant Examiner* — Robert K Nichols, II
(74) *Attorney, Agent, or Firm* — Matthew B. Dernier, Esq.

(57) ABSTRACT

A nebulizer for nebulizing a fluid from a cartridge and a cartridge for such a nebulizer is proposed. The cartridge comprises a container containing the fluid to be nebulized and is fluidically connected to the nebulizer by inserting a connecting element of the nebulizer for conveying the fluid out of the container. The cartridge is preferably adapted to sealingly receive the connecting element and can optionally (Continued)

comprise a membrane or sealing wall which seals the cartridge initially and is piercable or breakable by the connecting element upon insertion. The cartridge can further comprise an at least partially flexible and/or bendable tube for conveying the fluid out of the container. The tube is preferably wettable with the fluid and/or comprises an at least partially hydrophilic and/or polar surface. Further, the tube can at least partially be shaped as a helix. When the cartridge is connected to the nebulizer, the tube and the connecting element preferably form a continuous capillary and/or an at least essentially constant flow area.

57 Claims, 20 Drawing Sheets

(51) Int. Cl.
*A61M 15/00* (2006.01)
*B05B 11/00* (2023.01)

(52) U.S. Cl.
CPC ....... *B05B 15/33* (2018.02); *A61M 2205/123* (2013.01); *A61M 2205/8281* (2013.01)

(56) References Cited

U.S. PATENT DOCUMENTS

| | | | | |
|---|---|---|---|---|
| 5,782,345 | A * | 7/1998 | Guasch | B65D 51/285 206/219 |
| 5,833,088 | A | 11/1998 | Kladders | |
| 5,964,416 | A | 10/1999 | Jaeger | |
| 6,988,496 | B1 | 1/2006 | Eicher | |
| 7,325,706 | B2 | 2/2008 | Sweeton | |
| 7,351,386 | B2 | 4/2008 | Halstead | |
| 7,819,342 | B2 | 10/2010 | Spallek | |
| 7,950,388 | B2 * | 5/2011 | Kunze | B05B 11/0054 128/200.22 |
| 8,950,393 | B2 | 2/2015 | Holakovsky | |
| 9,757,750 | B2 | 9/2017 | Holakovsky | |
| 2003/0080210 | A1 | 5/2003 | Jaeger | |
| 2003/0190257 | A1 | 10/2003 | Halstead | |
| 2004/0031485 | A1 * | 2/2004 | Rustad | A61M 11/002 128/200.14 |
| 2005/0189380 | A1 | 9/2005 | Sweeton | |
| 2005/0263618 | A1 | 12/2005 | Spallek | |
| 2006/0016449 | A1 | 1/2006 | Eicher | |
| 2012/0174919 | A1 | 7/2012 | Hausmann | |
| 2012/0260913 | A1 | 10/2012 | Bach | |
| 2012/0325204 | A1 | 12/2012 | Holakovsky | |
| 2013/0056888 | A1 | 3/2013 | Holakovsky | |
| 2013/0327327 | A1 | 12/2013 | Edwards | |
| 2015/0203993 | A1 | 7/2015 | Tu | |
| 2016/0331863 | A1 | 11/2016 | Cawthon | |

FOREIGN PATENT DOCUMENTS

| | | | |
|---|---|---|---|
| CA | 2948072 | A1 | 11/2015 |
| CN | 1198689 | A | 11/1998 |
| CN | 1984838 | A | 6/2007 |
| CN | 202532846 | U | 11/2012 |
| CN | 203235101 | U | 10/2013 |
| CN | 103582505 | A | 2/2014 |
| CN | 203578085 | U | 5/2014 |
| CN | 104790054 | A | 7/2015 |
| CN | 105944176 | A | 9/2016 |
| CN | 205626639 | U | 10/2016 |
| DE | 4107301 | | 9/1992 |
| DE | 10300983 | A1 | 7/2004 |
| DE | 10347466 | A1 | 5/2005 |
| EP | 2614848 | A1 | 7/2013 |
| FR | 2101505 | | 3/1972 |
| FR | 2101505 | A1 | 3/1972 |
| FR | 2700483 | A1 | 7/1994 |
| IN | 204972564 | U | 1/2016 |
| JP | 0840473 | A | 2/1996 |
| JP | 2005212864 | A | 8/2005 |
| KR | 20090021327 | A | 3/2009 |
| WO | 9606011 | A2 | 2/1996 |
| WO | 9846522 | A1 | 10/1998 |
| WO | 0049988 | A2 | 8/2000 |
| WO | 2005107837 | A1 | 11/2005 |
| WO | 2006136426 | A1 | 12/2006 |
| WO | 2009103510 | A1 | 8/2009 |
| WO | 2009115200 | A1 | 9/2009 |
| WO | 2009047173 | A1 | 10/2009 |
| WO | 2010094305 | A1 | 8/2010 |
| WO | 2012130757 | A1 | 10/2012 |
| WO | 2012162305 | A1 | 11/2012 |
| WO | 2014203451 | A1 | 12/2014 |

OTHER PUBLICATIONS

Shouwu Yu, "Modification Principle and Technology of Polymer" Intellectual Property Publishing House, 12 pages, May 31, 2015.

Demao Yue "Practical Manual of Printing Technology" Printing Equipment, Printing Industry Press, vol. 3, 8 pages, dated Apr. 30, 2010.

* cited by examiner

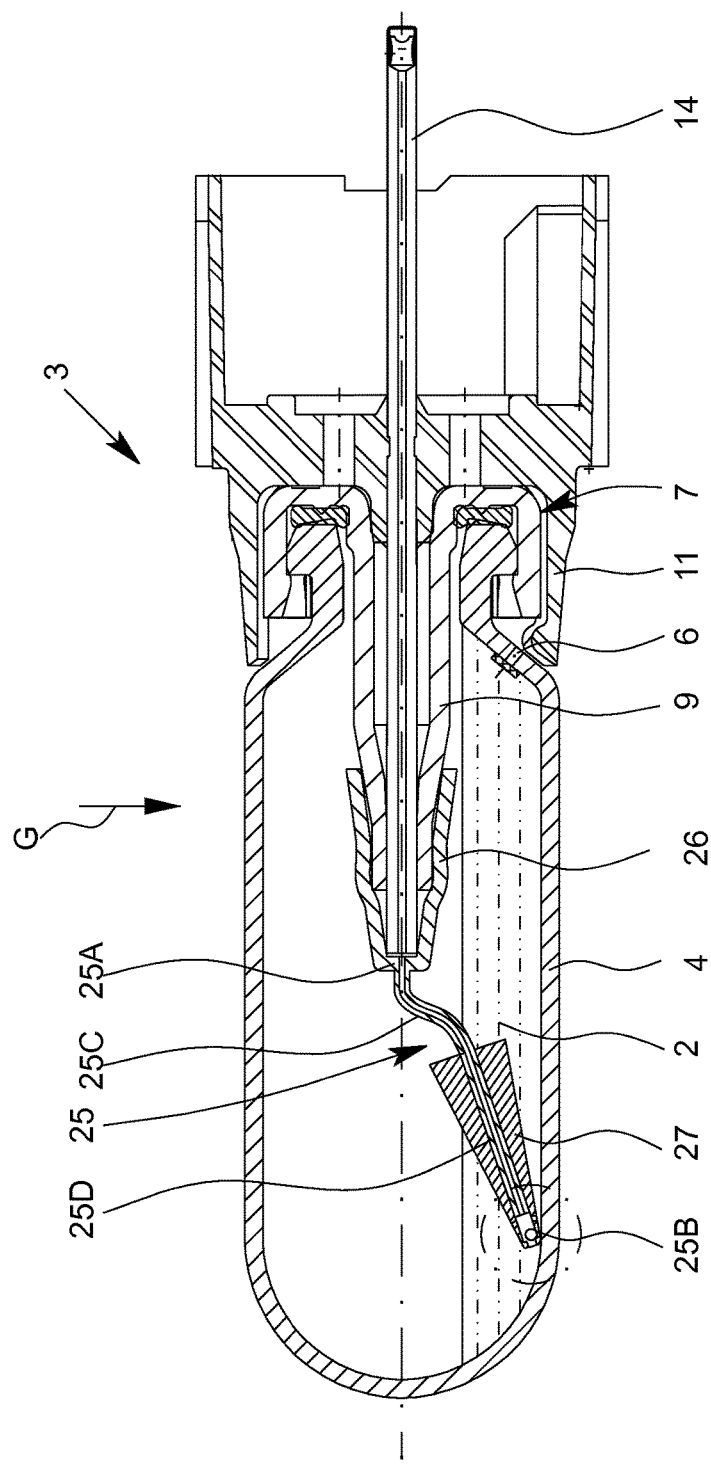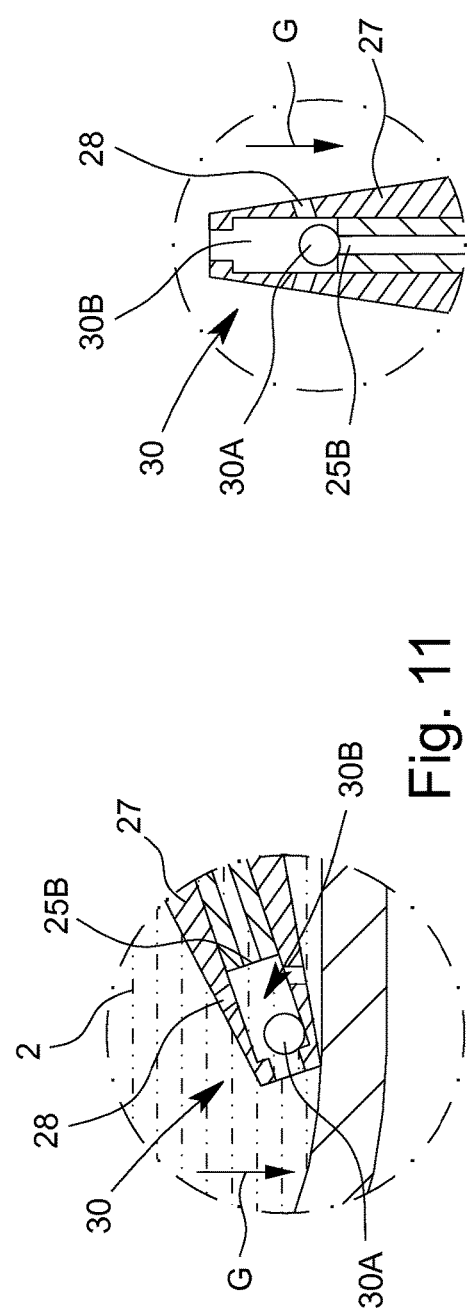

NEBULIZER AND CARTRIDGE

BACKGROUND

The present invention relates to a cartridge for a nebulizer according to the preamble of claim 1 or 30 and to a nebulizer according to the preamble of claim 54.

WO 2009/047173 A2 discloses a nebulizer for nebulizing a fluid. The nebulizer comprises an insertable cartridge containing the fluid, a housing for receiving the cartridge and a pressure generator with a drive spring in order to pressurize a dose of the fluid to be nebulized. The nebulizer further comprises a conveying tube that can be inserted into the cartridge and, when the drive spring is tensioned, withdraws a dose of the fluid out of the cartridge.

WO 2009/103510 A1 discloses a nebulizer including a pre-inserted cartridge that contains a fluid to be nebulized. The cartridge comprises a flexible conveying tube for conveying the fluid out of the cartridge.

WO 2010/094305 A1 discloses a nebulizer for dispensing a liquid, wherein the nebulizer comprises a cartridge with a storage containing the liquid and pressurized gas that pushes the liquid out of the storage through a valve in order to dispense the liquid.

WO 2012/130757 A1 relates to a hand-held device, in particular an atomizer, for discharging a liquid pharmaceutical preparation from a container having a container cap. The pharmaceutical preparation can, for example, be based on an alcoholic solvent. The atomizer having the inserted container comprises a sealing system composed of two seals at the connecting site between the device and the container which prevent loss of liquid, diffusion leaks and gas exchange with the surroundings at this site.

Depending on the spatial orientation of these nebulizers/cartridges withdrawal of the fluid can be affected. In particular, it might occur that not sufficient fluid can be withdrawn from the cartridge and/or that gas or air might be sucked out and/or that not the entire volume is used such that a residual amount of fluid remains within the cartridge after the last delivery of a dose.

WO 98/46522 A1 discloses a cartridge with a fluid and a storage medium, such as a sponge. A rigid or flexible tube for withdrawal of the fluid ends in the storage medium, that might be attached firmly to the wall of the cartridge or swing freely together with the withdrawal tube. The storage medium constantly keeps a certain amount of the fluid, even when the end of the tube lies above the fluid level in the cartridge. In that way, the fluid can be withdrawn from the cartridge essentially independently from its spatial orientation. Nevertheless, a certain residual amount of the fluid will remain within the cartridge or the storage medium that cannot be withdrawn.

U.S. Pat. No. 5,527,577 A discloses a liquid dispenser with a flexible eduction tube for discharging a liquid product from a container with the tube comprising a combination of a flexible material with a dense filler material to provide a specific gravity greater than the liquid product for enabling an input aperture of the eduction tube to remain below the level of the liquid product when the container is tipped from a vertical orientation. In an alternative embodiment, the eduction tube comprises a layer with absorbent material which can absorb a small portion of the liquid product to reduce or eliminate the surface tension between the eduction tube and the liquid product, reducing the tendency for the eduction tube to float on the liquid.

DE 103 47 466 A1 and FR 2 700 483 A1 disclose liquid dispensers having a dispensing mechanism comprising a flexible eduction tube with a weight or ballast at its free end. When the liquid dispensers are hold upside down, the weight or ballast exerts a force on the tube due to gravity causing the tube to bend such that the free end remains immersed in the liquid.

SUMMARY

In the light of the above, it is an object of the present invention to provide an improved nebulizer comprising a cartridge and/or an improved cartridge for a nebulizer, preferably wherein withdrawal/suction of a fluid contained in the cartridge is facilitated and/or can be carried out at least essentially independently from the spatial orientation of the nebulizer/cartridge and/or wherein the amount of fluid that can be withdrawn from the cartridge is increased and/or flow losses are reduced.

The present invention relates to a nebulizer/dispensing device for nebulizing/dispensing of a fluid, preferably a liquid, in particular a liquid pharmaceutical composition/formulation and/or liquid medicament, from a preferably replaceable cartridge containing the fluid, and further relates to the cartridge of such a nebulizer/dispensing device.

The fluid is preferably polar and/or comprises an electric dipole moment.

Mostly preferred, the fluid is aqueous and/or comprises an aqueous solution and/or water as solvent.

Alternatively, the fluid comprises an alcoholic solution and/or an alcohol, in particular ethanol, as solvent.

The cartridge comprises preferably a container and/or a bag containing the fluid, in particular multiple doses of the fluid, to be nebulized/dispensed.

Preferably, the cartridge comprises a tube, in particular a dip/conveying tube, particularly preferred a capillary tube, for conveying/withdrawal of the fluid out of the container, preferably wherein the tube is at least partially flexible or bendable.

According to one aspect of the present invention, the tube, in particular its inner and/or outer surface, is wettable with the fluid, preferably in such a way that—once in contact with the fluid—the tube, in particular at least its free end, gets wetted automatically with a film of the fluid and/or automatically takes up fluid and/or gets weighted down with the fluid and/or is aligned/bent automatically towards the fluid within the container and/or is at least partially immersed in fluid.

Preferably, the tube is wettable and constructed as a capillary tube, preferably with an inner diameter of less than 1 mm or less than 0.8 mm, in particular less than 0.7 mm or less than 0.5 mm, in particular such that—preferably in the delivery state of the cartridge and/or when opening the cartridge—the fluid level within the tube is equal to or above the fluid level outside the tube and/or such that—when the tube comes into contact with the fluid—the outer surface of the tube, in particular at least its free end, gets wetted and, further, the tube takes up/gets filled with the fluid due to the capillary action. Thus, in a synergistic manner the tube is wetted and/or weighted down on both its inner and outer surface with the fluid.

Preferably, the tube, in particular its inner and/or outer surface, is wettable with the fluid in such a way that the contact angle between a drop of the fluid and the surface of the tube is less than 70° or 60°, in particular less than 50° or 30°, mostly preferred less than 20°.

Preferably, the surface energy of the tube, in particular of its inner and/or outer surface, is greater than or equal to the surface tension of the fluid. Mostly preferred, the surface energy of the tube, in particular of its inner and/or outer surface, is at least 2 mN/m or 5 mN/m, in particular 8 mN/m or 10 mN/m, greater than the surface tension of the fluid. In this way, a good wetting of the tube can be achieved.

According to a preferred embodiment, the tube comprises an at least partially hydrophilic and/or polar surface, wherein the fluid is aqueous and/or comprises an aqueous solution and/or water as solvent, or wherein the fluid comprises an alcoholic solution and/or alcohol, such as ethanol, as solvent. In this way—when the tube comes into contact with the fluid—the fluid wets the tube extensively, in particular its hydrophilic and/or polar surface, with a film of the fluid.

Because of its wettability, the tube—once in contact with the fluid and wetted—gets weighted with the fluid and/or is aligned/bent automatically towards the fluid within the container, even if the fluid changes its position within the container, e.g. when the cartridge is turned in a horizontal position and/or upside down. This effect can be further increased by constructing the tube as a capillary tube and thereby automatically filling the tube with the fluid, as mentioned before.

Due to the (good) adhesion of the fluid to the tubes surfaces, i.e. the force causing the fluid to cling to the tubes surface, and/or due to the cohesion of the molecules of the fluid, i.e. the force causing the molecules of the fluid to cling to one another, at least the free end of the tube is kept in the fluid.

In particular, the adhesion forces and the cohesive forces are greater than the restoring force of the tube caused by bending, so that the tube will not reset into its rest position but rather remains immersed in the fluid, even when changing the spatial orientation of the cartridge. With other words, the tube or at least its axial end automatically moves together with the fluid within the cartridge and/or constantly keeps contact with the fluid. This allows the withdrawal of the fluid at least essentially independently from the spatial orientation of the cartridge.

Thus, the present invention allows withdrawal of the fluid and/or tensioning and/or actuating of the nebulizer at least essentially independently from the spatial orientation of the cartridge. In particular, a patient, i.e. a user of the nebulizer, does not have to make sure, that the nebulizer is oriented in a certain spatial orientation, e.g. vertically, when tensioning and/or actuating the nebulizer. In this way, misuse or misapplication of the nebulizer can be prevented or at least the risk of such a misuse or misapplication can be reduced.

Preferably, immersion of the tube is such that the free end of the tube is (always) located at least essentially at or adjacent to the lowest point of the fluid within the fluid in the cartridge for any spatial orientation.

Due to the wettability and/or the capillary action, the volume that can be withdrawn from the cartridge and/or the period of use of the cartridge can be increased.

Existing cartridges are typically overfilled with the fluid to be nebulized in order to ensure the delivery of doses with a constant volume, at least for the planned total amount of applications. With the invention there is no need to significantly overfill the cartridge as almost the full capacity of a normally filled cartridge can be exploited.

Wettability is preferably the ability of a material/surface, in particular a solid surface, to get wetted and/or to maintain contact with a fluid, in particular a liquid. It depends on the type of fluid and the type of material/surface used. In particular, the wettability depends on the surface tension of the fluid, the surface energy of the material/surface and the surface tension between the fluid and the surface (interfacial energy). The wettability of a material/surface can be quantified by the contact angle, i.e. the angle formed between a drop of the fluid and the (solid) surface/material in question.

The wettability/surface energy of a material/surface is preferably measured according to DIN 55660-2:2011-12.

Preferably, a material/surface is considered as wettable with a fluid if the contact angle is less than 90°, in particular less than 70°, and/or if the surface energy of the material/surface is—in particular at least 2 mN/m or 5 mN/m—greater than or equal to the surface tension of the fluid.

The contact angle is preferably the angle that is formed between a drop of the fluid on the surface of a material, i.e. its tangent at the contact point, and the surface of the material. The contact angle depends on the surface tension of the fluid, the surface energy of the material/surface and the surface tension between the fluid and the material/surface (interfacial energy). The contact angle is a measure for the wettability of a surface/material. A small contact angle, e.g. smaller than 70°, corresponds to a high wettability and a large contact angle, e.g. greater than 70° or 90°, corresponds to a low wettability or unwettability/non-wetting, commonly known as pearling effect or lotus effect.

The contact angle Θ can be defined as (Young's Equation):

$$\cos(\Theta)=[\sigma_S-\sigma_{SF}]/\sigma_F,$$

wherein $\sigma_S$ is the surface energy of the (solid) material/surface, $\sigma_{SF}$ is the surface tension between the fluid and the material/surface (interfacial energy) and $\sigma_F$ is the surface tension of the fluid, measured in [N/m].

The contact angle is preferably measured according to DIN 55660-2:2011-12 and/or according to ISO 15989:2004-12.

The surface tension of a fluid is caused by cohesion force of the fluid. The surface tension causes the fluid surface to acquire the least surface area possible. The surface tension of a fluid is preferably measured according to DIN 55660-3:2011-12.

The surface tension of a solid material, also referred to as surface energy, is a measure for the energy required to disrupt intermolecular bonds of the material. Materials with a high surface energy are more easily wettable than those with a low surface energy. The surface energy of a solid material is preferably measured according to DIN 55660-2:2011-12.

In particular, a surface can be (completely) wetted with a fluid if the surface energy of the surface is—preferably at least 2 mN/m or at least 5 mN/m—higher than the surface tension of the fluid.

In order to achieve the desired properties of the tube, i.e. to increase its surface energy and/or wettability, the tube is preferably surface treated, in particular corona, plasma, flame, wet chemical treated and/or (thin-film) coated. These surface treatment methods are well known to the person skilled in the art.

In addition or alternatively, the tube preferably contains at least one additive in order to increase its surface energy.

Preferably, the tube is made of rubber, in particular butyl rubber, and/or (flexible) plastic, in particular thermoplastics and/or thermoplastic elastomers, such as polyamide, polyethylene, polypropylene, polybutylene terephthalate, polyether block amide or the like. Typically, these (untreated) plastics comprise a surface energy between 27 mN/m and 45 mN/m and/or a contact angle with (distilled) water between 70° and 120°. Thus, depending on the fluid, this surface energy needs to be increased in order to achieve the desired wettability, preferably by surface treatment and/or (thin-film) coating.

Additionally or as an alternative, the fluid contains at least on additive, such as benzalkonium chloride, in order to decrease its surface energy.

Optionally, the cartridge might be equipped with an immersion/contact element, such as a weight, an anchor, a sponge or the like, that is attached to the tube, in particular to its free end, preferably such that at least the free end of the tube is kept in the fluid and/or pulled down by gravity. This ensures in addition that the tube, at least its free end or tip, stays in contact with the fluid within the container, even if the position of the container is changed. However, in particular when the nebulizer comprises movable components, e.g. for the tensioning process and/or during the nebulizing process, size and/or weight of the immersion/contact element need to be dimensioned small/low in order to prevent foam formation within the container. The total weight of the tube should be as low as possible to prevent or reduce foam formation.

Alternatively or additionally the immersion element can also be arranged such that it is located around a (end) portion of the tube and/or encompasses or covers a (end) portion of the tube.

Preferably, the density of the immersion element is chosen such that the immersion element is immersed in the fluid, but does not sink to the bottom of the container. In this way, the immersion element will not stick to the wall of the container and/or limit the movement of the tube.

Due to the capillary action within the tube and/or the construction of the tube as a capillary, the tube gets automatically filled with the fluid and thereby (further) weighted down.

Preferably, the tube is not only kept in the fluid by gravity, but rather/primarily by the wettability of the tube, as mentioned above. Nevertheless, both forces the gravitational force—increased by the capillary action and/or by the fluid sucked into the tube and/or by the immersion element—and adhesion force—increased by the wettability—interact in a synergistic manner and ensure that the tip of the tube remains immersed in the fluid, in particular at least essentially independently from its spatial orientation.

According to another aspect of the present invention, the container, in particular its inner surface, is less wettable with the fluid than the tube. In this way, less fluid sticks to the (inner) surface or layer of the container and the total amount of doses that can be dispensed is increased.

Preferably, the surface energy of the container, in particular its inner surface, is smaller than the surface energy of the tube and/or smaller than or equal to the surface tension of the fluid.

Preferably, the contact angle between the (inner) surface of the container and a drop of the fluid is greater than the contact angle between the surface of the tube and a drop of the fluid. Mostly preferred, the contact angle between the surface of the container and a drop of the fluid is greater than 70° or 90°.

When using an aqueous fluid and/or an aqueous solution and/or water as solvent, the container preferably is at least partially hydrophobic and/or comprises an at least partially hydrophobic and/or non-polar (inner) surface or layer.

The container or bag, in particular its (inner) surface or layer, might be coated with and/or be made of a material having a low surface energy, such as polytetrafluoroethylene (PTFE). In this way, the wettability of the container is decreased so that less fluid sticks to the (inner) surface or layer of the container or bag.

Thus, in a synergetic manner, a tube with a higher surface energy (compared to the surface energy of the container) and a container with a lower surface energy (compared to the surface energy of the tube) facilitate to increase the volume of fluid that can be withdrawn from the cartridge. Further, the tube will not stick to the container as no fluid film is formed between the tube and the container.

According to another aspect of the present invention, the tube has a minimum bend radius that is less than half, a quarter or a fifth of the inner diameter of the container, preferably wherein the tube is kink resistant when being bent until the minimum bent radius. This guarantees that the tube can be bent within the cartridge, preferably of at least 180°, without kinking and, thus, without affecting the withdrawal of the fluid. In this way, fluid can be withdrawn even when the spatial position of the nebulizer or the cartridge is changed, e.g. when the nebulizer/cartridge is turned upside down.

Optionally, the tube can further comprise a valve which is closed when immersion of the free end of the tube and/or immersion element in the fluid cannot be guaranteed, for example when the tube is not bent by at least 90°, 120°, 1500 or more in the upside down position, and/or when the valve or the free end of the tube is oriented upwardly. In this way it is prevented that air is sucked into the delivery mechanism of the nebulizer.

Preferably, the cartridge comprises a closure, in particular a preferably funnel- and/or cone-shaped connection port/adapter, for fluidically connecting the container to the nebulizer or a pump/pressure generator thereof.

The location of the closure on the cartridge preferably defines the top of the cartridge. In the following description, terms relating to positions and orientations, such as top, bottom, above, below, upright or the like, preferably refer to said location of the closure, even if the cartridge is in a different position/orientation.

Further, the axial direction is to be understood as the direction from closure or top of the container to the bottom of the cartridge or container. The radial direction is the direction perpendicular to said axial direction. In the case of an at least essentially cylindrical cartridge, the axial direction is the direction of the longitudinal axis of the cylinder and the radial direction is the direction of the radius of the cylinder.

The closure, in particular the connecting port, extends preferably into the interior of the container and/or holds or forms preferably an axially end of the tube in a center area of the container, preferably in such a way that the free end of the tube can reach the outermost areas of the container, in particular both the containers upper and lower axial end, i.e. its top and bottom. Due to this construction, the length of the tube and, thus, the risk of kinking can be decreased.

According to another aspect of the present invention, an at least partially flexible conveying/dip/capillary tube that is wettable with the fluid is used for withdrawal/conveying of a dose of a preferably polar fluid from a container for a nebulizer, preferably in such a way that—once in contact with the fluid—the tube, in particular at least its free end, gets wetted automatically with a film of the fluid and/or automatically takes up fluid and/or gets weighted down with the fluid and/or is aligned/bent automatically towards the fluid within the container. In this way, the advantages previously discussed can be achieved.

According to another aspect of the present invention, which can also be implemented independently, the tube has the shape of a helix. Preferably, said helix is a conical helix particularly preferably with its largest diameter at the free end of the tube and its smallest diameter at the fixed end of the tube and/or tapered towards the fixed end.

Preferably, the helix is compressible and/or stretchable and/or the axial length of the helix is adjustable, in particular such that the free end of the tube always remains immersed in the fluid. Preferably, the helix is adapted such that it automatically adjusts its length to the fluid or filling level. This advantageously prevents that the tube gets stuck at the inner wall of the container or bag.

The conical helix is preferably compressible to an at least essentially two-dimensional or flat spiral. In this way, the possibility that the helix or tube gets stuck with itself is preferably prevented or reduced. A further advantage is that handling of the tube is easier, for example during manufacturing.

Preferably, the helix is reversible when turned upside down. The term "reversible" preferably means that the direction of the longitudinal or axial extension of the helix is reversed. In the upright position, the helix preferably extends from the fixed end towards the bottom or lower axial end of the container or cartridge. In the upside down position, the extension is preferably reversed so that the helix extends from the fixed end towards the top or upper axial end or closure of the container or cartridge. In particular, the free end of the helix or tube points at least essentially towards the closure and/or is at least essentially the point of the helix or tube closest to the closure.

The proposed helical shape of the tube preferably ensures that the free end of the tube remains immersed in the fluid even when the cartridge is in an upside down position. In this way it is preferably ensured that it is always possible to withdraw fluid from the cartridge, in particular also in the upside down position. This can for example be advantageous in cases where a bendability of the tube by 180° cannot be realized, for example in a very slim cartridge with small inner diameter compared to its inner axial length.

The proposed nebulizer comprises a preferably insertable cartridge with a container containing a fluid to be nebulized and further comprises a housing for receiving the cartridge and a delivery mechanism for delivery/pressurizing the fluid.

According to another aspect of the present invention, which can also be implemented independently, the nebulizer comprises a preferably rigid connecting element, in particular constructed as a capillary, for fluidically connecting the cartridge to the delivery mechanism and a preferably flexible/bendable tube, in particular constructed as a capillary, for conveying the fluid out of the container, wherein the connecting element and the tube comprise or form a continuous capillary and/or a constant flow area, i.e. without an empty space, dead volume, gap and/or a capillary stop at the transition from the tube to the connecting element.

Any empty space or gap, also known as dead volume, at the transition from the tube to the connecting element lead to a widening of the flow area in that region. When fluid is conveyed from the tube, such dead volume at the transition needs first to be (completely) filled by fluid before further conveying of the fluid through the connecting element can continue. Thus, dead volume can lead to capillary stops, where conveying of the fluid slows down. It is therefore desirable to prevent such dead volume or at least keep it as small as possible to ensure a constant flow of fluid over the full length of the capillary.

Preferably, the (widest/largest) flow area at the transition from the tube to the connecting element is at least essentially equal to and/or not greater than 120% of the (smallest or largest) flow area of the connecting element and/or the tube.

In particular, the diameter of the (widest/largest) flow area at the transition from the tube to the connecting element is smaller than the outer diameter of the tube and/or connecting element.

In this way, flow losses at the transition from the tube to the connecting element are reduced. In particular, the formation of bubbles at the transition form the tube to the connecting element can be reduced and/or the capillary action can be used in both the tube and the connecting element without interruption.

According to another aspect of the present invention, which can also be implemented independently, the cartridge comprises a pierceable or breakable membrane or sealing wall. The membrane or sealing wall is preferably integrated or arranged within the closure, in particular the connection port. The membrane or sealing wall preferably seals the cartridge, in particular the container or fluid contained therein, from the environment in the delivery state, which is to be understood as the state of the cartridge before being connected to or inserted into the nebulizer.

The sealing wall is preferably adapted to be pierced or broken by the connecting element of the nebulizer when the cartridge is inserted into the nebulizer or connected to the delivery mechanism of the nebulizer. This advantageously prevents escaping of fluid from the cartridge and/or contamination of the fluid.

The membrane or sealing wall is preferably integrally formed or formed as one piece with the closure or connection port Particularly preferably, the membrane or sealing wall comprises a circumferential portion of reduced thickness and a film hinge, both the circumferential portion and the film hinge being integrally formed with the closure or connection port.

Preferably, when the connecting element is inserted in the connecting port, the membrane or sealing wall tears or breaks along the circumferential portion and tilts or hinges aside by means of the film hinge. In particular, also after breaking, the membrane or sealing wall remains connected to the closure or connection port via the film hinge. This ensures, that the membrane or sealing wall opens or breaks in a defined and reproducible manner without blocking or obstructing the tube, connecting element and/or delivery mechanism.

Preferably, the membrane or sealing wall further comprises a connecting portion of increased thickness, in particular formed by the film hinge, connecting the closure or connection port with the center of the membrane or sealing wall.

Particularly preferably, the closure or connecting port and the membrane or sealing wall are formed as one piece by injection-molding. In this case, the connecting portion or film hinge preferably forms a bridge or additional connection by which the molded material can get into the center of the sealing wall, thus forming the sealing wall, in particular without having to cross over the thin circumferential portion. This advantageously makes possible or simplifies the process of injection-molding the closure or connecting port with integrated membrane or sealing wall. This is conducive to a cost-effective manufacturing of the cartridge.

According to another aspect of the present invention, which can also be implemented independently, the cartridge is adapted to seal the connecting element, in particular radially. The closure, in particular the connection port, is preferably adapted to encompass or seal the connecting element in a liquid- and/or gas-tight manner. In particular, the closure or connection port can be stretchable or flexible, at least in part. When the preferably rigid connecting element is inserted into the cartridge, the closure or connection port preferably stretches apart and/or forms a press/tight-fit connection with the connecting element.

According to another aspect of the present invention, which can also be implemented independently, the cartridge comprises a sealing element between the closure or connection port and the container of the cartridge. The sealing element preferably seals off the container axially and/or radially. Such sealing is preferably realized by press/tight-fit of the sealing element between closure/connection port and container.

Preferably, the sealing element extends into the interior of the container and/or is adapted to sealingly receive the connecting element, in particular by press/tight-fit in a similar manner as described above for the connection port. In particular, the connecting element is sealingly received by the sealing element after passing through the connection port.

The sealing between connecting element and sealing element can be provided alternatively or additionally to the sealing between connecting element and connection port Particularly preferably, the connecting element is sealed or sealingly received by both the connection port and the sealing element. In this case, preferably first the sealing with the connection port is formed or established, and after passing of the connecting element or of its axial end through the connection port the sealing with the sealing element is formed or established.

The cartridge or closure can optionally comprise an adapter in particular for connecting the tube to the closure or connection port. Alternatively or additionally to the sealing(s) between the connecting element and the connection port and/or sealing element, a sealing can also be provided between the adapter and the connecting element, particularly preferably by press/tight-fit in the same manner as described above for the connection port. In a particularly preferred embodiment, the sealing element comprises, forms or forms part of the adapter or vice versa.

The aspects of the present invention mentioned above and in the following can be realized independently of one another and in any combination.

BRIEF DESCRIPTION OF THE DRAWING

Further advantages, features, characteristics and aspects of the present invention will become apparent from the claims and the following description of preferred embodiments with reference to the drawings.

FIG. 10 is a schematic section of a cartridge according to a third embodiment of the invention, connected to a partially shown nebulizer;

FIG. 11 is a schematic detail of the cartridge according to FIG. 10;

FIG. 12 is a further schematic detail of the cartridge according to the third embodiment;

DETAILED DESCRIPTION

Figure 1:
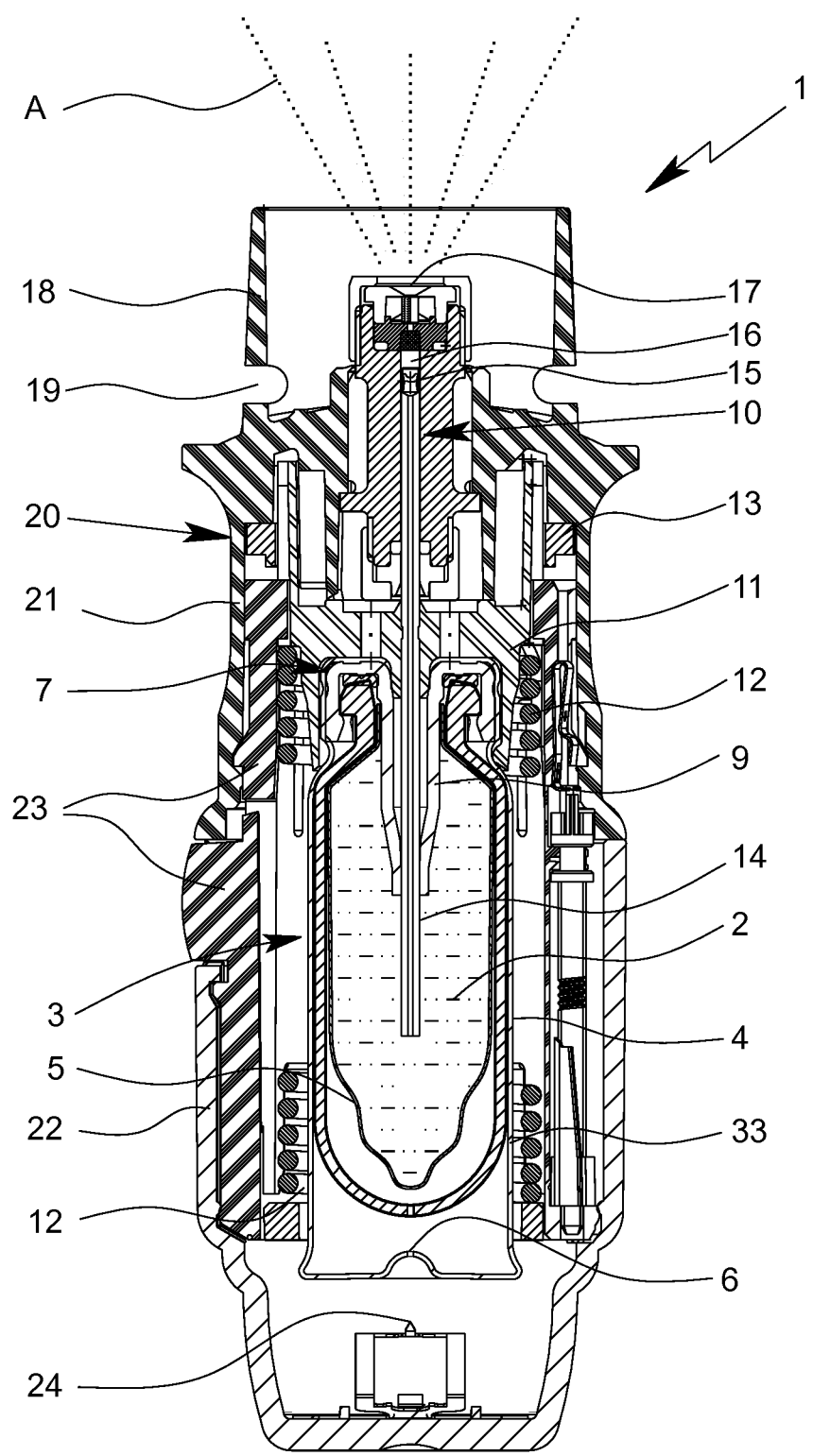
FIG. 1 is a schematic section of a known nebulizer in a non-tensioned state.

In the figures, the same reference numerals are used for identical or similar parts, preferably resulting in corresponding or comparable properties and advantages, even if the associated description is not repeated.

Figure 2:
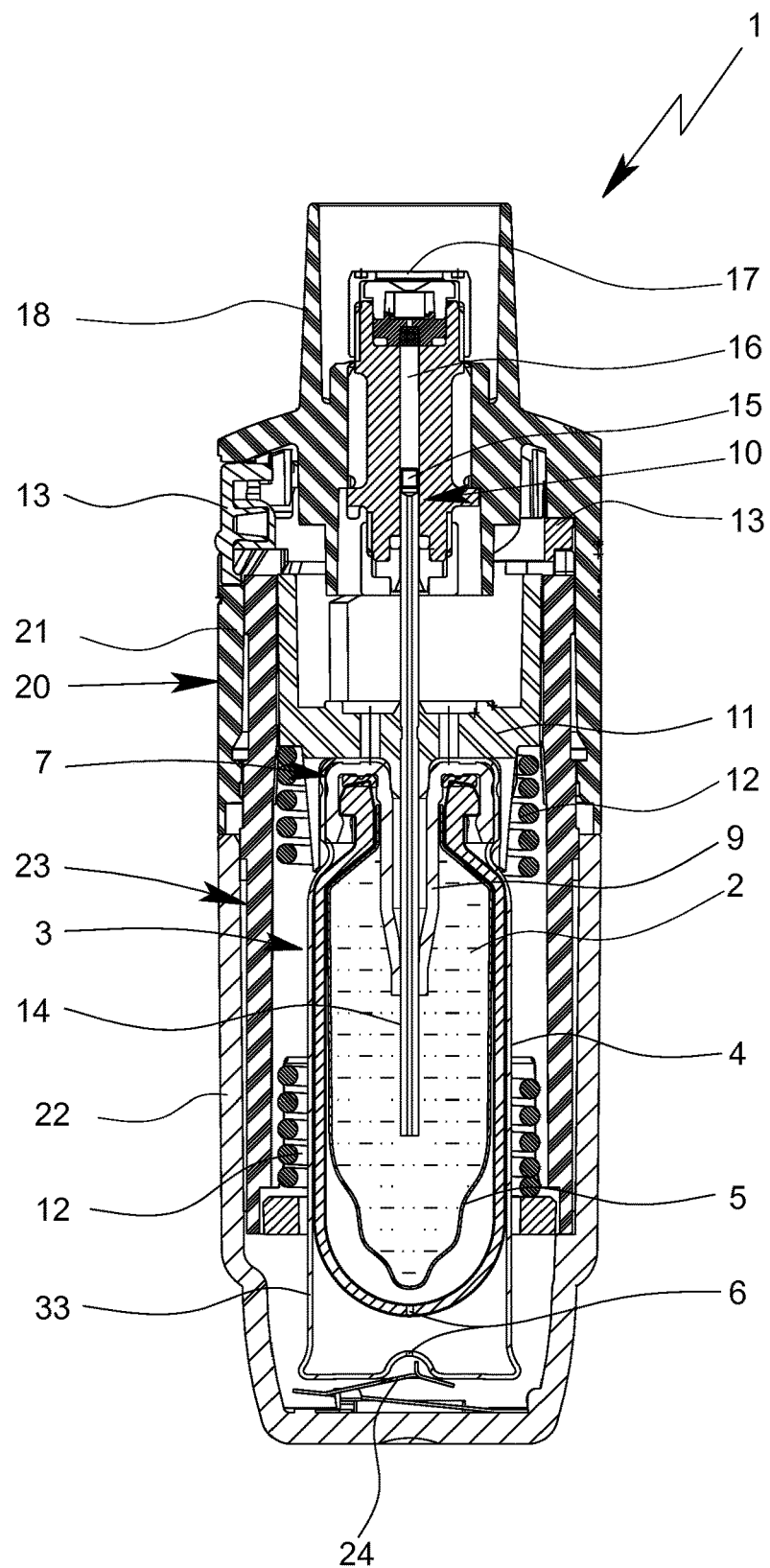
FIG. 2 is a schematic section, rotated by 90° compared to FIG. 1, of the known nebulizer in a tensioned state.

FIG. 1 and FIG. 2 show a known nebulizer/dispensing device 1 for atomizing/nebulizing/dispensing of a fluid 2, in particular a pharmaceutical composition, medicament or the like, schematically shown in a non-tensioned state (FIG. 1) and in a tensioned state (FIG. 2).

The fluid 2 is preferably polar and/or comprises an electric dipole moment. In particular, the fluid 2 is aqueous or alcoholic, and/or comprises an aqueous or alcoholic solution, and/or comprises water or an alcohol, in particular ethanol, as solvent.

The nebulizer 1 is preferably adapted to dispense and/or nebulize the fluid 2 or a dose thereof.

Preferably, when the fluid 2, preferably a liquid, more particularly a pharmaceutical component, is nebulized/dispensed, an aerosol A (as indicated by dashed lines in FIG. 1) is formed or dispensed, which can be breathed in or inhaled by a user (not shown).

Usually, the inhaling is done at least once a day, more particularly several times a day, preferably at set intervals, depending on the complaint or illness from which a patient is suffering.

The nebulizer 1 is constructed in particular as a portable inhaler and/or operates preferably only mechanically and/or without a propellant/gas. Nevertheless, other constructions are possible as well.

The nebulizer 1 is provided with or comprises or is adapted to receive an insertable or replaceable cartridge 3 containing the fluid 2. Thus, the cartridge 3 forms a reservoir for the fluid 2, which is to be nebulized/dispensed.

FIGS. 1 and 2 show a known nebulizer 1 with a schematically drawn cartridge 3, wherein FIG. 3 to 22 show a cartridge 3 or parts thereof according to the invention. Preferably, some features, characteristics and aspects described with regard to FIG. 1 and FIG. 2 can apply to the cartridge 3 described with regard to FIG. 3 to 22, i.e. the cartridge 3 according to FIG. 3 to 22 might comprise some features, characteristics and aspects of the cartridge 3 according to FIG. 1 and FIG. 2. In particular, the cartridge 3 described in connection with FIG. 3 to 22 might be used with the nebulizer 1 described in connection with FIG. 1 and FIG. 2.

In the following, the known cartridge 3 according to FIGS. 1 and 2 is described.

Preferably, the cartridge 3 contains multiple doses of the fluid 2, in particular sufficient to provide at least 100 or 150 and/or up to 200 or more dosage units or doses, i.e. to allow at least 100 and/or up to 200 sprays or applications.

Figure 23:
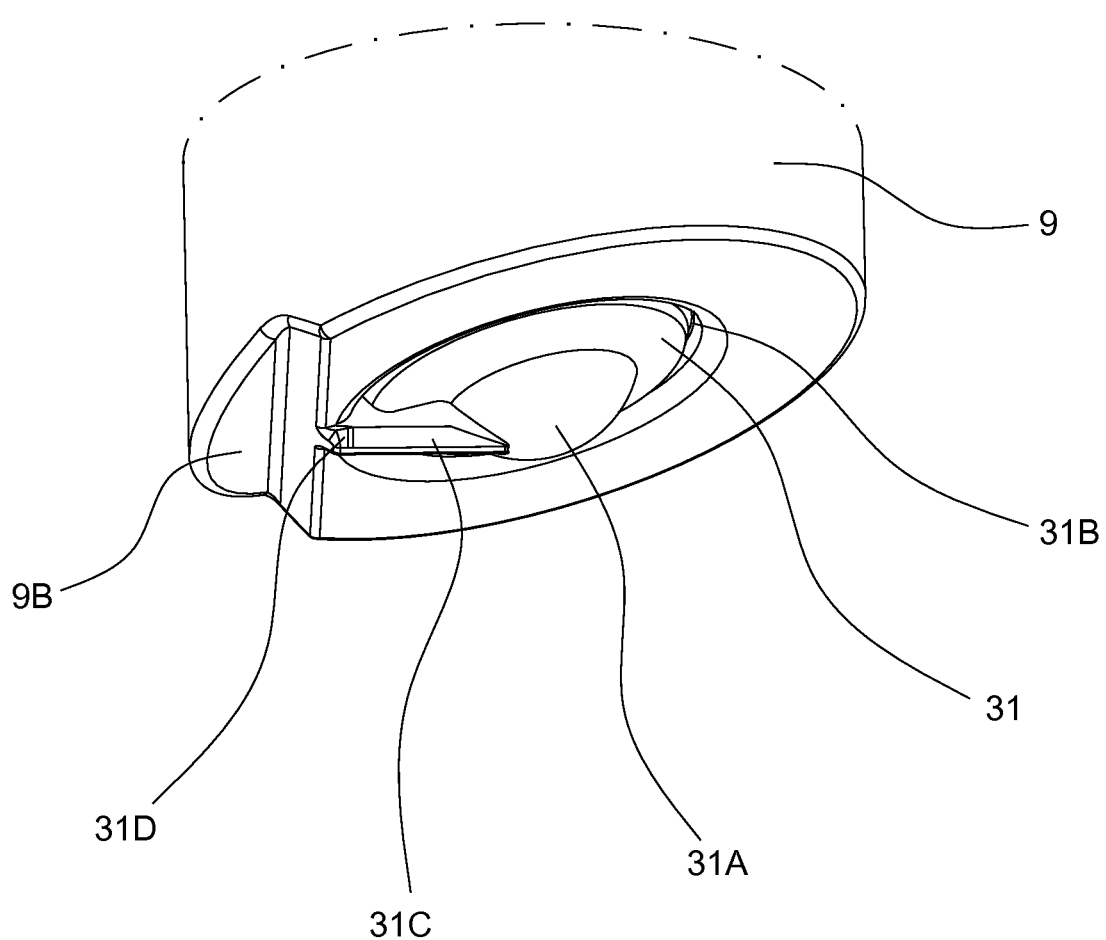
FIG. 23 is a perspective detail of the cartridge according to the seventh embodiment.

The cartridge 3 preferably holds a volume of about 0.5 ml to 30 ml, particularly preferably about 4 ml to 20 ml. Further, the number of doses contained in the cartridge 3 and/or the total volume of the fluid 2 contained in the cartridge 3 can vary depending on the fluid 2 or respective medicament and/or depending on the cartridge 3 and/or depending on necessary medication or the like.

Preferably, the nebulizer 1 is adapted to nebulize/dispense a dose of 1 μl to 80 μl of fluid 2, even more preferably a dose of 5 μl to 20 μl or alternatively of more than 20 μl, in particular of about 50 μl, within one actuation/use of the nebulizer 1 and/or within one spray/aerosol delivery/dispense.

Preferably, the cartridge 3 can be replaced or exchanged, in particular as disclosed in WO 2012/162305 A1. Preferably, the total number of uses of the nebulizer 1 and, thus, the number of cartridges 3, which can be used with the same nebulizer 1, is preferably restricted, e.g. to a total number of four, five or six cartridges 3. WO 2012/162305 A1 discloses such a restriction to the total number of cartridges 3 which can be used with the same nebulizer 1.

The cartridge 3, in particular the container 4, is preferably substantially cylindrical or cartridge-shaped and/or of rigid construction. Nevertheless, other constructional solutions are possible as well. In particular, the cartridge 3 or container 4 can be at least partially spherical.

Preferably, once the nebulizer 1 has been opened, the cartridge 3 can be inserted therein, preferably from below and changed if desired.

The cartridge 3 as known in combination with the known nebulizer 1 comprises a preferably rigid container 4 and/or an optional, preferably flexible/collapsible, bag 5 containing the fluid 2, preferably wherein the optional bag 5 is arranged or held within the container 4.

Optionally, the cartridge 3 can further comprise a housing 33 which is preferably rigid and/or made of metal, in particular aluminum. A particular embodiment of such a housing is described in further detail in connection with FIGS. 21 and 22 according to a seventh embodiment of the present invention.

Preferably, the cartridge 3 as known in combination with the known nebulizer 1 is constructed as described in WO 96/06011 A2 and/or WO 00/49988 A2.

Optionally, the cartridge 3, in particular the container 4, comprises a ventilation/aeration 6, e.g. a valve, opening or hole, for venting/aeration of the cartridge 3, in particular container 4, preferably in order to enable or support withdrawal of fluid 2 from the container 4.

Preferably, the ventilation 6 forms a direct or indirect gas connection between the interior of the container 4 and its surroundings and/or the ambient and/or allows a pressure compensation between the interior of the container 4 and its surroundings and/or the ambient.

When the ventilation 6 is open, air or any other gas can flow through the ventilation 6 into the container 4 so that pressure compensation between the interior of container 4 and its surrounding is possible or achieved. In particular, negative air pressure can be avoided or at least compensated when withdrawing the fluid 2 and/or collapsing optional bag 5.

FIGS. 1, 2 and 20 show an indirect gas connection, wherein FIGS. 3 to 6, FIG. 8, FIG. 10 and FIGS. 13 to 18 show a direct gas connection.

The indirect gas connection allows pressure compensation between the interior of the container 4 and its surroundings such that the bag 5 can be collapsed. The air that flows into the container 4 through the ventilation 6 does not come into direct contact with the fluid 2 contained in the bag 5.

In contrast to the indirect gas connection, the direct gas connection as shown in FIG. 3 to 6, FIG. 8, FIG. 10 and FIGS. 13 to 18 allows air to flow into the container 4 and come into direct contact with the fluid 2 contained in container 4.

At least for the direct gas connection, it is preferred that the ventilation 6 comprises a sterile filter such that the fluid 2 does not get contaminated by impurities or foreign substances of the air or any other gas. For the indirect gas connection, the gas does not come into direct contact with the fluid 2 and a sterile filter can be omitted. However, it is also possible to provide the ventilation 6 with a sterile filter for the indirect gas connection.

Preferably, the ventilation 6 opens automatically and/or before or during first use of nebulizer 1.

Alternatively, the cartridge 3, in particular container 4, is pressurized, e.g. with a propellant/gas, preferably with a pressure of more than 2 MPa or 3 MPa and/or less than 10 MPa or 8 MPa, in particular such that a ventilation/aeration can be omitted and/or that with each delivery of a dose of fluid 2 the pressure in cartridge 3 or container 4 decreases.

The cartridge 3 is preferably closed and/or sealed and/or comprises preferably a closure 7, preferably wherein the closure 7 is adapted to close and/or seal the container 4 and/or bag 5, in particular in a gas-tight and/or liquid-tight manner.

Optionally, ventilation 6 is integrated in the closure 7 and/or opened together with closure 7, as described in WO 2006/136426 A1, e.g. on page 9, line 20, to page 14, line 2.

In such an embodiment, the ventilation 6, such as a thin canal, is preferably opened/created by opening/piercing the closure 7, in particular wherein pressure compensation through the ventilation 6 takes places without fluid 2 leaking therethrough.

Preferably, the cartridge 3, in particular the closure 7, comprises a preferably pierceable seal 8 and/or a preferably flexible, in particular funnel- and/or cone-shaped, connection port/adapter 9.

The seal 8 is schematically shown in FIG. 3, in which the cartridge 3 according to a first embodiment of the invention is in a closed/unpierced state. The seal 8 is further shown schematically in FIG. 21 in a closed/unpierced state and in FIG. 22 in an open/pierced state according to a seventh embodiment of the present invention. FIG. 23 shows a detail of the seal 8 according to the seventh embodiment.

The seal 8 covers or seals preferably the container 4 and/or connection port 9, at least before the cartridge 3 is inserted into the nebulizer 1.

Preferably, the seal 8 can be embodied as a foil 8A and/or a membrane or sealing wall 31, in particular a diaphragm or septum, mostly preferred wherein the foil 8A covers the connection port 9 and/or the membrane or sealing wall 31 is integrated in and/or arranged within the connection port 9.

A preferred construction of the membrane or sealing wall 31 will be explained later in further detail in connection with FIGS. 21 to 23.

Figure 3:
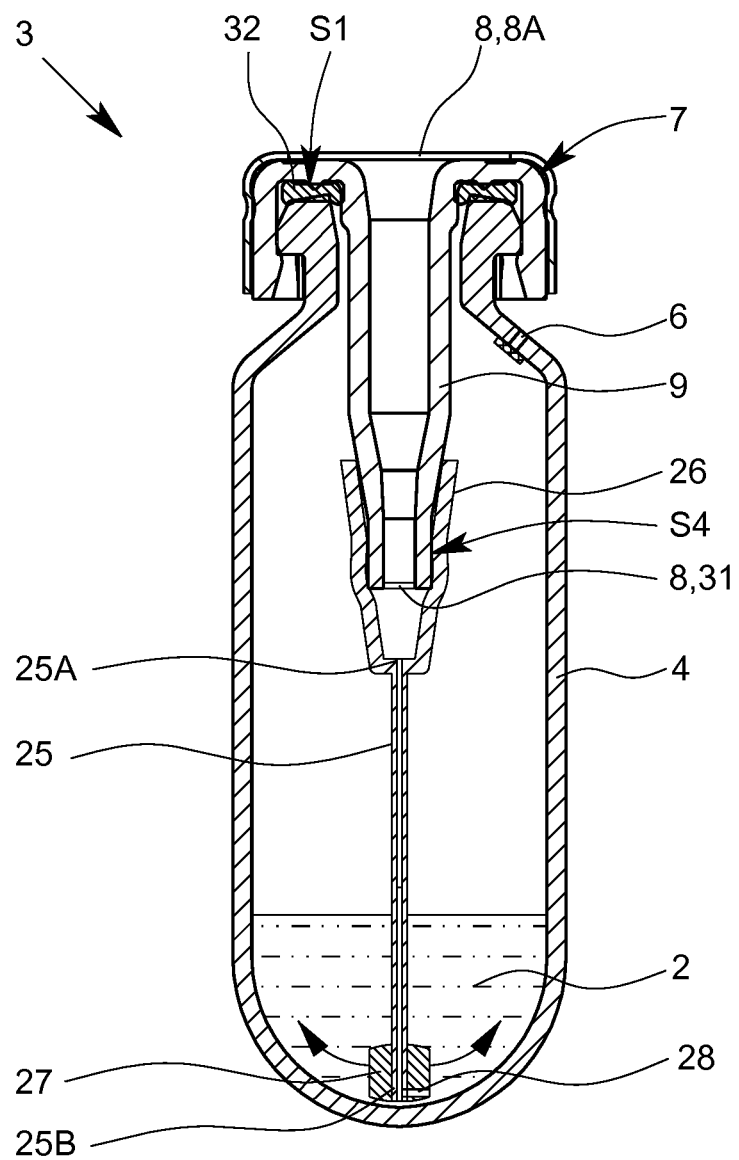
FIG. 3 is a schematic section of a cartridge according to a first embodiment of the invention.
Figure 21:
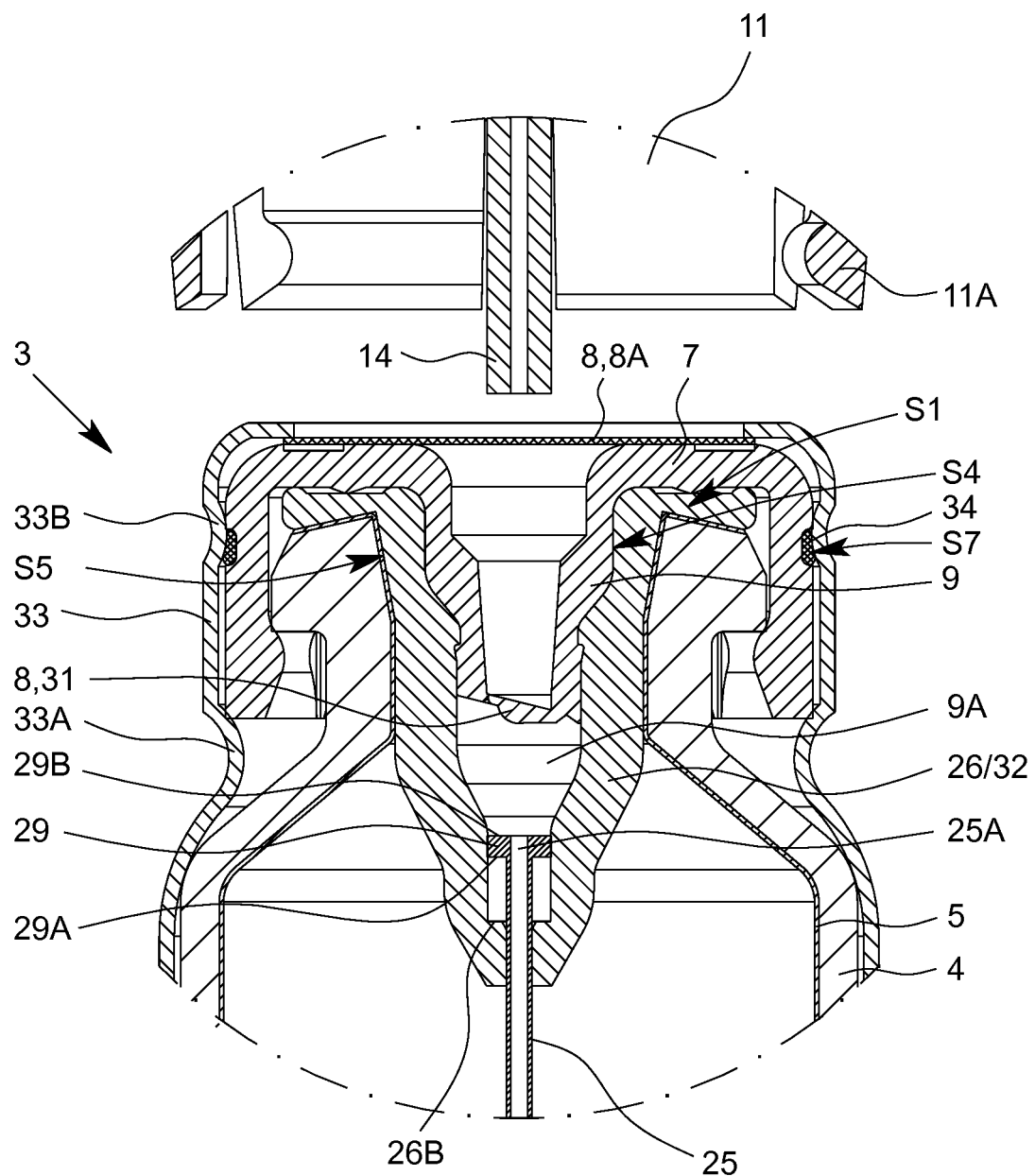
FIG. 21 is a schematic section of the cartridge with a closed membrane or sealing wall according to a seventh embodiment.
Figure 22:
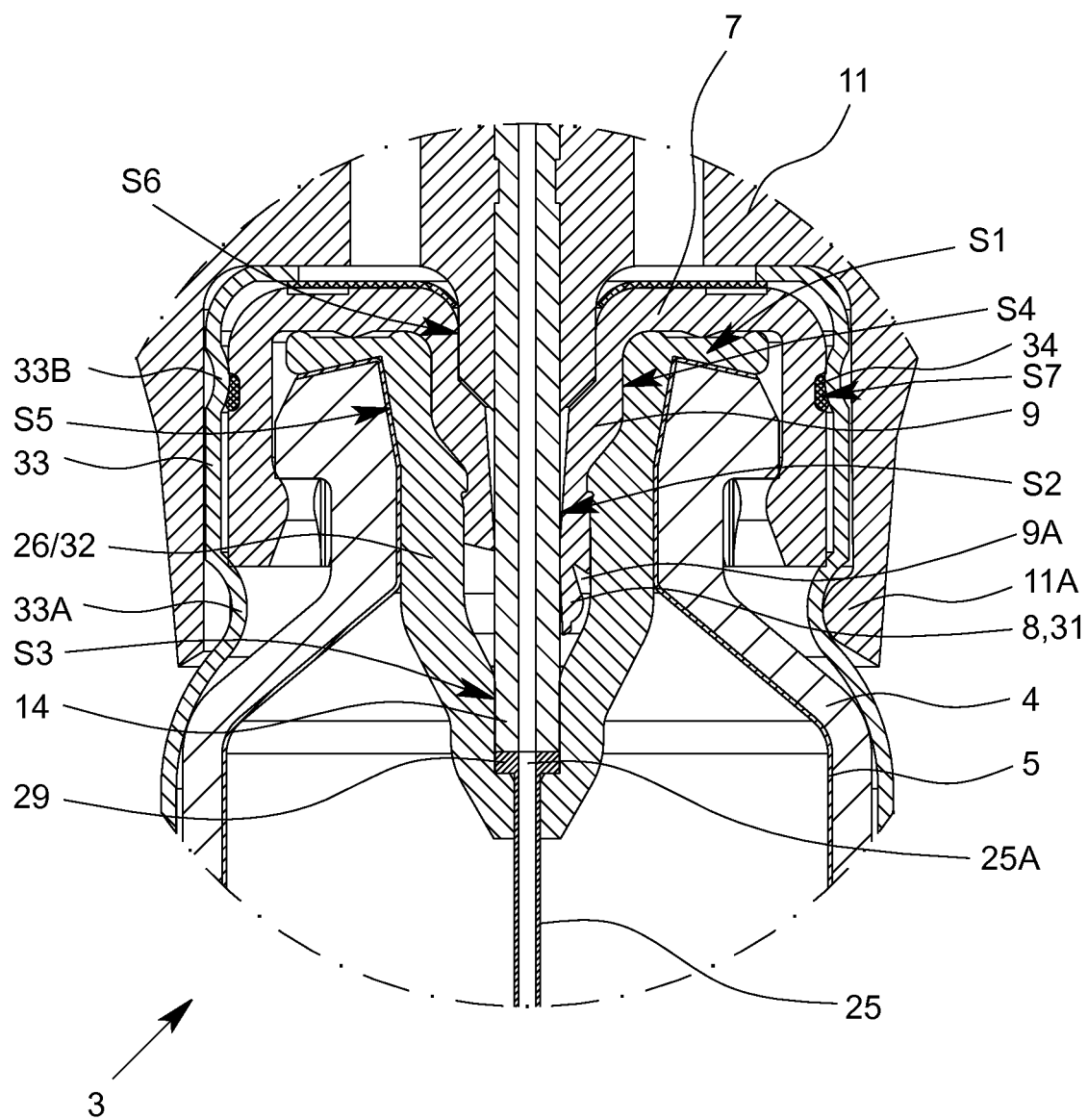
FIG. 22 is a schematic section of the cartridge with an opened membrane or sealing wall according to the seventh embodiment, connected to a partially shown nebulizer.

The cartridge 3 shown in FIG. 3 and FIGS. 21, 22 comprises both, a foil 8A and a membrane or sealing wall 31, preferably wherein a connecting element 14 of the inhaler 1 pierces or breaks/opens both, the foil 8A and the membrane or sealing wall 31, when the cartridge 3 is inserted in and/or connected to the inhaler 1.

The cartridge 3 preferably comprises a (further) sealing S1 between the container 4 and the closure 7. In FIGS. 3 to 8, FIG. 10 and FIG. 20, this sealing S1 is shown as a sealing element 32, for example in the form of a sealing ring located between the container 4 and closure 7. In particular, the sealing S1 and/or sealing element 32 seals the cartridge 3 in the axial direction. However, also other solutions are possible here, particularly preferably a sealing S1 or sealing element 32 as shown in FIGS. 21 and 22 which is described in more detail below in connection with a seventh embodiment of the present invention.

The nebulizer 1 comprises preferably a delivery/pressurizing mechanism 10, preferably a pressure generator or pump, for withdrawal, pressurizing, conveying and/or nebulizing/dispensing of fluid 2, particularly in a preset and optionally in a adjustable dosage amount.

In particular, the delivery mechanism 10 withdraws or sucks fluid 2, namely a dose of the fluid 2, from the cartridge 3, in particular from container 4 and/or bag 5, preferably when cocking or tensioning or loading the nebulizer 1. Subsequently, the withdrawn fluid 2 or dose of fluid 2 is dispensed, in particular pressurized and/or nebulized, preferably in a second step, in which the mechanical energy which has been stored during the earlier tensioning is released.

In particular, the nebulizer 1 comprises an energy store (preferably a drive spring 12) which is loaded (preferably tensioned) during the loading or tensioning process and the energy is released for nebulizing the fluid 2 or dose of fluid 2 which has been drawn into the nebulizer 1 during the tensioning or loading process. Thus, the normal use of the nebulizer 1 encompasses the loading process and the dispensing process.

The nebulizer 1 or delivery mechanism 10 comprises preferably a holder 11 for holding the cartridge 3, the drive spring 12 associated to the holder 11 (partly shown in FIG. 1 and FIG. 2), and/or a blocking element 13 preferably in form of or with a button for preferably manual actuation or depressing.

The blocking element 13 can preferably catch and block the holder 11 and/or can be manually operated to release the holder 11 allowing the drive spring 12 to expand.

The nebulizer 1 or delivery mechanism 10 comprises preferably a conveying/connecting element 14, such as a conveying tube, a non-return valve 15, a pressure chamber 16, a nozzle 17 for nebulizing the fluid 2 and/or a mouthpiece 18.

The completely inserted cartridge 3, preferably its closure 7, is fixed or held in the nebulizer 1 via the holder 11, preferably in a form-fit manner, in particular such that the connecting element 14 fluidically connects the container 4 and/or bag 5 to the nebulizer 1 or delivery mechanism 10.

Preferably, when inserting the cartridge 3 into nebulizer 1 and/or when connecting cartridge 3 to the delivery mechanism 10 the connecting element 14 penetrates into the container 4 and/or bag 5 and/or pierces or breaks seal 8, at least partially, and/or is sealingly received by the connection port 9, in particular in a tight fit manner, particularly preferably forming a sealing S2 between the connection port 9 and connecting element 14.

In particular, the cartridge 3 has or forms an insertion opening, preferably formed in or by closure 7, for the connecting element 14. Said opening preferably comprises a preferably funnel-shaped first portion and a preferably cylindrical second portion. The first portion preferably tapers into the second portion. In particular, the second portion has an at least essentially constant diameter, which preferably corresponds to the diameter of connecting element 14. Said opening can be covered or closed initially, in particular by seal 8.

The first portion is preferably constructed such that it can align and/or guide the connecting element 14 into the second portion.

The second portion preferably has a diameter which is (slightly) smaller than the outer diameter of the connecting element 14. In particular, when receiving the connecting element 14, the second portion flexes/stretches apart to encompass the connecting element 14.

In this way, the sealing S2 is formed between the connecting element 14 and the second portion by press/tight-fit, in particular over at least essentially the entire length of the second portion. Further, the cartridge 3 or closure 7 is preferably adapted to compensate for radial length tolerances of the connecting element 14.

Preferably, the connecting element 14 is constructed as an elongated hollow cylinder, in particular as a needle, and/or comprises a tapered/sharp end.

Preferably, the connecting element 14 is rigid, in particular made of metal, mostly preferred of stainless steel, and/or adapted to pierce or break seal 8, in particular foil 8A and/or membrane or sealing wall 31.

Mostly preferred, the connecting element 14 is constructed as a capillary, in particular having an inner diameter of less than 1 mm or 0.8 mm, mostly preferred less than 0.7 mm or 0.5 mm, and/or more than 0.1 mm or 0.2 mm. However, the inner diameter should not be dimensioned too small as this reduces the flow rate that can be achieved within the connecting element 14.

The nebulizer 1, in particular holder 11, is preferably constructed so that the cartridge 3 can be released or exchanged.

When the drive spring 12 is axially tensioned in the tensioning process or during cocking, the holder 11, the cartridge 3 and the connecting element 14 are moved downwards and/or towards the base of cartridge 3.

Through the movement of the connecting element 14 downwards and/or towards the base of cartridge 3 the volume of pressure chamber 16 is enlarged and/or the pressure within pressure chamber 16 decreased, in particular such that fluid 2 is withdrawn or sucked out of the container 4 and/or bag 5 via the connecting element 14 into the delivery mechanism 10, in particular into pressure chamber 16 through the non-return valve 15. In this state, the holder 11 is caught by the blocking element 13 so that the drive spring 12 is kept compressed. Subsequently, the nebulizer 1 is in the cocked or tensioned state.

During the subsequent relaxation in the dispensing/nebulization process, i.e. after actuation or pressing of the blocking element 13, the connecting element 14 with its now closed non-return valve 15 is moved back towards the pressure chamber 16, in the FIG. 1 and FIG. 2 upwards, thereby decreasing the volume of pressure chamber 16. Due to the now closed non-return valve 15 the fluid 2 or a dose thereof in the pressure chamber 16 is put under pressure. Thus, in this state, the non-return valve 15 acts as a pressing ram or piston.

The pressure generated in this way forces the fluid 2 or the dose thereof through the nozzle 17, whereupon it is nebulized into an aerosol A, as indicated by dashed lines in FIG. 1.

Generally, the nebulizer 1 operates with a spring pressure of 5 MPa to 300 MPa, preferably 10 MPa to 250 MPa on the fluid 2, and/or with a volume of fluid 2 delivered per stroke of 10 µl to 50 µl, preferably 10 µl to 20 µl, in particular about 15 µl. Alternatively, the nebulizer 1 operates with a volume of fluid 2 delivered per stroke of more than 20 µl, in particular about 40 or 50 µl.

The fluid 2 is converted into or nebulized as an aerosol A, the droplets of which have an aerodynamic diameter of up to 20 µm, preferably 3 µm to 10 µm.

Preferably, the generated jet spray is cone-shaped and/or has an opening angle of 20° to 160°, preferably 80° to 100°.

A user or patient (not shown) can inhale the aerosol A generated in this way, preferably while air can be sucked into the mouthpiece 18 through at least one optional air supply opening 19.

The nebulizer 1 comprises preferably a housing 20 with an upper housing part 21, a lower housing part 22 and/or an inner housing part 23.

The inner housing part 23 and/or lower housing part 22 are/is preferably rotatable relative to the upper housing part 21. In particular, the lower housing part 22 is manually operable and/or releasable fixed, particularly fitted or held onto the inner housing part 23, preferably by means of a retaining element.

In order to insert and/or replace the cartridge 3, preferably the housing 20 can be opened and/or the lower housing part 22 can be detached from nebulizer 1, in particular from inner housing part 23.

Preferably, the cartridge 3 can be inserted before the housing 20 is closed and/or before the lower housing part 22 is connected to the inner housing part 23 or upper housing part 21. Alternatively, the cartridge 3 may be inserted, opened and/or fluidically connected to the delivery mechanism 10 automatically or simultaneously when (completely) connecting the lower housing part 22 to the upper housing part 21 and/or the inner housing part 23 and/or when (completely) closing the housing 20 or nebulizer 1.

The lower housing part 22 preferably forms a cap-like lower housing part and/or fits around or over a lower free end portion of the cartridge 3.

Preferably, the nebulizer 1 or drive spring 12 can be manually activated or tensioned or loaded, in particular by actuation or rotation of an actuation member, here preferably by rotation of lower housing part 22 or any other component.

The actuation member, preferably the lower housing part 22, can be actuated, here rotated relative to the upper housing part 21, carrying with it or driving the inner housing part 23.

The inner housing part 23 acts on a gear or transmission to transform the rotation into an axial movement of the holder 11 and cartridge 3. As a result, the drive spring 12 is tensioned in the axial direction by means of the gear or transmission (not shown) formed between the inner housing part 23 and the holder 11.

During tensioning the cartridge 3 and holder 11 are moved axially downwards until the cartridge 3 occupies or assumes an end position, as shown in FIG. 2. In this activated or tensioned state the drive spring 12 is under tension and can be caught or held by the blocking element 13.

During the nebulizing process the cartridge 3 is moved back into its original position (non-tensioned state shown in FIG. 1) by (the force of) the tensioned drive spring 12. Thus, the cartridge 3 executes a lifting or stroke movement during the tensioning process and during the nebulizing process.

As the drive spring 12 is tensioned the cartridge 3 moves with its end portion into the lower housing part 22 or towards the end face thereof.

An aeration means, such as a piercing element 24 arranged in the lower housing part 22, preferably opens or pierces the cartridge 3, preferably container 4, in particular ventilation 6, when the cartridge 3 makes contact with it for the first time. In this way, air can flow into the cartridge 3, in particular container 4, and pressure compensation can take place when fluid 2 is withdrawn from the cartridge 3 during the tensioning of the nebulizer 1. As mentioned above, other constructional solutions are possible as well, in particular when omitting optional bag 5. Such embodiments will be described in the following with regard to FIG. 3 to FIG. 19.

The cartridge 3 according to the various embodiments shown in FIGS. 3 to 23, in particular according to the first embodiment shown in FIG. 3 to FIG. 7, comprises preferably a tube 25, in particular a capillary/dip/conveying tube, particularly preferred for suction and/or conveying of fluid 2 out of the container 4 and/or towards the delivery mechanism 10 or connecting element 14.

The tube 25 is preferably constructed as an elongated hollow cylinder or capillary.

Preferably, the tube 25 comprises a first axial or fixed end 25A and second axial or free end 25B, preferably wherein the first axial or fixed end 25A is fixed/attached to or formed by closure 7 or connection port 9 and/or the second axial or free end 25B is freely moveable within container 4, as will be described below in more detail.

In particular, tube 25 or fixed end 25A is connected directly or indirectly to the closure 7 or connection port 9.

Preferably, the embodiments shown in FIG. 3 to 19 do not comprise a flexible/collapsible bag 5, in particular since the bag 5 would interfere with the tube 25 and/or limit its ability to freely move within container 4. Nevertheless, the embodiments shown in FIG. 3 to 19 might also incorporate a bag 5 as described with regard to FIGS. 1, 2 and 20.

The tube 25 is preferably completely arranged within the container 4 and/or extends preferably completely within the container 4.

Preferably, the tube 25, in particular its fixed end 25A, is mechanically and/or fluidically connected—preferably in a form fitting and/or force fitting manner and/or by bonding—to closure 7 or connection port 9, preferably via an optional adapter 26.

Preferably, the adapter 26 connects the tube 25, i.e. its fixed end 25A, preferably in a form fitting and/or force fitting manner and/or by bonding, to the connection port 9 of closure 7.

In particular, the closure 7 can comprise the adapter 26.

In the embodiment shown in FIG. 3 to 7, the adapter 26 and the tube 25 are preferably formed in one piece. Mostly preferred, the tube 25, in particular its fixed end 25A, widens out into the direction of closure 7 and/or (thereby) forms the adapter 26. Nevertheless, other solution are possible as well, in particular in which adapter 26 is formed as a separate part, as will be described in connection with the second embodiment shown in FIG. 8 and FIG. 9 and the seventh embodiment shown in FIGS. 21 to 23.

Preferably, the adapter 26 is funnel- and/or cone-shaped and/or attached to the connection port 9. In particular, the adapter 26 is flexible and/or adapted to sealingly receive the connection port 9 and/or connecting element 14, in particular its axial end, mostly preferred in a press/tight fit manner. Particularly preferably, sealings S3 and S4 are formed between the adapter 26 and the connecting element 14 or connection port 9, respectively.

Preferably, the adapter 26 forms a seal between the tube 25 and connection port 9 and/or between the tube 25 and connecting element 14, in particular its axial end and/or the outer edge thereof. In particular, the adapter 26 is adapted to connect tube 25 to the connection port 9 and/or to the connecting element 14 in a liquid- and/or gas-tight manner.

Preferably, the connection port 9 and/or adapter 26 are/is adapted to compensate length tolerances of the connecting element 14 and/or comprise/comprises a compensation area for sealingly receiving connecting elements 14 with different lengths, as will be described further below with regard to FIG. 4 to FIG. 7 and FIGS. 21 and 22.

Alternatively, the tube 25 is formed by the connection port 9 and/or moulded onto the connection port 9. In such an embodiment, the connection port 9 and the tube 25 are preferably formed in one piece, in particular wherein the connection port 9 tapers—in particular continuously—into the tube 25.

Preferably, the tube 25, at least its fixed end 25A, is (firmly) held or fixed in a center area of container 4. In particular, the closure 7 or connection port 9, holds or merges/tapers into the tube 25, in particular the fixed end 25A, preferably in a center area of container 4.

Preferably, closure 7 or connection port 9 extends into container 4 such that tube 25 is held in a center area of container 4 and/or the connection port 9 merges/tapers into the tube 25 in a center area of container 4.

Preferably, the tube 25 is shorter than the container 4, i.e. its length is shorter than the height of the container 4, in particular such that the entire/outstretched tube 25 can be arranged within container 4.

In particular, the tube 25 is positioned and/or held within the container 4 in such a way that in the outstretched state the tube 25, i.e. its free end 25B, is contact-free and/or does not reach or barely reaches the wall or bottom of container 4. This reduces the risk of interference between the tube 25 and the container 4 and, thus, a limitation of its movement.

Preferably, the tube 25 comprises a length that is shorter than the height of container 4, but longer than half of the height of container 4.

Preferably, the tube 25 comprises a length of less than 100 mm or 80 mm, in particular less than 70 mm or 60 mm, and/or of more than 5 mm or 10 mm, in particular more than 15 mm or 20 mm.

The length of the tube 25 is preferably defined as the distance of the fixed end 25A to the free end 25B of the tube 25 and/or as the length of the section of the tube 25 having a constant inner and/or outer diameter and/or a constant wall thickness.

As previously mentioned, tube 25 is preferably constructed as a capillary tube, in particular such that—due to the capillary action—fluid 2 is automatically drawn into tube 25, preferably such that the tube 25 gets weighted down with the fluid 2 due to the capillary action. Mostly preferred, both the construction as a capillary and the wettability of tube 25 cause immersion of the tube 25 in fluid 2, preferably independent from the spatial orientation of cartridge 3, as will be described further below.

The capillary action is the ability of a fluid, i.e. a liquid, to flow in narrow spaces, i.e. capillaries, —even in opposition to gravity—due to the wettability of the surface of the capillary and/or adhesion of the fluid to the surface of the capillary.

The gravitational force $F_G$ caused by a liquid column in a—vertical aligned—capillary can be described as:

$$F_G = m \times g = \pi r^2 h \rho g,$$

wherein m is the mass of the liquid column, r is the (inner) radius of the capillary, h is the height/level of the liquid column above the fluid surface/level outside the capillary, $\rho$ is the density of the liquid and g is the gravitational acceleration.

The force F caused by the surface tension of the capillary surface $\sigma_S$ and the surface tension between the capillary surface and the liquid $\sigma_{SF}$ can be described with Young's Equation, explained above, in terms of the surface tension of the liquid $\sigma_F$ and the contact angle $\Theta$ between the liquid and the capillary surface as:

$$F = [\sigma_S - \sigma_{SF}] \times 2\pi r = \cos(\Theta) \sigma_F \times 2\pi r$$

In a stationary state, the force $F_G$ is equal to the force F. Thus, the height h of the liquid column can be described by the equation (also known as Jurin's law):

$$h = 2[\sigma_S - \sigma_{SF}]/[r\rho g] = 2 \cos(\Theta) \sigma_F/[r\rho g]$$

It applies that the height of the fluid/liquid column h in a capillary increases by increasing the surface tension of the capillary surface $\sigma_S$, i.e. the term $|\sigma_S - \sigma_{SF}|$ or $\cos(\Theta) \sigma_F$, and/or by decreasing the radius r of the capillary.

Preferably, the flow area, in particular the inner diameter, of the tube 25 corresponds to and/or matches the flow area and/or inner diameter of the connecting element 14.

Preferably, the inner diameter of the tube 25 is smaller than or particularly preferably the same as the inner diameter of the connecting element 14. In particular, capillary stops at the transition from the tube 25 to the connecting element 14 are thus minimized or prevented.

Preferably, the (smallest) inner diameter of tube 25 is less than 1 mm or less than 0.8 mm, in particular less than 0.7 mm or less than 0.5 mm, and/or more than 0.1 mm or more than 0.2 mm. However, the inner diameter of tube 25 should not be dimensioned too small as this reduces the flow rate within the tube 25.

Preferably, the ratio of the length to the inner diameter of the tube 25 is more than 10 or 20 and/or less than 100 or 80.

Preferably, the height of the fluid/liquid column in the tube 25 caused by the capillary action is at least 20% or 40%, in particular 50% or 80%, of the length of the tube 25.

Because of the capillary action the energy needed for withdrawal of a dose of the fluid 2 out of the cartridge 3 is reduced. Further, the tube 25 gets weighted down with the weight of the fluid 2 that is sucked into the tube 25.

Preferably, the wall thickness of tube 25 is less than 1 mm or 0.8 mm, in particular less than 0.7 mm or 0.6 mm, particularly preferred less than 0.4 mm or 0.3 mm, and/or more than 0.05 mm or 0.1 mm, in particular more than 0.12 mm or 0.14 mm.

The tube 25 is at least partially flexible and/or bendable and/or kink-resistant, in particular such that tube 25 can be bent within container 4 or bag 5 without kinking, at least when being bent above its minimum bending radius.

Figure 6:
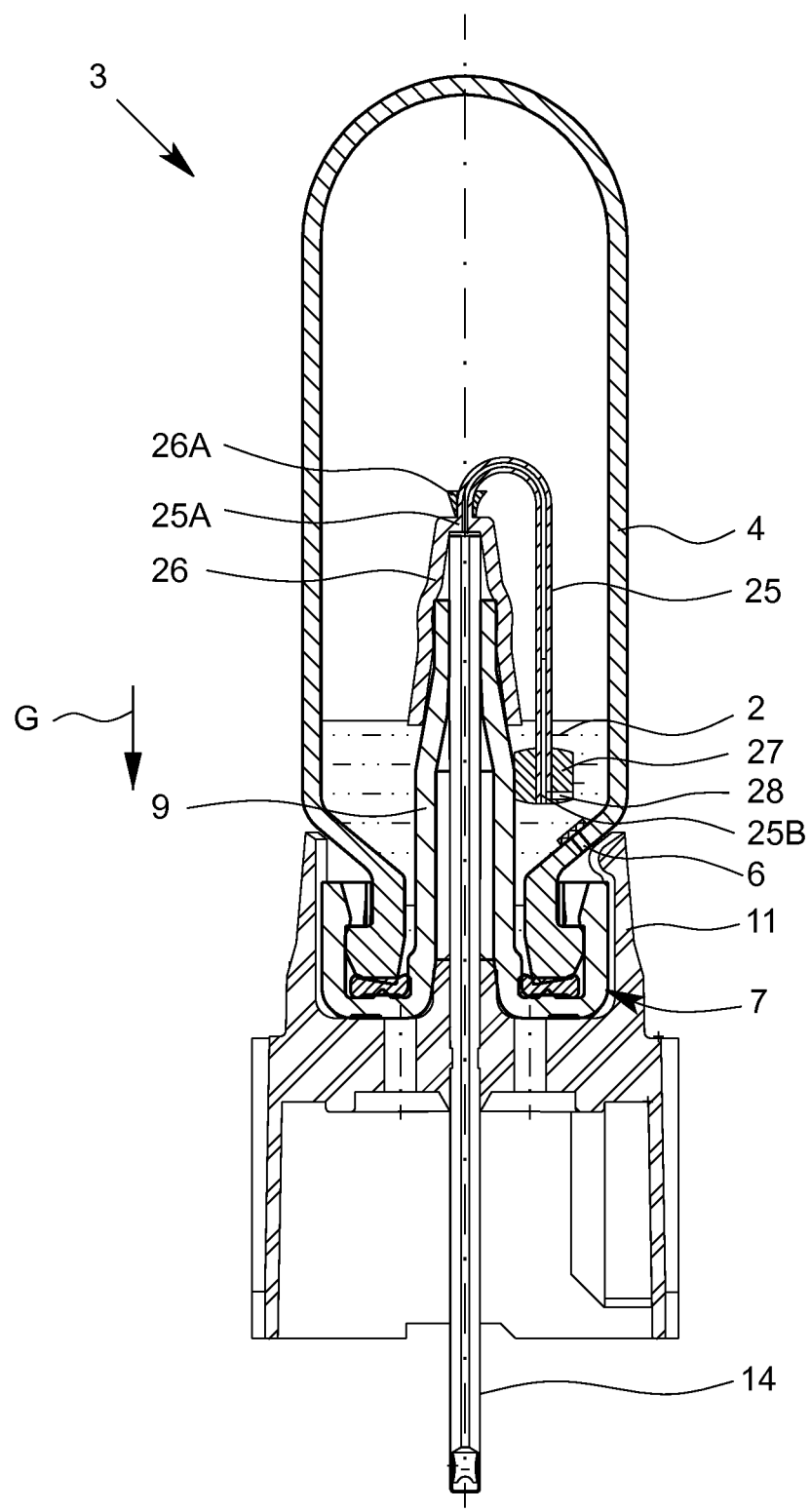
FIG. 6 is a schematic section of the cartridge according to FIG. 4, turned upside down.

Preferably, the cartridge 3 comprises an anti-kink device 26A, as shown exemplary in FIG. 6, which protects the tube 25 from over-bending and/or prevents kinking of the tube 25. The anti-kink device 26A is preferably attached to or formed by the closure 7, connection port 9 and/or adapter 26. In particular, the anti-kink device encompasses or forms a sleeve for a portion of the tube 25 close or adjacent to the fixed end 25A.

Alternatively, the anti-kink device 26A is formed by the tube 25, preferably by the tube walls in the vicinity of the fixed end 25A being thickened.

The anti-kink device 26A preferably has a cylindrical or particularly preferably conical or funnel-like shape, in particular tapered towards the fixed ends 25A. The anti-kink device 26A can be rigid or can be made from a soft material, in particular being partly flexible to support bending of the tube 25 up to a certain bend radius.

The anti-kink device 26A preferably defines or delimits the bend radius of the tube 25.

Most preferably, the tube 25 comprises a minimum bend radius that is less than half, preferably a quarter, in particular a fifth, of the inner diameter of the container 4, preferably wherein the inner diameter of the (cylindric or spheric) container 4 corresponds to the minimum diameter of the cross sectional area of the container 4. In this way, the tube 25 can be bent sufficiently within the container 4 and, thus, allow withdrawal of fluid 2 in other spatial orientations than a vertical alignment, e.g. in a horizontal position.

Preferably, the bend radius of tube 25 is less than 15 mm or 10 mm, preferably less than 8 mm or 6 mm, in particular less than 5 mm or 3 mm, and/or more than 1 mm or 2 mm.

Preferably, the inner diameter of tube 25 is reduced by a maximum of 10% when bending tube 25 to its minimum bending radius. In particular, the minimum bending radius is the radius to which the tube 25 can be bent without kinking and/or without reducing the inner diameter of tube 25 by more than 10% of its initial inner diameter, i.e. the inner diameter of tube 25 in an outstretched/unbent state. This guarantees, that fluid 2 can be withdrawn from container 4 or bag 5 even if the tube 25 is bent to its minimum bending radius.

Preferably, the tube 25 is flexible or bendable and/or adapted in length in such a way that its free end 25B can reach the outermost areas of the container 4 or bag 5, i.e. the upper axial end or top of container 4 and/or the lower axial end or bottom of container 4, as will be described further below.

The tube 25, closure 7, connection port 9 and/or adapter 26 are/is preferably made of rubber, in particular butyl rubber, and/or (flexible) plastic, in particular thermoplastics and/or thermoplastic elastomers, such as polyamide, polyethylene, polypropylene, polybutylene terephthalate or polyether block amide or the like. Other suitable materials might be used as well.

Preferably, the material of the tube 25 and/or adapter 26 is selected in accordance with the properties of the fluid 2, in particular in such a way that the tube 25 and/or adapter 26 are/is wettable with the fluid 2, i.e. that the surface energy of the tube 25 is greater than or equal to the surface tension of the fluid 2 and/or that the contact angle between a drop of the fluid 2 and the surface of the tube 25 is less than 70° or 60°, preferably less than 50° or 30°, mostly preferred less than 20°.

For example, in case the fluid 2 is aqueous and/or comprises an aqueous solution and/or water as solvent and/or has a surface tension of more than 65 mN/m and/or less than 75 mN/m, the material of the tube 25 should have a surface energy of more than 75 mN/m or 80 mN/m. In case the fluid 2 is ethanolic and/or comprises an ethanolic solution and/or ethanol as solvent and/or has a surface tension of more than 15 mN/m and/or less than 30 mN/m, the material of the tube 25 should have a surface energy of more than 30 mN/m or 35 mN/m.

Untreated polyethylene usually has a surface energy between 27 mN/m and 36 mN/m. Untreated polypropylene usually has a surface energy between 28 mN/m and 34 mN/m. Thus, the properties of theses materials need to be adapted when used with a fluid 2 having a higher surface tension, e.g. an aqueous solution, in order to improve the wettability.

To achieve the desired properties of the tube 25, i.e. to increase its surface energy and/or wettability, the tube 25 is preferably surface treated, in particular corona, plasma, flame, wet chemical treated and/or (thin-film) coated.

In particular, such surface treatment may also increase the polarity of the surface of the tube 25 which increases its wettability with aqueous or polar fluids 2, such as water or ethanol.

In addition or alternatively, the tube preferably contains at least one additive, in particular at least one primer, in order to increase its surface energy and/or wettability and/or polarity.

For instance, the surface energy of polyethylene and polypropylene can be increased by plasma surface treatment to more than 40 mN/m.

Additionally or as an alternative, the fluid 2 might be modified with at least one additive, such as benzalkonium chloride, in order to decrease its surface tension.

Preferably, the material of the tube 25 or of its free end 25B is selected such that the density of the tube 25 or its free end 25B is greater, in particular more than 10%, 25% or 50% greater, than the density of the fluid 2, in order to facilitate immersion of the free end 25B in the fluid 2.

For example, in case the fluid 2 is aqueous and/or comprises an aqueous solution and/or water as solvent and/or has a density of more than 1 g/cm$^3$ and/or less than 1.2 g/cm$^3$, the material of the tube 25 or its free end 25B should have a density of more than 1.2 g/cm$^3$ or 1.3 g/cm$^3$. In case the fluid 2 is ethanolic and/or comprises an ethanolic solution and/or ethanol as solvent and/or has a density of more than 0.8 g/cm$^3$ and/or less than 1 g/cm$^3$, the material of the tube 25 or its free end 25B should have a density of more than 1 g/cm$^3$ or 1.1 g/cm$^3$.

Figure 4:
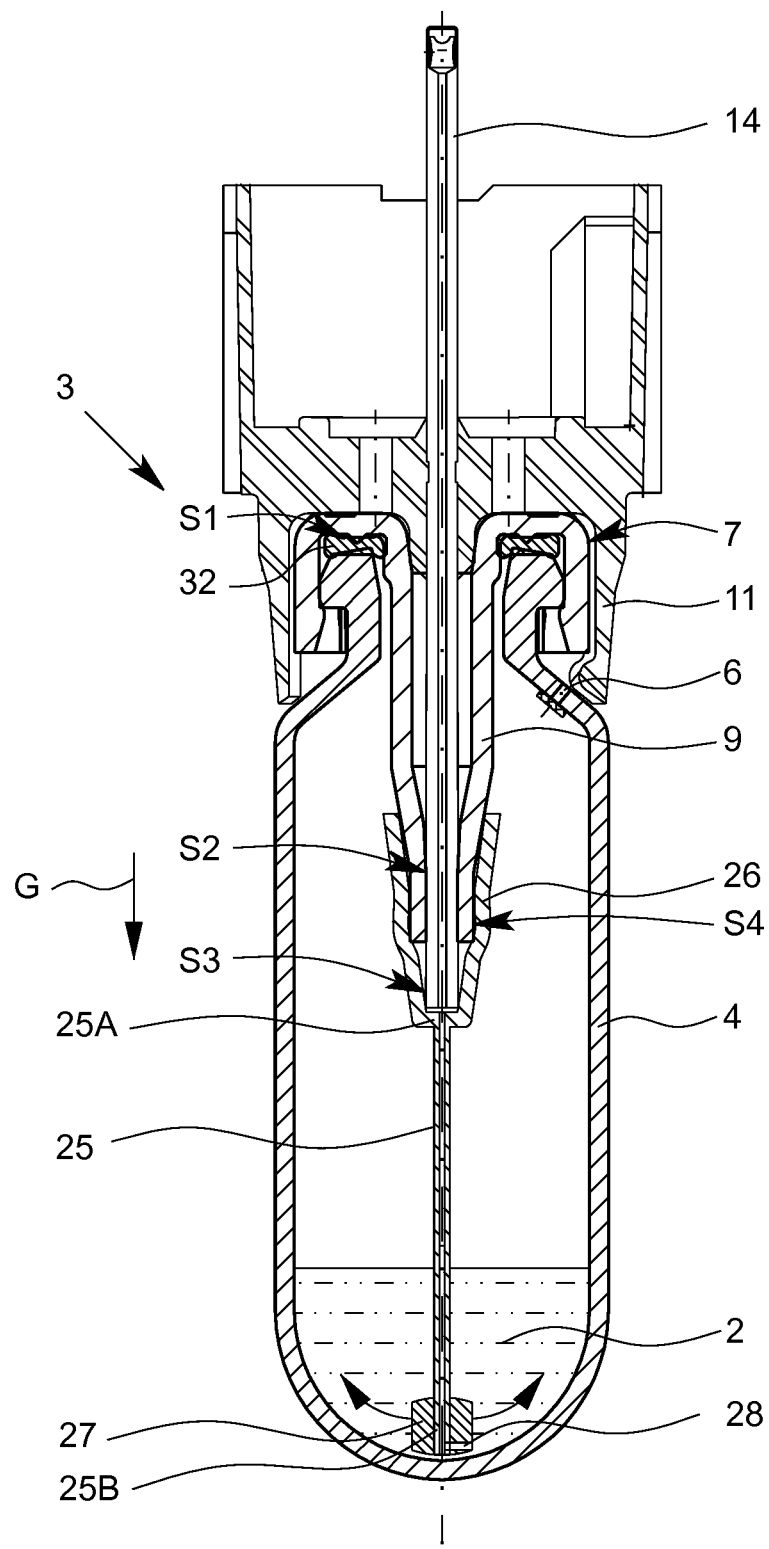
FIG. 4 is a schematic section of the cartridge according to FIG. 3, connected to a partially shown nebulizer.

FIG. 4 shows a schematic section of the cartridge 3 connected to the holder 11 of nebulizer 1. In this state, the connecting element 14 has pierced the seal 8 and extends into the cartridge 3, in particular container 4.

Figure 5:
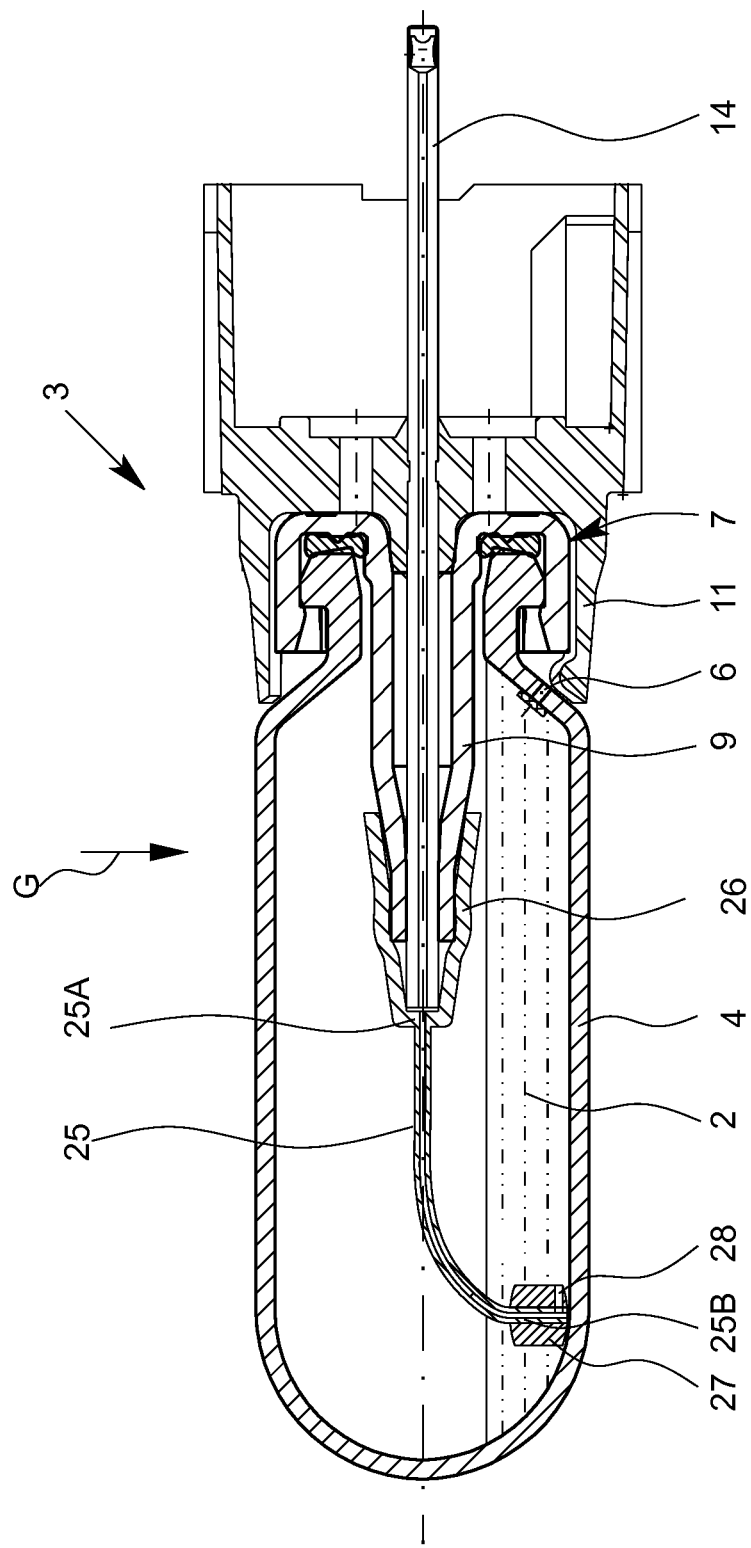
FIG. 5 is a schematic section of the cartridge according to FIG. 4, turned in a horizontal position.

Preferably, the cartridge 3, in particular connection port 9 and/or optional adapter 26, are/is adapted to sealingly receive the connecting element 14, preferably its axial end and/or the outer edge thereof, in particular in a press/tight fit manner and/or such that a fluidic and/or tight connection between cartridge 3 and the delivery mechanism 10 can be established (as shown in FIG. 4 to 6).

Preferably, the connection port 9 and/or the adapter 26 are/is flexible and/or stretchable.

In particular, the connecting element 14—once inserted— and the connection port 9 are connected in a press fit manner.

Mostly preferred, the (flexible) connection port 9 is (laterally) expanded by the connecting element 14, in particular such that a liquid- and/or gas-tight connection or sealing S2 is formed between the connection port 9 and the connecting element 14.

Additionally or as an alternative, the connecting element 14—once inserted—and the adapter 26 are connected sealingly and/or in a press fit manner. In particular the (flexible) adapter 26 is (laterally) expanded by the connecting element 14, preferably its axial end and/or the outer edge thereof, in particular such that a liquid- and/or gas-tight connection or sealing S3 is formed between the connecting element 14, preferably its axial end and/or the outer edge thereof, and the adapter 26.

Here, both the connection port 9 and the adapter 26 are connected sealingly and/or in press fit manner with the connecting element 14. With other words, two sealing locations or sealings S2, S3 are established with the connecting element 14: a first one between the lateral side or shell surface of connecting element 14 and the connection port 9 and a second one between the axial end of the connecting element 14 and the adapter 26.

Preferably, the sealing connection or sealing S2 between the connecting element 14 and the connection port 9 and/or the sealing S3 between the connecting element 14 and the adapter 26 can be established, even when using connecting elements 14 with different lengths and/or when moving the connecting element 14 axially, as the connecting element 14 is laterally/radially sealingly received by and/or connected with the connection port 9 and/or adapter 26. In this way, length tolerances of the connecting element 14 can be compensated.

In the state of the cartridge 3 as shown in FIG. 4, container 4 is almost empty, i.e. the volume of fluid 2 has been reduced such that only a few doses of fluid 2 remain.

Preferably, the cartridge 3 is adapted to be emptied completely and/or that more than 90% or 92%, in particular more than 95% or 96%, of its initial volume of fluid 2 can be withdrawn by the nebulizer 1 or delivery mechanism 10, in particular through tube 25.

Moreover, the cartridge 3 is preferably adapted such that fluid 2 can be withdrawn from container 4 at least essentially independently from its spatial orientation, as illustrated by comparison of FIGS. 4 to 6 with one another.

FIG. 5 shows the cartridge 3 connected to the delivery mechanism 10 according to FIG. 4, but turned or held in a horizontal position, i.e. so that the remaining fluid 2 no longer is collected at the bottom or lower axial end of container 4, but rather at its longitudinal side due to gravity G.

FIG. 6 shows the cartridge 3 connected to the delivery mechanism 10 according to FIG. 4, but turned upside down, i.e. in the state in which cartridge 3 is arranged above delivery mechanism 10 and/or so that the remaining fluid 2 no longer is collected at the bottom or lower axial end of container 4, but rather at its top or upper axial end, i.e. at closure 7, due to gravity G.

Preferably, the tube 25 is flexible or bendable such that its free end 25B bends—preferably automatically—towards the (remaining) fluid 2 or according to gravity G and/or that its free end 25B is kept in the (remaining) fluid 2, in particular such that the fluid 2 can be withdrawn from container 4 at least essentially independently from the spatial orientation of the cartridge 3 and/or from any area of the container 4, preferably even from the outermost areas of container 4, i.e. at the containers 4 lower end or its bottom, at the containers 4 longitudinal side and at the containers 4 upper end or closure 7.

In particular, the fluid 2 is collected at the lowest point within container 4 due to gravity G. Preferably, the free end 25B of the tube 25 is located or positioned automatically at least essentially at or adjacent to said lowest point within the fluid 2 in the cartridge 3 or container 4 for any spatial orientation, in particular even when turned upside down.

Preferably, bending of tube 25 is achieved automatically, in particular due to the own weight/weight force of tube 25 and/or its wettability.

Preferably, the tube 25 is constructed so that it bends—preferably due to its own weight and/or its wettability—by an angle of more than 10°, 20° or 30°, in particular at least essentially 45°, and/or reaches the longitudinal side with its free end 25B, when the cartridge 3 or nebulizer 1 is turned in a horizontal position, as shown in FIG. 5.

In particular, the tube 25 is constructed so that it bends—preferably due to its own weight and/or its wettability—by an angle of more than 90°, 120° or 150°, in particular at least essentially 180°, and/or reaches the containers 4 upper end or closure 7 with its free end 25B, when the cartridge 3 or nebulizer 1 is turned upside down, as shown in FIG. 6.

Optionally, the cartridge 3 comprises an immersion/contact element 27, e.g. a weight, a sponge, an anchor or the like, preferably wherein the immersion element 27 is attached to or formed by the tube 25, in particular its free end 25B.

Preferably, the tube 25 and the immersion element 27 are separate parts. Nevertheless, tube 25 and immersion element 27 might be formed in one piece. For example, the wall thickness of the free end 25B of the tube 25 might be increased compared to the adjacent wall thickness. In this way, the free end 25B of tube 25 might form the immersion element 27.

In an alternative embodiment (not shown), the immersion/contact element 27 is formed by an enlargement of the material of tube 25 and/or in one piece with tube 25.

The immersion element 27 preferably weighs more than 1 mg or 3 mg, in particular more than 5 mg or 10 mg, and/or less than 500 mg or 400 mg, in particular less than 300 mg or 200 mg.

The immersion element 27 comprises preferably a volume of more than 1 mm³ or 2 mm³ and/or less than 1000 mm³ or 125 mm³.

Preferably, the immersion element 27 is adapted to increase the weight force acting on the tube 25, in particular its free end 25B, causing bending of tube 25 in accordance with gravity G and/or the spatial orientation of nebulizer 1 or cartridge 3.

Preferably, tube 25 and/or immersion element 27 comprises an optional lateral inlet 28, such as a cut-out, recess or canal, preferably extending laterally/radially relative to the longitudinal extension or axial canal/inlet of tube 25 and/or through the wall of tube 25 or immersion element 27.

Preferably, fluid 2 can be sucked in laterally/radially via the lateral inlet 28 and/or via two different inlets, e.g. the axial canal/inlet of tube 25 and additional lateral inlet 28. This prevents that the tube 25 adheres to the wall of container 4 while withdrawing fluid 2 and/or that the wall of container 4 closes tube 25 (completely).

In particular, the immersion element 27 can be adapted such that at least one of the inlets has a distance from the wall of container 4 regardless of the orientation or position of the tube 25 or immersion element 27. This further prevents blocking of the free end 25B.

The immersion element 27 has preferably a greater, in particular by more than 10%, 25% or 50% greater, density than the fluid 2 in order to facilitate immersion in the fluid 2.

For example, in case the fluid 2 is aqueous and/or comprises an aqueous solution and/or water as solvent and/or has a density of more than 1 $g/cm^3$ and/or less than 1.2 $g/cm^3$, the material of the immersion element 27 should have a density of more than 1.2 $g/cm^3$ or 1.3 $g/cm^3$. In case the fluid 2 is ethanolic and/or comprises an ethanolic solution and/or ethanol as solvent and/or has a density of more than 0.8 $g/cm^3$ and/or less than 1 $g/cm^3$, the immersion element 27 should have a density of more than 1 $g/cm^3$ or 1.1 $g/cm^3$.

In particular, when providing an immersion element 27 having a density greater than the density of the fluid 2, it is possible for the tube 25 to be of a material with a density that is similar to or even smaller than the density of the fluid 2.

The tube 25, adapter 26 and/or immersion element 27 are/is wettable and/or comprise/comprises preferably an at least partially wettable, in particular hydrophilic and/or polar, surface. In particular, at least the free end 25B of tube 25 comprises a partially wettable, in particular hydrophilic and/or polar, surface. However, it is preferred that the entire surface of tube 25 is wettable, in particular hydrophilic and/or polar.

Preferably, the outer/shell and/or inner surface of tube 25, adapter 26 and/or immersion element 27 is at least partially surface treated, in particular corona, plasma or flame treated, preferably in order to increase its polarity and/or wettability.

Due to the hydrophilic and/or polar surface and/or polarity/wettability of tube 25, adapter 26 and/or immersion element 27, the tube 25, adapter 26 and/or immersion element 27, in particular their/its surface, get/gets easily wetted with fluid 2 and/or, once wetted and/or immersed in the fluid 2, the tube 25, at least its free end 25B, is kept/pulled in the fluid 2, in particular due to adhesion and/or cohesion of the fluid 2.

The wettability, in particular the hydrophilic and/or polar characteristics, of the tube 25 and/or immersion element 27 help to bend tube 25 in accordance with the spatial orientation of the cartridge 3 or gravity G so that the tube 25, in particular its tip or free end 25B, is kept within fluid 2 and/or so that a fluidic connection from fluid 2 in cartridge 3 to delivery mechanism 10 is maintained, preferably independently from any movement or change of the spatial orientation of cartridge 3 or nebulizer 1. Thus, fluid 2 can be withdrawn form cartridge 3 even when a patient of nebulizer 1 moves the nebulizer 1 while using it, e.g. by turning it in a horizontal position or even upside down.

In particular due to the (attached) immersion element 27, the—outer and/or inner—surface area of tube 25, and, thus, the contact surface between tube 25 and fluid 2, is preferably increased at its free end 25B, in particular such that the adhesion effect is further intensified.

In a mostly preferred embodiment (not shown), the immersion/contact element 27 or the free end 25B of tube 25 might be funnel- or cone-shaped. In particular, the inner and/or outer diameter of tube 25 might increase towards the free end 25B, preferably such that the tube 25 comprises an enlarged contact surface at its tip.

Further, the wettability, in particular the hydrophilic and/or polar characteristics, of optional adapter 26 help to avoid bubble formation at its inner surface. In particular, the adapter 26 gets easily wetted with fluid 2 on its inner surface such that no gas bubbles are collected at the transition area between the adapter 26 and connection port 9.

The fluid 2 is preferably a polar fluid and/or comprises a polar solvent, such as water. In particular, the fluid 2 or a component thereof comprises polar molecules and/or dipole moments. This supports the wettability of tube 25 with fluid 2 and, thus, the interaction between the surface of tube 25 and fluid 2, as described above. Nevertheless, a non-polar fluid 2 can also be used.

Preferably, the contact angle between a drop of fluid 2 and the surface of tube 25 and/or immersion element 27 is less than 90° or 70°, in particular less than 50° or 30°, particularly preferred less than 200 or 5°. According to an especially preferred embodiment the contact angle between a drop of fluid 2 and the surface of tube 25 and/or immersion element 27 is between 0° and 2°.

Optionally, the container 4 is less wettable than tube 25 and/or comprises an at least partially hydrophobic and/or non-polar (inner) surface or layer. According to such an embodiment, the container 4, in particular its (inner) surface or layer, might be coated with a hydrophobic and/or non-polar material and/or be made of a hydrophobic and/or non-polar material. In this way, the wettability of the container 4 is decreased so that less fluid 2 sticks to the (inner) surface or layer of container 4. Thus, in a synergetic manner, a hydrophilic and/or polar tube 25 and a hydrophobic and/or non-polar container 4 facilitate to increase the volume of fluid 2 that can be withdrawn from the cartridge 3.

For example, the container 4 might be made of or coated with polytetrafluoroethylene, waxes, like paraffin wax, or the like.

Preferably, the contact angle between a drop of fluid 2 and the surface of the container 4 is larger than 70° or 90°, in particular larger than 1000 or 110°, particularly preferred larger than 130° or 140°.

Figure 7:
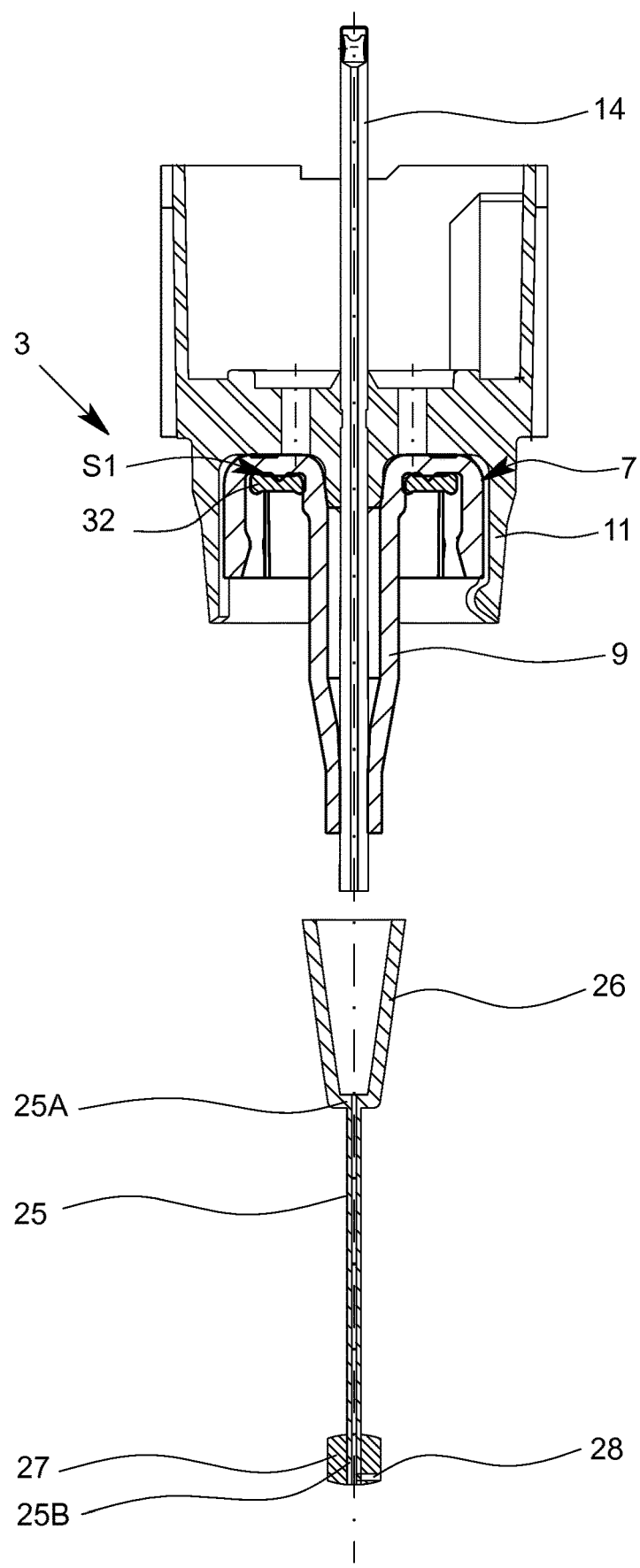
FIG. 7 is a magnified view of a tube of the cartridge according to FIG. 3, moved away from a connection port connected to a partially shown nebulizer.

FIG. 7 shows the tube 25 with funnel- and/or cone-shaped adapter 26 moved away from the connection port 9 and illustrates an assembly state of the cartridge 3 before the tube 25 is press-fitted onto connection port 9 in order to establish a liquid- and/or gas-tight connection or sealing S4 between both parts, as mentioned before. The funnel- and/or cone-shape of the tube 25/adapter 26 allows to sealingly connect the tube 25 to the connection port 9 as well as to connecting element 14.

In the following, further embodiments of the present invention will be described, wherein only relevant differences or additional aspects will be emphasized. The previous explanations apply preferably in addition or in a similar manner and lead to similar features and advantages even if not repeated.

Figure 8:
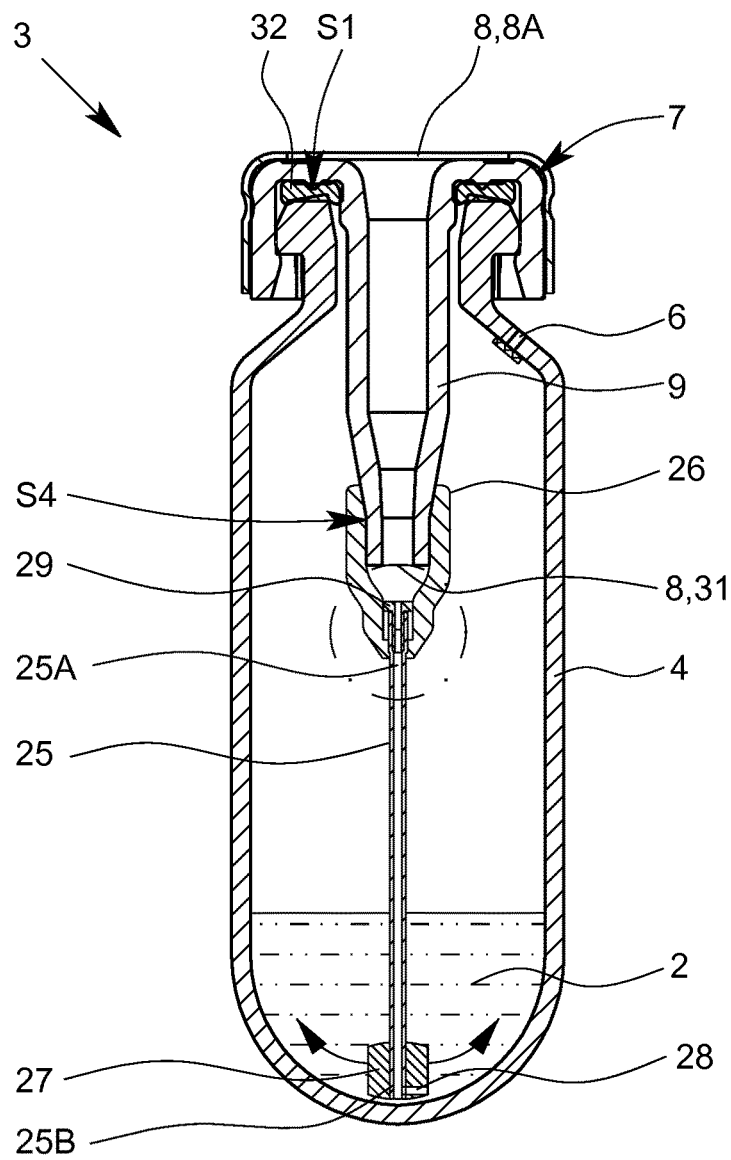
FIG. 8 is a schematic section of a cartridge according to a second embodiment of the invention.
Figure 9:
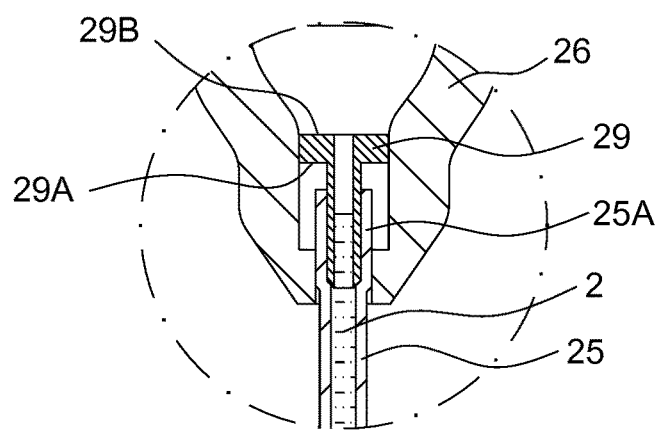
FIG. 9 is a schematic detail of the cartridge according to FIG. 8.

FIG. 8 shows the cartridge 3 according to a second embodiment of the invention. FIG. 9 shows a schematic detail of the cartridge 3 in the area of the fixed end 25A of tube 25.

As mentioned above, the cartridge 3, in particular the connection port 9 and/or adapter 26, are/is adapted to compensate length tolerances of the connecting element 14 and/or to sealingly receive connecting elements 14 with different lengths.

According to the second embodiment, the cartridge 3 comprises preferably an intermediate piece 29 to fluidically connect tube 25 to connection element 14 (not shown in FIG. 8 and FIG. 9), preferably wherein length tolerances of the connecting element 14 can be compensated by the intermediate piece 29, in particular by moving the intermediate piece 29 axially, as will be described in the following.

The intermediate piece 29 is preferably arranged at the fixed end 25A of tube 25 and/or within adapter 26.

In the embodiment shown in FIG. 8 and FIG. 9, adapter 26 and tube 25 are two separate parts. However, adapter 26 and tube 25 might also be formed in one piece, as mentioned in connection with the first embodiment shown in FIG. 3 to FIG. 7.

Preferably, the intermediate piece 29 forms and/or is constructed as a transition/connection from the tube 25 to the connecting element 14. In particular, the intermediate piece 29 is adapted to reduce flow losses at the transition from tube 25 to connecting element 14.

Mostly preferred, the intermediate piece 29 forms a (capillary) transition from tube 25 to connecting element 14, in particular in such a way that a continuous capillary is formed by connecting element 14, tube 25 and intermediate piece 29, i.e. without any capillary stop and/or enlarged flow area causing interruption of the capillary action. In this way, the fluid 2 can be withdrawn up to the connecting element 14 by the capillary action and/or without any capillary stop.

The flow area, in particular the (smallest) inner diameter, of intermediate piece 29 is equal to and/or at least essentially matches the flow areas, in particular the (smallest) inner diameters, of tube 25 and connecting element 14, in particular in order to form a continuous transition from the tube 25 to the connecting element 14 and/or to prevent the formation of bubbles at the transition.

Preferably, the intermediate piece 29 is adapted to reduce/minimize enlargements of the flow area and/or to avoid any dead volume at the transition from the tube 25 to the connecting element 14.

Preferably, the (widest/largest) flow area at the transition from the tube 25 to the connecting element 14, in particular from tube 25 to the intermediate piece 29 and/or from the intermediate piece 29 to the connecting element 14, is at least essentially equal to and/or not greater than 120% of the (smallest or largest) flow area of the connecting element 14, the tube 25 and/or intermediate piece 29.

Preferably, the (widest/largest) flow area at the transition from the tube 25 to the connecting element 14, in particular from tube 25 to the intermediate piece 29 and/or from the intermediate piece 29 to the connecting element 14, is less than 1 mm$^2$ or 0.30 mm$^2$.

Mostly preferred, intermediate piece 29 and tube 25 and/or intermediate piece 29 and connecting element 14 are (sealingly) insertable into each other. In the embodiment shown in FIG. 8 and FIG. 9, the intermediate piece 29 is preferably insertable into tube 25. However, tube 25 can also be insertable into intermediate piece 29.

Preferably, the intermediate piece 29 is constructed as a piston or plunger and/or comprises or forms a stop 29A, preferably wherein the intermediate piece 29 is insertable into tube 25 until the stop 29A hits the axial end, in particular the front surface, of tube 25.

Preferably, at least one of the tube 25 and the intermediate piece 29 is flexible/deformable/stretchable, in particular such that when connecting the tube 25 to the intermediate piece 29 a transition is formed having an at least essentially constant flow area, as most clearly shown in FIG. 9.

Preferably, the intermediate piece 29 is rigid and the tube 25 is flexible, in particular stretchable, such that when inserting intermediate piece 29 into tube 25 the tube 25 is expanded.

Preferably, the intermediate piece 29 comprises a (flat) contact surface 29B for the connecting element 14, in particular wherein the contact surface 29B is arranged on the side turned away from tube 25.

Preferably, when inserting the connecting element 14 into the connection port 9, the connecting element 14 hits intermediate piece 29 axially, in particular its contact surface 29B, preferably such that the connecting element 14, in particular its axial end, sits flush and/or forms a sealing connection with the intermediate piece 29, in particular its contact surface 29B. However, other solutions are possible as well. In particular, intermediate piece 29 and connecting element 14 may be (sealingly) insertable into each other, as described previously in connection with tube 25.

The intermediate piece 29 is preferably adapted to compensate length tolerances of connecting element 14. In particular, intermediate piece 29 is axially movable relative to tube 25 in order to compensate length tolerances of connecting element 14.

In the delivery state, as shown in FIG. 8 and FIG. 9, the intermediate piece 29 is preferably only partially inserted into tube 25, in particular such that the intermediate piece 29 might further be pushed into or onto tube 25.

The delivery state is to be understood as the state of the cartridge 3 before being inserted into the nebulizer 1.

Preferably, when inserting connecting element 14 into connection port 9 the connection element 14 hits the intermediate piece 29, in particular its contact surface 29B, and/or pushes/moves the intermediate piece 29 (further) into or onto tube 25 depending on the axial length of the connecting element 14. In this way, it is possible to compensate a variation in length of the connecting elements 14 and/or to provide a sealed connection between connecting element 14 and tube 25 independently from variations in length of the connecting elements 14.

The present invention allows, supports or insures that the connecting element 14 is sealingly connected to tube 25 at its axial end, in particular via the intermediate piece 29 and/or independently from possible length variations of different connecting elements 14.

Further, the connecting element 14 and the tube 25 form or comprise a continuous capillary and/or comprise an at least essentially constant flow area, in particular via intermediate piece 29. Empty spaces, gaps and/or (sharp) enlargements of the flow area at the transition from tube 25 to connecting element 14 that might catch bubbles and/or lead to a capillary stop are minimized or prevented, in particular such that a continuous capillary transition is formed.

FIG. 10 shows the cartridge 3 according to a third embodiment of the invention. FIG. 11 shows a schematic detail of the cartridge 3 according to FIG. 10 in the area of the free end 25B of the tube 25.

FIG. 12 shows a schematic detail similar to FIG. 11, but with the cartridge 3 and/or tube 25 and/or free end 25B in a different spatial orientation.

In the third embodiment, the immersion element 27 is preferably arranged around the tube 25 and/or encompasses or covers the tube 25.

Preferably, the tube 25 is not encompassed or covered by the immersion element 27 along the entire length thereof. In particular, the tube 25 comprises a portion 25C which is not encompassed or covered by or does not comprise the immersion element 27 and another portion 25D encompassed or covered by or comprising the immersion element 27.

The portion 25D preferably comprises the free end 25B or is adjacent to the free end 25B of the tube 25. The portion 25C preferably comprises the fixed end 25A or is adjacent to the fixed end 25A. However, also other solutions are possible, for example the immersion element 27 being located in a middle portion of the tube 25. Also solutions are possible where a plurality of immersion elements 27 are distributed along the entire length of the tube 25 or a portion thereof.

In FIG. 10, the immersion element 27 has preferably a conical shape and/or tapers towards the free end 25B of the tube 25. However, also other shapes are possible, for example an at least essentially cylindrical shape or the like.

FIG. 10 shows the cartridge 3 connected to the delivery mechanism 10 in a similar position as in FIG. 5, in a turned or horizontal position, i.e. so that the remaining fluid 2 no longer is collected at the bottom or lower axial end of container 4, but rather at its longitudinal side due to gravity G. However, the preferred normal operating position of the cartridge 3 and/or nebulizer 1 according to the third embodiment is the position where the remaining fluid 2 is collected at the bottom or lower axial end of the container 4 (not shown), as in the previous embodiments.

In the normal operating position, the tube 25 extends at least essentially straight and/or not (highly) bent, with the free end 25B being located close to the bottom of the container 4 in order to be immersed in the fluid 2 even if the container 4 is almost empty.

When tilted, the tube 25 preferably bends, such that the free end 25B remains immersed in the fluid 2.

In particular, only the portion 25C of tube 25, which is not encompassed by the immersion element 27 and/or adjacent to the fixed end 25A does bend and/or is bendable. The portion 25D of tube 25 which is encompassed by the immersion element 27 preferably does not bend and/or is rigid or not bendable and/or is prevented from bending by the immersion element 27. This is illustrated in FIG. 10 which shows the cartridge 3 in a horizontal position, with the encompassed portion 25D being unbent, and the other portion 25C being bent due to gravity G and/or wettability of tube 25 and/or immersion element 27.

Preferably, the immersion element 27 of the third embodiment has similar characteristics as the immersion element 27 described in connection with the first embodiment, in particular being wettable with the fluid 2 and/or having a higher surface tension as the fluid 2, and/or having a greater density as the fluid 2, such that the free end 25B remains immersed in the fluid 2.

Preferably, the surface of the immersion element 27 is hydrophilic and/or polar and/or has a higher surface tension as the fluid 2. This, in connection with the preferably hydrophobic and/or non-polar inner surface of the container 4 and/or bag 5 ensures that the immersion element 27 and said inner surface do not come in direct contact with each other and/or stick together.

In particular, the immersion element 27 can be surface-treated, e.g. to realize the hydrophilic characteristics, as described in connection with the first embodiment.

Preferably, the immersion element 27 is made of plastics, in particular a plastics material having a higher density than water, such as polytetrafluorethylene, silicone or the like. However, the immersion element 27 can also be made from other materials, for example from metal, ceramics or the like.

The length of the immersion element 27 and/or portion 25D encompassed by the immersion element 27 is preferably greater than the length of the portion 25C not encompassed by the immersion element 27, in particular more than 2 times greater and/or less than 10 times greater. The immersion element 27 preferably covers or encompasses more than 60% and/or less than 90% of the tube 25.

Preferably, the length of the immersion element 27 exceeds the diameter of the cartridge 3.

The wall thickness of the tube 25 or of the bendable portion 25C is preferably selected thin enough to allow for a sufficient bending of the bendable portion 25C. Preferably, said wall thickness is less than 0.2 mm, in particular less than 0.15 mm, particularly preferred less than 0.12 mm and/or more than 0.05 mm, in particular more than 0.08 mm.

The weight of the immersion element 27 according to the third embodiment is preferably such that the desired bending characteristics of the tube 25 are realized. In particular, the weight of the immersion element 27 is determined by the length of the immersion element 27 or corresponding tube portions 25C, 25D and/or the wall thickness of the tube 25.

Particularly, the thicker the walls of the tube 25 and/or the shorter the bendable tube portion 25C, the greater the weight of the immersion element 27 needs to be in order to achieve the same bending characteristics.

The immersion element 27 according to the third embodiment preferably weighs more than 0.5 g, in particular more than 0.8 g and/or less than 1.5 g, in particular less than 1.2 g, particularly preferably at least essentially 1 g, in particular to allow for sufficient bending of the tube 25 with the aforementioned preferred wall thickness and/or length of tube portion 25C.

The immersion element 27 and the tube 25 are preferably connected in a tight-fit manner, in particular such that no air or fluid 2 can be trapped between the tube 25 and immersion element 27.

The tube 25 and immersion element 27 are preferably formed as separate parts, in particular made of different materials, but can also be integrally formed or as one piece.

The tube 25 or immersion element 27 preferably comprises a valve 30 which is opened or closed depending on the spatial orientation or position of the valve 30 and/or tube 25. In the example shown in FIGS. 10 to 12, the valve 30 is located at or close to the free end 25B of the tube 25. However, the valve 30 could also be located at the fixed end 25A or somewhere in between both ends.

The valve 30 is preferably constructed such that it is open in the normal operating or upright position of the cartridge 3 and/or valve 30 and/or when the tube 25 is in an at least essentially unbent position. Preferably, the valve 30 remains open when the cartridge 3 and/or valve 30 is tilted or turned into the horizontal position and/or any position in between the upright and the horizontal position.

The valve 30 is preferably constructed such that it is closed when the cartridge 3 and/or valve 30 is in an upside down position or an inclined position between the horizontal position and the upside down position and/or when it cannot be guaranteed that the free end 25B of the tube 25 is immersed in the fluid 2.

For example, if the tube 25 and/or immersion element 27 is adapted such that the tube portion 25D which is rigid and/or not (sufficiently) bendable, exceeds the inner diameter of the container 4, it is not possible for the tube 25 or its bendable portion 25C to bend by 90°, 120°, 150° or more due to the container walls limiting such movement. The same applies for very slim container 4 having a small diameter compared to its longitudinal extension. In this case, the length of the tube 25 is much bigger than the diameter of the container 4 such that the tube 25 could get stuck at the container wall in the upside down position. Also when using a flexible tube 25 together with a collapsible bag 5, it could happen that the tube 25 gets stuck or jammed in folds of the bag 5.

In the cases where, due to the construction of the cartridge 3, it is a priori not possible for the tube 25 to bend such that its free end 25B is always immersed in the fluid 2, the valve 30 can be located anywhere at the tube 25, in particular its free end 25B or fixed end 25A, or also within the adapter 26, connection port 9 or closure 7. An example is the case where the rigid tube portion 25D exceeds the inner diameter of the container 4.

However, if the cartridge 3 is constructed such that the tube 25 can in principle reach any point within the container 4, the valve 30 is preferably arranged at or near the free end 25B. In this way, it is ensured that opening and closing of the valve 30 does not depend on the orientation of the cartridge 3, but only on the orientation of the free end 25B. For example, in FIGS. 4 to 6 the cartridge 3 is shown in different spatial orientations, however, the free end 25B of the tube 25 always points into the direction of gravity G, i.e. is in all three cases in the same spatial orientation. In this orientation, the valve 30 is preferably open. However, if the free end 25B points into at least essentially the direction opposite to gravity G, as exemplarily shown in FIG. 12, the valve 30 is preferably closed. This preferably ensures that the valve 30 is only open when the free end 25B is immersed in the fluid 2.

In the following, a preferred construction of the valve 30 is described in greater detail. However, also other structural solutions are possible.

The valve 30 preferably comprises a valve ball 30A which is freely moveable in a valve chamber 30B.

The valve ball 30A is preferably made of a material, in particular plastics material, that has a greater density than the fluid 2 such that the valve wall 30A will sink in the fluid 2 due to gravity G.

The diameter of the valve ball 30A is preferably greater than the inner diameter of the free end 25B and/or tube 25, the valve ball 30A in particular being adapted to close the free end 25B in an at least essentially upside down orientation of the valve 30 and/or free end 25B.

The walls of the valve chamber 30B are preferably formed by the immersion element 27.

Preferably, the tube 25 or its free end 25B is fluidically connected to the valve chamber 30B.

The walls of the valve chamber 30B preferably comprise openings or inlets, in particular an inlet at its axial end and lateral inlets 28 at the side walls. The diameter of the inlets are preferably smaller than the diameter of the valve ball 30A such that the valve ball 30A cannot escape the valve chamber 30B.

Preferably, the openings of the chamber 30B are arranged such that not all of the inlets can be closed off by the valve ball 30A simultaneously. This preferably ensures that at least one inlet will remain open regardless of the spatial orientation of the valve 30.

Alternatively, the valve chamber 30B can be at least essentially cage-like, in particular the walls of the valve chamber 30B being grid-like, preferably on all sides, with the valve ball 30A being confined in said cage-like valve chamber 30B. This preferably ensures that the valve chamber 30B is filled with fluid 2 when immersed.

FIG. 12 shows the valve 30 in an upside down position, i.e. the position where the free end 25B of the tube 25 points against gravity G and/or is not necessarily immersed in the fluid 2. In this case, the valve ball 30A preferably rests on the free end 25B and, thus, closes said free end 25B, i.e. the inlet of the tube 25. In particular, the valve ball 30A sitting on the free end 25B prevents air from getting into the tube 25.

FIGS. 13 to 18 show the cartridge 3 according to a fourth embodiment of the present invention. The figures show the cartridge 3 in a schematic view, where one side of the container 4 has been removed such that the inside of container 4 becomes visible.

Figure 13:
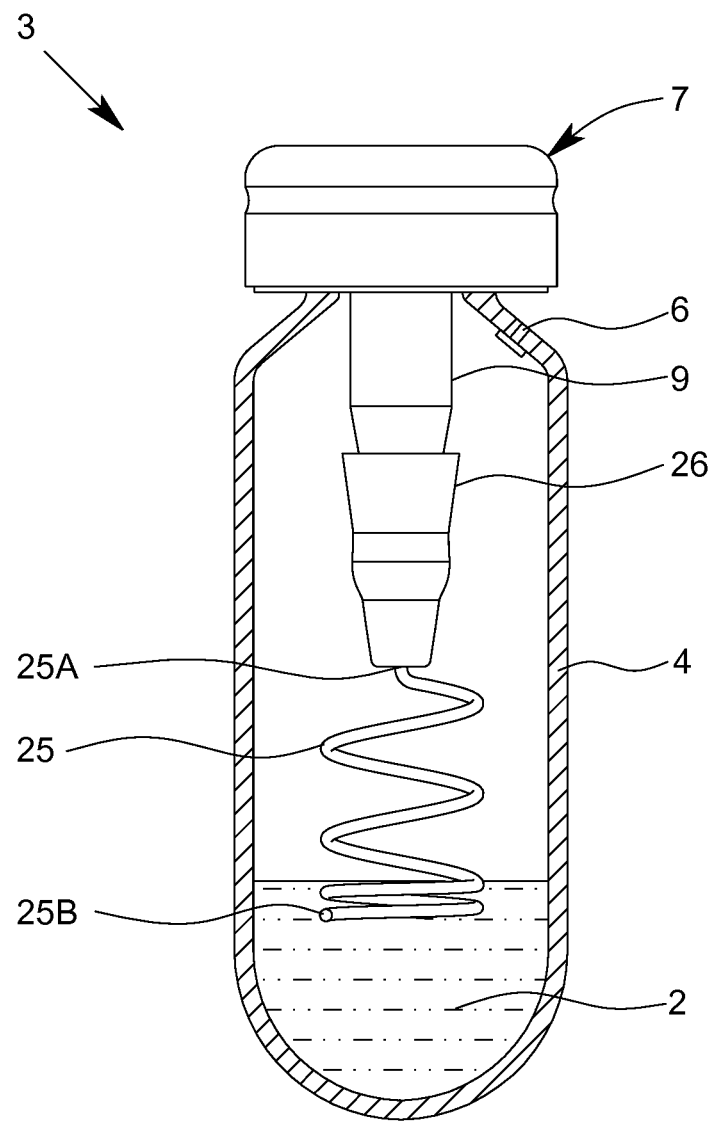
FIG. 13 is a schematic view of the cartridge with a helically shaped tube according to a fourth embodiment of the invention.
Figure 14:
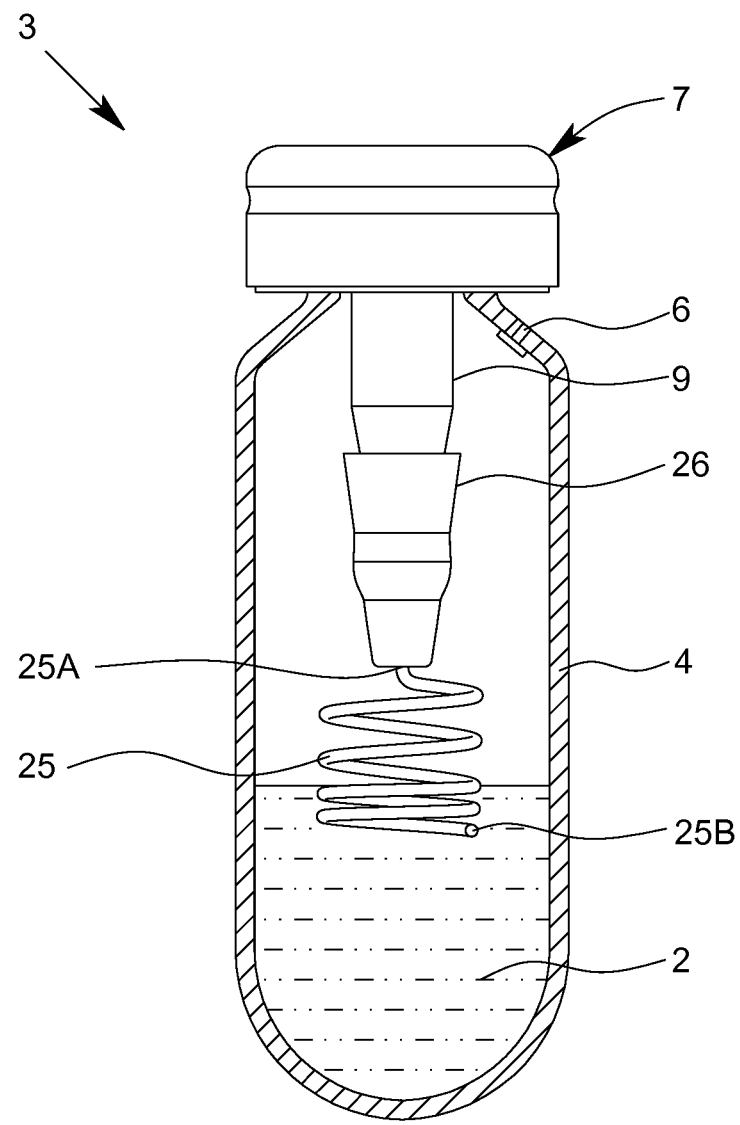
FIG. 14 is a schematic view of the cartridge according to FIG. 13 with higher filling level of fluid.
Figure 15:
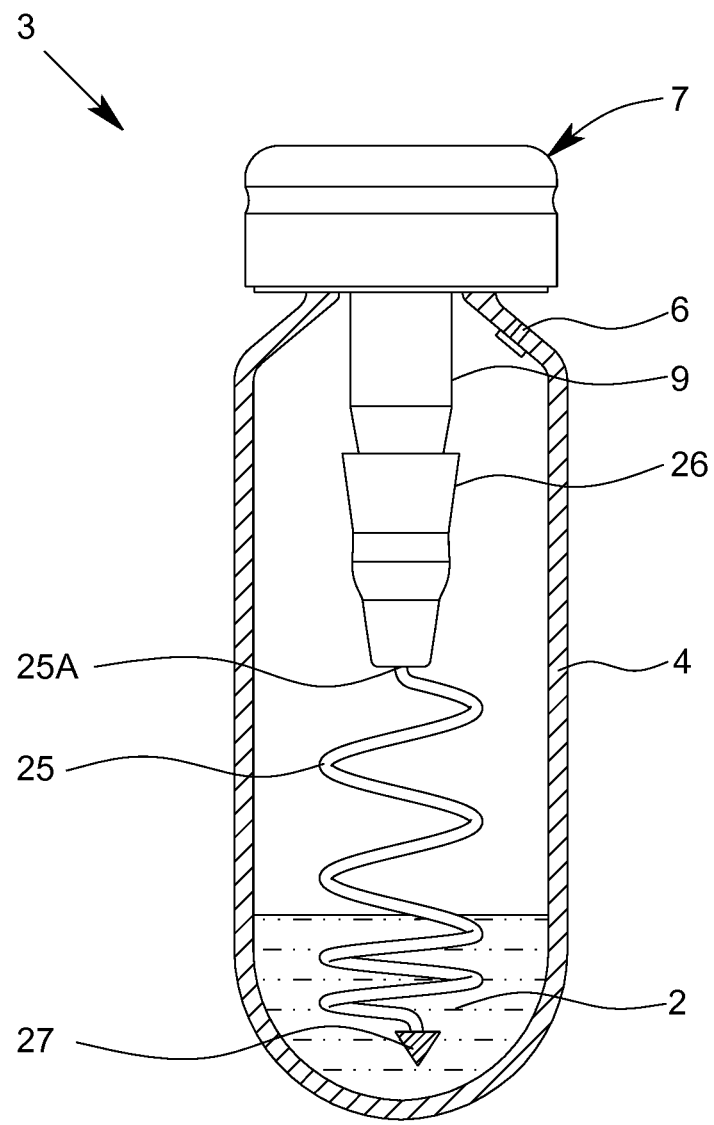
FIG. 15 is a schematic view of the cartridge according to FIG. 13 with additional immersion element.
Figure 16:
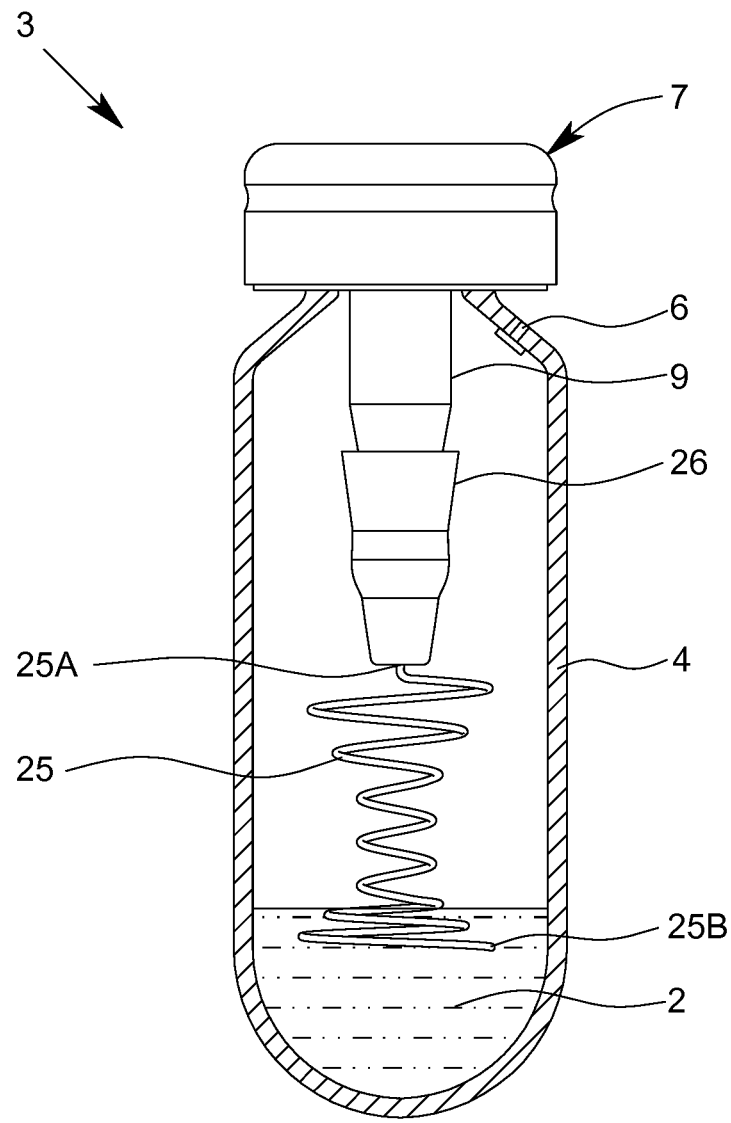
FIG. 16 is a schematic view of a variation of the cartridge according to FIG. 13 with the tube shaped as a double-cone helix.
Figure 17:
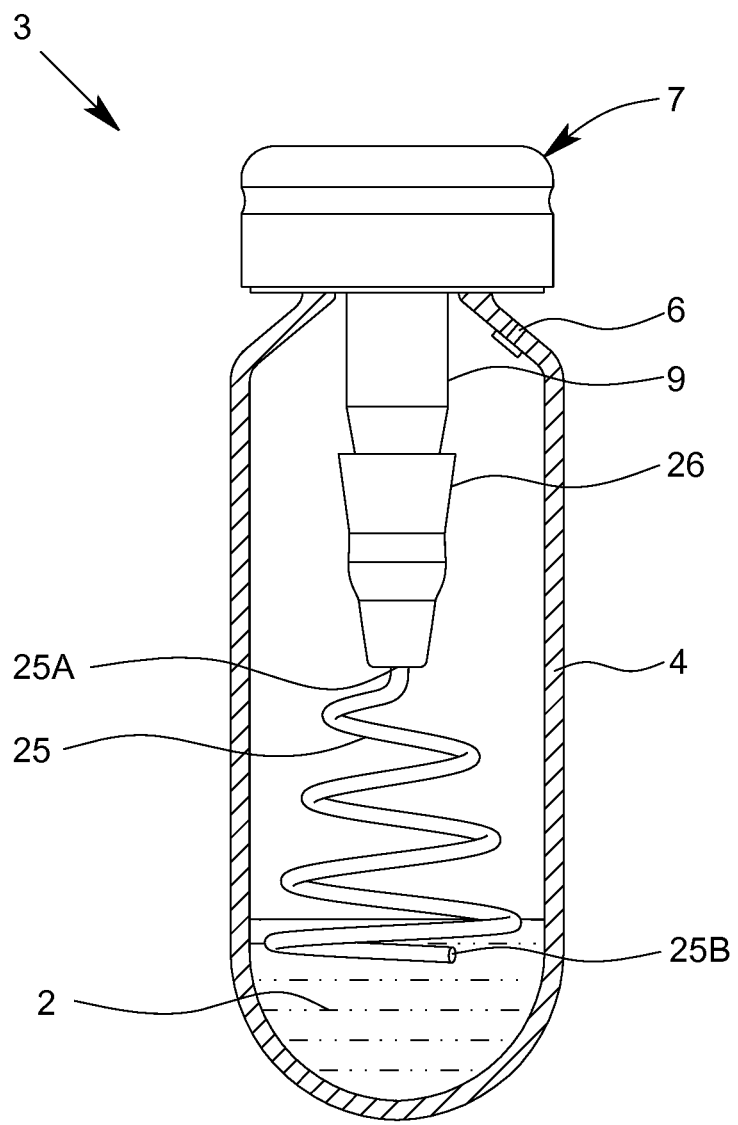
FIG. 17 is a schematic view of another variation of the cartridge according to FIG. 13 with the tube shaped as a conical helix.
Figure 18:
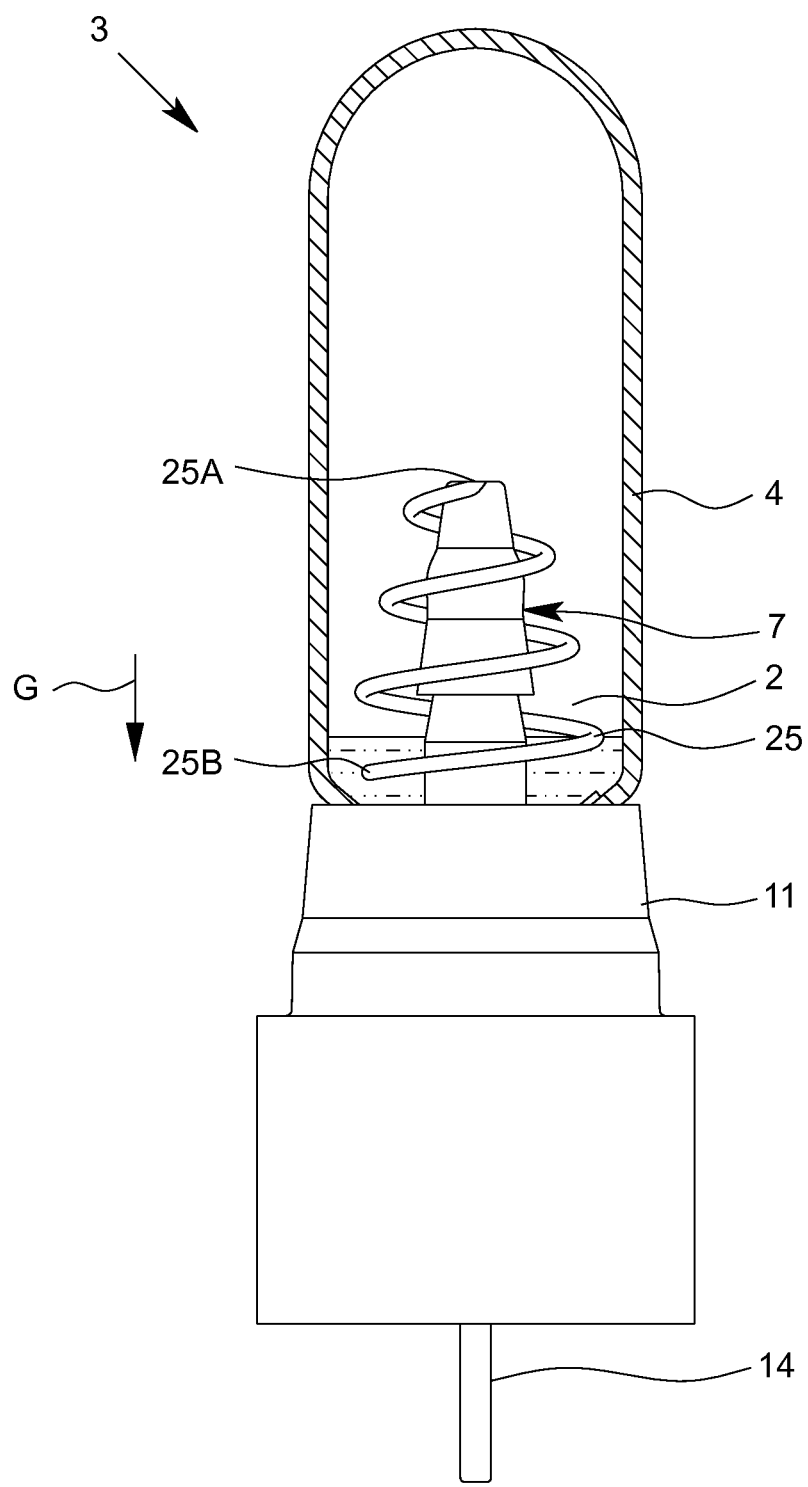
FIG. 18 is a schematic view of the cartridge according to FIG. 17, turned upside down and connected to a partially shown nebulizer.

In the fourth embodiment of the present invention, the tube 25 is preferably shaped at least essentially or partially as a helix, in particular a cylindrical helix as shown in FIGS. 13 to 15 or a conical helix according to FIGS. 17 and 18. However, also other helical shapes of the tube 25 are possible, for example a double-cone shape, which is X-like in a sectional view, where the diameter of the helix first decreases and then increases again, as shown in FIG. 16.

Preferably, the tube 25 has otherwise the same or similar characteristics as the tube 25 described in connection with the previous embodiments, in particular the tube 25 is at least essentially flexible and/or wettable and/or has a constant inner diameter. The tube 25 can also comprise the immersion element 27.

The helix and/or tube 25 is preferably adapted such that the free end 25B is always immersed in the fluid 2, in particular such that the free end 25B is located close to the fluid level.

In particular, the helix is compressible and/or stretchable and/or the height of one complete helix turn, measured parallel to the axis of the helix, also called the pitch of the helix, can change. Thus, the axial length of the helix is adaptable, in particular the helix can be stretched and/or compressed by changing the pitch.

Preferably, the portion of the helix which is immersed in the fluid 2 is at least essentially as much compressed as possible and/or the pitch of the immersed helix portion is at least essentially zero and/or the helix portion immersed in the fluid 2 is at least essentially flat, in particular if no immersion element 27 is provided.

Compression of the immersed helix portion is preferably achieved by the buoyancy force exerted by the fluid 2 onto the portion of the helix or tube 25 immersed in said fluid 2, thus pushing said portion upwards. However, the helix or tube 25 is adapted to not float on the fluid 2, but being (slightly) immersed, such that the free end 25B of the tube 25 is located below, but preferably close to, the fluid level.

Preferably, the pitch of the helix, is at least essentially constant over the length of the helix portion not immersed in the fluid 2. The portion of the helix immersed in the fluid 2 preferably has also a constant pitch which, however, may be different, in particular smaller, than the pitch of the helix portion not immersed in the fluid 2. Thus, preferably, the pitch changes at the fluid level. However, also other solutions are possible with the pitch being constant over the whole length of the helix or with varying pitch over the whole length of the helix, for example with increasing or decreasing pitch from the fixed end 25A to the free end 25B.

Particularly preferably, the axial length of the helix depends on or adjusts to the height of the fluid level and/or filling level of the fluid 2 in the container 4. FIG. 14 shows an example with a higher fluid level and/or more fluid 2 contained in the container 4. In this case, the helix, in particular the helix portion not immersed in the fluid 2, is more compressed and/or the pitch of said helix portion is smaller than for a lower fluid level and/or less fluid 2 in the container 4 as shown in FIG. 13.

When providing an immersion element 27, in particular at or close to the free end 25B, the helix, tube 25 and/or free end 25B is preferably immersed deeper than without an immersion element 27 and/or not located close to the fluid level and/or located closer to the bottom of the container 4 in the upright position. This is shown in FIG. 15.

Deeper immersion of the helix, tube 25 and/or free end 25B is preferably due to the additional weight of the immersion element 27 counteracting the buoyancy force of the fluid 2.

Particularly preferably, the geometry and/or weight of the immersion element 27 is adapted such that a desired immersion depth of the helix, tube 25 and/or free end 25B is achieved. In particular, the immersion depth becomes greater with greater weight and/or smaller volume of the immersion element 27.

Particularly preferably, the tube 25 has the shape of a conical helix, i.e. a helix where the diameter of the helix, measured perpendicularly to the axis of the helix, is constantly decreasing or increasing along said axis. In particular, the inside of the helix is cone-shaped and/or the tube 25 has the shape as if wrapped around a cone. This preferred conical shape of the helix is shown in FIGS. 17 and 18.

Preferably, the conical helix has a smaller number of windings or turns than the cylindrical helix, particularly preferably about half the number of windings or turns.

Preferably, the helix has the smallest diameter at the fixed end 25A and the largest diameter at the free end 25B and/or is tapered from the free end 25B towards the fixed end 25A. However, it is also possible for the helix to be tapered towards the free end 25B and/or to have the smallest diameter at the free end 25B and the largest diameter at the fixed end 25A.

Also other solutions with non-constant diameter are possible here, where the largest and/or smallest diameter is/are neither at the free end 25B nor the fixed end 25A, for example the double-cone shape shown in FIG. 16 which assumes its smallest diameter at least essentially at half the length of the helix or tube 25.

The diameter of the helix at its widest point is preferably at least 5% or 10% smaller than the diameter of the container 4.

The helix or tube 25 is preferably compressible to an at least essentially two-dimensional or flat spiral. This is in particular achieved by the preferred conical shape which allows the helix or tube 25 to become an at least essentially two-dimensional or flat spiral when maximally compressed. In contrast, when the cylindrical helix is maximally compressed, the tube walls hit each other such that the shape remains cylindrical and thus three-dimensional or non-flat.

Preferably, the helix and/or tube 25 is adapted such that the free end 25B is always immersed in the fluid 2, even if the cartridge 3 is not in the upright position.

In particular, the helix or tube 25 is bendable and/or can bend towards the fluid 2, for example in a horizontal position of the cartridge 3 or container 4, as explained for the previous embodiments.

Additionally, the compressibility of the helix or tube 25 allows the helix or tube 25 to adapt its length such that the free end 25B remains immersed in the fluid 2. This preferably prevents the helix or tube 25 to get stuck at the wall of the container 4 or bag 5 and/or is conducive to keep the free end 25B immersed in the fluid 2 in a tilted position of the cartridge 3 or container 4.

The helix or tube 25 is preferably adapted such that its windings do not get stuck with each other when the cartridge 3 or container 4 is in a tilted position and/or when the helix or tube 25 is bent. In particular, for a helical shape having the largest diameter at or close to the free end 25B, such as the preferred conical shape, the free end 25B can more easily adapt to the position or level of the fluid 2. This is preferably due to the free end 25B having a distance to other parts of the tube 25 such that getting stuck, for example in the next winding of the helix, is prevented.

Particularly preferably, the helix is compressible and/or reversible due to gravity G and/or wettability of the tube 25 when the cartridge 3 is in an at least essentially upside down position. This is shown in FIG. 18 for the preferred conical shape.

For a non-conical shape, when turned upside down, the helix or tube 25 becomes or is maximally compressed and/or the pitch of the helix is as small as possible, in particular at least essentially zero (not shown).

For the preferred conical shape, as shown in FIG. 18, when turned upside down, the helix or tube 25 reverses or is reversed and/or the tube 25 has a helical shape but into the opposite direction, spiraling or extending from the fixed end 25A towards closure 7 or the top of the cartridge 3 or container 4. In this case, the pitch of the helix can differ from the pitch in the upright position, but can also be the same.

Preferably, in the upside down position, the helix and/or tube 25 spirals around the connection port 9 and/or adapter 26.

In the upside down position, the free end 25B is preferably located close to the top or upper axial end or closure 7 of the cartridge 3. In this way, it is ensured that the free end 25B always remains immersed in the fluid 2.

Preferably, the helix or tube 25 reverses or is reversed, at least partly, also in positions of the cartridge 3 between the horizontal and upside down position. This ensures that the free end 25B remains immersed in the fluid 2 also in these positions.

Generally, the free end 25B of the tube 25 may form always at least essentially the lowest point of the tube 25 independent from the orientation of the cartridge 3.

Figure 19:
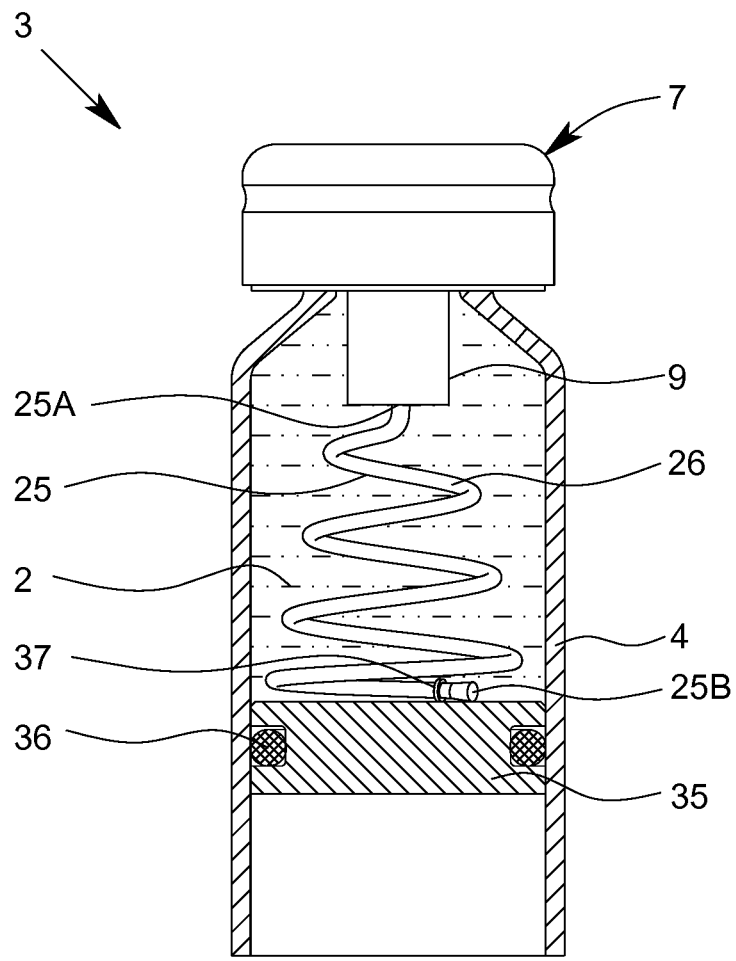
FIG. 19 is a schematic view of a cartridge according to a fifth embodiment of the invention.

FIG. 19 shows the cartridge 3 according to a fifth embodiment of the present invention.

According to the fifth embodiment, the cartridge 3 preferably comprises a moveable element or piston 35. In particular, the piston 35 is moveable axially and/or within the container 4.

According to the fifth embodiment, the container 4 preferably has an opening at its bottom or lower axial end, which is closed off by the piston 35.

In particular, in the delivery state and/or before any fluid 2 has been withdrawn from the cartridge 3 or container 4, the piston 35 is in an initial (lower) position. Preferably, in the initial position the piston 35 is located adjacent to or at the base or axial end of the container 4 opposite to the closure 7. The volume delimited by the container 4, closure 7 and piston 35 in the initial position preferably is or defines the maximum filling volume of the container 4.

Preferably, the container 4 or piston 35 is provided with a piston seal 36 acting between the piston 35 and the inner wall of container 4, in particular to seal the piston 35 against the interior of the container 4 in a liquid- and/or gas-tight manner. The piston seal 36 can be formed as a ring or lip and/or held by the piston 35. However, other constructional solutions are possible as well.

When withdrawing fluid 2, the piston 35 preferably moves axially towards the closure 7, in the representation of FIG. 19 upwards. In particular, FIG. 19 shows the cartridge 3 in a state where some fluid 2 has already been withdrawn from the cartridge 3 and/or where the piston 35 has already moved upwards.

Preferably, the cartridge 3 according to the fifth embodiment does not comprise or require an aeration/ventilation 6. In this case, withdrawing fluid 2 from the cartridge 3 creates a low pressure within the container 4 and, thus, a pressure difference between the inside and the outside of the container 4. This pressure difference preferably causes the piston 35 to move, in particular such that the volume delimited by closure 7, container 4 and piston 35 decreases. Hence, the piston 35 preferably moves towards the closure 7 until a pressure compensation of the pressure inside and outside of the container 4 is reached.

In particular, the piston 35 assumes a new axial position within the container 4 and remains in this new axial position until further fluid 2 is withdrawn.

Preferably, the connection port 9 and/or adapter 26 does not extend far into the interior of the container 4, such that the piston 35 can move at least essentially all the way to the closure 7 and/or at least essentially over the whole length of the container 4. In particular, the volume delimited by closure 7, container 4 and piston 35 can be decreased to at least essentially zero, such that nearly all fluid 2 can be withdrawn from cartridge 3.

Particularly preferably, the cartridge 3 according to the fifth embodiment further comprises a tube 25. In particular, the fixed end 25A of the tube 25 is located close to the top or upper axial end of the container 4, accordingly with the connection port 9 and/or adapter 26 not extending far into the interior of the container 4.

The free end 25B of the tube 25 is preferably fixed or attached to the piston 35. In particular, the tube 25 is fastened to the piston 35 by a fastener 37, for example a bracket or clamp, at or close to the free end 25B. However, also other solutions are possible, for example bonding tube 25 to the piston 35.

Preferably, the tube 25 is funnel-or cone-shaped at or close to its free end 25B. In particular, the outer diameter of tube 25 might increase towards the free end 25B.

The fastener 37 is preferably located at a portion of the tube 25 with constant outer diameter. In this way, the free end 25B with larger outer diameter cannot detach from the fastener 37, such that the tube 25 is attached to piston 35 with the fastener 37 in a form-fit manner.

Preferably, the tube 25 is attached to the piston 35 such that the free end 25B is at least essentially parallel and/or close to the surface of the piston 35 facing closure 7.

In particular, the free end 25B is always located at and/or fluid 2 is always withdrawn from the bottom or lower axial end of the volume containing the fluid 2. This is in particular advantageous when fluid 2 is withdrawn from cartridge 3 in the upright position.

Particularly preferably the tube 25 has a helical shape as described in connection with the fourth embodiment, especially preferably the shape of a conical helix.

As already explained in connection with the fourth embodiment, the helix is preferably compressible, wherein the conical helix can particularly preferably become or form an at least essentially flat or two-dimensional spiral, when maximally compressed.

Compressibility of the helix or tube 25 is especially beneficial in connection with the moveable piston 35. When the piston 35 moves towards closure 7 the helix or tube 25 is preferably more and more compressed. Hence, the axial length of the helix or tube 25 is adjustable or adjusts, in particular by itself, to the distance of the closure 7 and the piston 35 and/or to the axial length of the volume containing the fluid 2. This ensures that the piston 35 can move within container 4 without being blocked or hindered by the tube 25 before reaching an end position.

The piston 35 preferably assumes its end position when the helix or tube 25 is maximally compressed. Further movement of the piston 35 is then blocked by the helix or tube 25 and/or no more fluid 2 can be withdrawn from container 4. In this regard the conical helix is especially advantageous, as it becomes an at least essentially flat spiral when maximally compressed, thus taking up minimal axial space within the container 4. Thus, in a cartridge 3 with a conical helix, the piston 35 can move at least essentially along the whole axial length of container 4 and/or at least essentially all fluid 2 can be withdrawn from cartridge 3.

Figure 20:
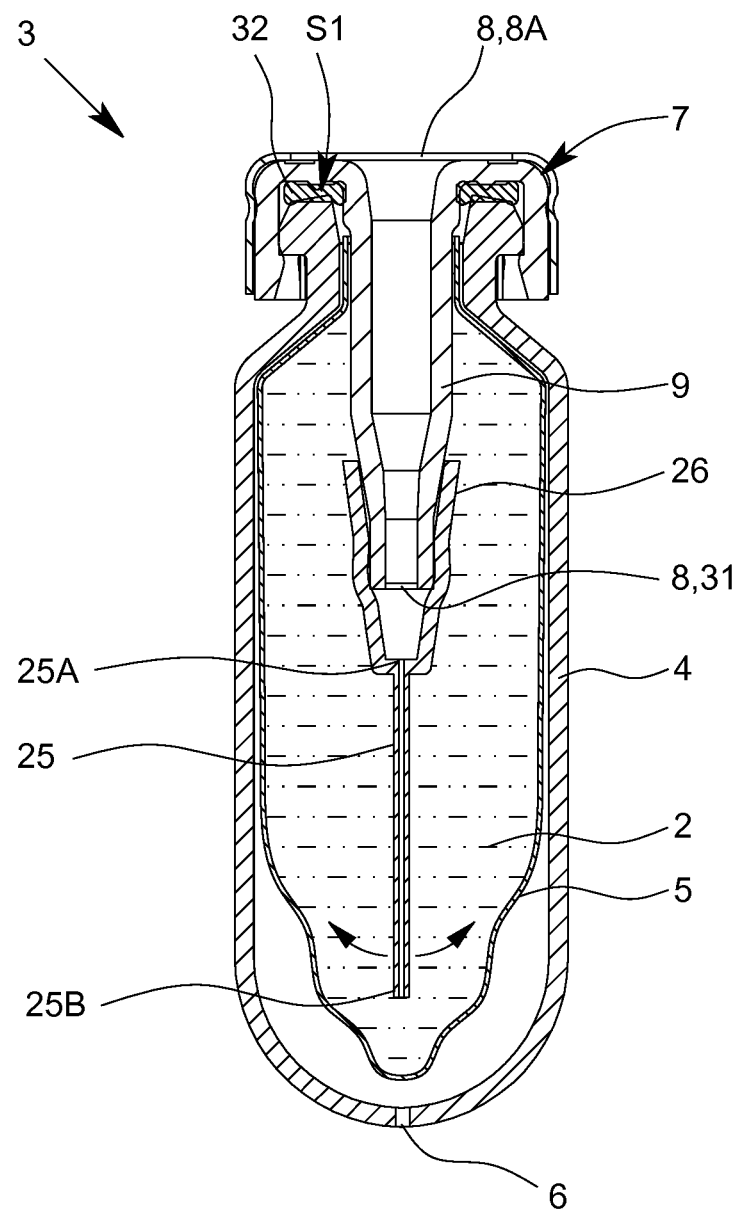
FIG. 20 is a schematic section of a cartridge according to a sixth embodiment of the invention.

FIG. 20 shows the cartridge 3 according to a sixth embodiment of the present invention.

According to the sixth embodiment, the cartridge 3 comprises a preferably flexible/collapsible bag 5 containing the fluid 2, preferably wherein the bag 5 is arranged or held within the container 4, as described in connection with FIGS. 1 and 2, and further comprises a flexible/bendable tube 25.

Preferably, the ventilation/aeration 6 is arranged at the bottom or lower axial end of the container 4. In this way it is preferably ensured that the collapsible bag 5 detaches from the container 4 starting at said lower axial end and/or collapses starting from said lower axial end. In particular, the ventilation/aeration 6 in this case is an indirect gas connection. Thus, no sterile filter is necessary, although it is possible to provide such filter in addition.

The tube 25, in particular its free end 25B, preferably does not comprise an immersion element 27. This preferably increases the movability of the tube 25 and/or prevents or reduces that the tube 25 gets stuck or jammed, in particular in folds of the bag 5. However, it is also possible to provide the tube 25 with an immersion element 27, particularly preferably with an encompassing immersion element 27 as described in connection with FIG. 10.

Preferably, the bag 5 is less wettable than the tube 25 and/or comprises an at least partially hydrophobic and/or non-polar (inner) surface. In this case, the bag 5, in particular its (inner) surface, might be coated with a hydrophobic and/or non-polar material and/or be made of a hydrophobic and/or non-polar material. In this way, the wettability of the bag 5 is decreased so that optionally less fluid 2 might stick to the (inner) surface of bag 5. Thus, in a synergetic manner, a hydrophilic and/or polar tube 25 and a hydrophobic and/or non-polar bag 5 facilitate to increase the volume of fluid 2 that can be withdrawn from the cartridge 3.

For example, the bag 5 might be made of or coated with polytetrafluoroethylene, waxes, like paraffin wax, or the like.

Preferably, the contact angle between a drop of fluid 2 and the surface of the bag 5 is larger than 70° or 90°, in particular larger than 100° or 110°, particularly preferred larger than 130° or 140°.

FIGS. 21 to 23 show the cartridge 3 according to a seventh embodiment of the present invention. FIG. 21 shows the cartridge 3 before being connected to the delivery mechanism 10 and/or with closed or intact seal 8, foil 8A and/or membrane or sealing wall 31. FIG. 22 shows the cartridge 3 when connected to the delivery mechanism 10 and/or with opened or pierced seal 8, foil 8A and/or membrane or sealing wall 31. FIG. 23 is a schematic detail of the membrane or sealing wall 31 in the closed or intact state.

Features described in connection with the seventh embodiment which are not directly related to the tube 25, such as features of the membrane or sealing wall 31, radial sealing of the connecting element 14, or the like, can preferably also be implemented independently from the tube 25. In this case, the connecting element 14, when connected to the cartridge 3, is immersed in the fluid 2, as shown in FIGS. 1 and 2.

Regarding features of the tube 25, in particular its connection with the connecting element 14, the seventh embodiment is similar to the second embodiment as shown in FIGS. 8 and 9. Hence, only relevant differences or additional aspects will be emphasized. The previous explanations, in particular in connection with the second embodiment, apply preferably in addition or in a similar manner and lead to similar features and advantages even if not repeated. However, also other explanations, features and advantages of the other embodiments may be realized, such as wettability of the tube 25, its shape, etc.

According to the seventh embodiment of the present invention, the intermediate piece 29 is preferably formed integrally with the tube 25. In particular, the fixed end 25A comprises or forms the intermediate piece 29.

The fixed end 25A or intermediate piece 29 preferably comprises a contact surface 29B for the connecting element 14, being arranged on the side facing away from tube 25 and/or towards the top of the cartridge 3.

Preferably, the intermediate piece 29 or fixed end 25A is axially moveable relative to and/or within the closure 7, connection port 9 and/or adapter 26. The fixed end 25A is preferably only fixed with respect to radial movement, at least initially or in the delivery state. The delivery state is to be understood as the state before the cartridge 3 is connected to or inserted into the nebulizer 1.

After the cartridge 3 has been connected to the delivery mechanism 10 of the nebulizer 1, the fixed end 25A is preferably also fixed with respect to axial movement.

In particular, according to the seventh embodiment, the adapter 26 and tube 25 are preferably formed as two separate parts such that the whole tube 25, together with the intermediate piece 29 integrally formed therewith, is preferably axially movable with respect to the closure 7, connection port 9 and/or adapter 26.

The intermediate piece 29, fixed end 25A and/or tube 25 is preferably adapted to compensate length tolerances of connecting element 14.

In the delivery state or before the cartridge 3 is connected to the delivery mechanism 10 of the nebulizer 1, the intermediate piece 29, fixed end 25A and/or tube 25 is preferably arranged in the adapter 26 or connection port 9 in an initial position which allows to push the intermediate piece 29, fixed end 25A and/or tube 25 further downwards in the axial direction.

Preferably, the intermediate piece 29, fixed end 25A and/or tube 25 is held in said initial position by (radial) force-fit.

Preferably the intermediate piece 29 or fixed end 25A comprises a stop 29A, in particular on the side facing towards the tube 25 and/or away from the top of the cartridge 3. The connection port 9 or adapter 26 preferably has a corresponding bearing surface 26B, limiting axial movement when the stop 29A hits the bearing surface 26B.

When the connecting element 14 is inserted and/or when the cartridge 3 is connected to the delivery mechanism 10 of the nebulizer 1, the connecting element 14 preferably hits the intermediate piece 29 or fixed end 25A, in particular its contact surface 29B, and/or pushes or moves the intermediate piece 29, fixed end 25A and/or tube 25 (further) down in the axial direction (i.e. towards the inside of the cartridge 3), depending on the axial length of the connecting element 14.

In this way, it is preferably possible to compensate for length variations of the connecting element 14.

FIG. 22 shows the case where the tube 25 has been pushed or moved maximally and/or where the stop 29A has hit the bearing surface 26B. However, also cases are possible where the tube 25 is pushed/moved downwards only partly or not at all, in particular when the connecting element 14 is shorter as in the example shown in FIG. 22.

The main difference of the second and seventh embodiment with regard to the compensation of length tolerances of the connecting element 14 is that in the second embodiment the intermediate piece 29 is formed as a separate part which can be plugged into the tube 25 or the like, while in the seventh embodiment the intermediate piece 29 is integrally formed with the tube 25, in particular its fixed end 25A. Thus, in the seventh embodiment the intermediate piece 29 is preferably not pushed/moved relative to the tube 25, but the whole tube 25, together with the intermediate piece 29 is pushed/moved relative to the connection port 9 or adapter 26.

Otherwise, features and advantages described in connection with the second embodiment are equally applicable to the seventh embodiment. Particularly preferably, features described in connection with the second embodiment regarding the connecting element 14 and tube 25 forming or comprising a continuous capillary and/or an at least essentially constant flow area also apply to the cartridge 3 according to the seventh embodiment. In particular, empty spaces or gaps at the transition of the connecting element 14 to the tube 25 or intermediate piece 29 are minimized, thus preventing capillary stops.

The following explanations, features and advantages can preferably also be implemented independently from the tube 25, i.e. they also apply to the cartridge 3 not having tube 25, where the connecting element 14 is immersed in the fluid 2 as shown in FIGS. 1 and 2. Accordingly, the length of the connecting element 14 is preferably greater than in the cases where a tube 25 is provided in addition.

Preferably, the cartridge 3 comprises a sealing S1 between the closure 7 and the container 4 and/or bag 5. In FIGS. 1 to 10, this sealing S1 is shown as a sealing element 32 in the form of a sealing ring or the like, which in particular seals the cartridge 3 in the axial direction.

According to the seventh embodiment of the present invention, as shown in FIGS. 21 and 22, preferably such sealing element 32 is arranged between closure 7 and container 4 and/or bag 5 extending axially into container 4 and can optionally also protrude radially over the edge of an opening of the container 4. In particular, the sealing element 32 is held or fixed between closure 7, in particular connection port 9, and container 4 by radial and/or axial press/tight-fit. Particularly preferably, a gas- and/or liquid tight connection or sealing S5 is formed between the sealing element 32 and the container 4, in particular radially and/or axially.

Preferably, the sealing element 32 is funnel- and/or cone-shaped and/or attached to the connection port 9. In particular, the sealing element 32 is flexible and/or adapted to sealingly receive the connection port 9 and/or connecting element 14, in particular its axial end, mostly preferred in a press/tight fit manner. Particularly preferably, a sealing S4 is formed between the connection port 9 and the sealing element 32.

Preferably, the closure 7 comprises the sealing element 32.

The sealing element 32 is preferably made of rubber, in particular nitrile rubber, butadiene rubber, styrene-butadiene rubber, isoprene rubber, styrene-isoprene rubber, butyl rubber, ethylene propylene diene monomer rubber, or the like, and/or (flexible) plastic, in particular thermoplastics and/or thermoplastic elastomers, such as polyamide, polyethylene, polypropylene, polyurethane, polybutylene terephthalate or polyether block amide or the like. Other suitable materials might be used as well.

Preferably, the cartridge 3, in particular connection port 9 and/or sealing element 32, are/is adapted to sealingly receive the connecting element 14, preferably its axial end and/or the outer edge thereof, in particular in a press/tight fit manner and/or such that a fluidic and/or tight connection between cartridge 3 and the delivery mechanism 10 can be established.

In particular, the cartridge 3 has or forms a preferably cylindrical insertion opening for the connecting element 14 with an at least essentially constant diameter, which preferably corresponds to the diameter of connecting element 14. Preferably, said opening is formed by closure 7, connection port 9 and/or sealing element 32. Said opening can be covered or closed initially, in particular by seal(s) 8, such as foil 8A and/or membrane or sealing wall 31, the seal(s) 8 being adapted to be broken or pierced by the connecting element 14 upon insertion.

Preferably, the connection port 9 and/or the sealing element 32 are/is flexible and/or stretchable.

In particular, the connecting element 14—once inserted—and the connection port 9 are connected in a press fit manner.

Mostly preferred, the (flexible) connection port 9 is (laterally) expanded by the connecting element 14, in particular such that a liquid- and/or gas-tight connection or sealing S2 is formed between the connection port 9 and the connecting element 14.

Additionally or as an alternative, the connecting element 14—once inserted—and the sealing element 32 are connected sealingly and/or in a press fit manner. In particular the (flexible) sealing element 32 is (laterally) expanded by the connecting element 14, preferably its axial end and/or the outer edge thereof, in particular such that a liquid- and/or gas-tight connection or sealing S3 is formed between the connecting element 14, preferably its axial end and/or the outer edge thereof, and the sealing element 32.

Preferably, the connecting element 14 or its axial end has to pass through the connection port 9, in particular also break or pierce the membrane or sealing wall 31 if provided, before being sealingly received by the sealing element 32 and/or forming sealing S3.

Here, both the connection port 9 and the sealing element 32 are connected sealingly and/or in press fit manner with the connecting element 14. With other words, two sealing locations or sealings S2, S3 are established with the connecting element 14: a first one between the lateral side or shell surface of connecting element 14 and the connection port 9 and a second one between the axial end of the connecting element 14 and the sealing element 32.

Preferably, in this case, when being inserted or received, the connecting element 14 first forms or establishes the sealing S2 with the connection port 9 and after passing through the connection port 9 forms or establishes the sealing S3 with the sealing element 32.

Particularly preferably, the connecting element 14 is sealed radially by or sealingly connected with the sealing element 32 and/or connection port 9. Such (radial) sealings S2, S3 between connecting element 14 and connection port 9 or sealing element 32, respectively, are shown in FIG. 22. In particular, the sealings S2 and/or S3 is/are realized or formed by press/tight-fit of the connecting element 14 with the connection port 9 and/or sealing element 32.

In particular, the connection port 9 and/or sealing element 32 is/are flexible, deformable and/or stretchable, at least in part, and has/have a portion or portions with a diameter smaller than the outer diameter of the connecting element 14. Upon insertion of the connecting element 14, said portion(s) can flex/deform/stretch such that the sealings S2 and/or S3 is/are formed between the connecting element 14 and the connection port 9 and/or sealing element 32, respectively, at said portion(s). Alternatively or additionally, the connecting element 14 can be (radially) flexible or deformable.

Particularly preferably, the connecting element 14, when inserted, stretches/deforms the connection port 9 and/or sealing element 32 such that the force exerted on the sealing element 32 and/or the press/tight-fit of connection port 9, sealing element 32 and/or container 4 is further increased.

Preferably, the sealing S2 between the connecting element 14 and the connection port 9 and/or the sealing S3 between the connecting element 14 and the sealing element 32 can be established, even when moving the connecting element 14 axially, as the connecting element 14 is laterally/radially sealingly received by and/or connected with the connection port 9 and/or sealing element 32. In this way, sealings S2, S3 are also provided during insertion of the connecting element 14 and/or while connecting the cartridge 3 to the delivery mechanism 10 of the nebulizer 1, in particular such that fluid 2 can only exit the cartridge 3 via the connecting element 9.

The sealing S2 is preferably formed or established in the connection port 9 at least essentially at the level where the membrane or sealing wall 31 is located in the delivery state. In other words, the sealing formed by the membrane or sealing wall 31 is preferably replaced by the sealing S2 when the connecting element 14 is inserted into the connection port 9.

FIG. 22 shows a further sealing S6 which is preferably formed or established after insertion of the cartridge 3 into the nebulizer 1. In particular, the sealing S6 is located above sealing S2, if provided, and/or close to the top of the closure 7. The sealing S6 can be formed between closure 7/connection port 9 and the connecting element 14, or, as shown in FIG. 22, between closure 7/connection port 9 and a part of the holder 11 of the nebulizer 1.

The sealing element 32 preferably forms or comprises the adapter 26 in the case of the cartridge 3 comprising the tube 25. In particular, explanations, features and advantages described in the various embodiments in connection with adapter 26 and in connection with sealing element 32 are mutually applicable if a tube 25 is provided.

Preferably, the connecting element 14 is (further) sealingly connected to the tube 25, in particular the fixed end 25A or intermediate piece 29 at its axial end as described in connection with the second embodiment. However, such sealing can also be omitted if sealings S2 and/or S3 are provided.

Preferably, the connection port 9 and adapter 26/sealing element 32 are connected with each other by press/tight-fit, in particular forming a sealing S4 in between them. However, also other solutions are possible here, for example the connection port 9 and adapter 26/sealing element 32 being formed integrally or as one piece. Alternatively, the adapter 26/sealing element 32 can be connected with or hold by the container 4, with the connection port 9 resting on or in the adapter 26/sealing element 32.

Particularly preferably, the connection port 9 and adapter 26/sealing element 32 are connected or assembled, in particular by press/tight-fit, before being mounted on the container 4.

The tube 25 can be integrated in and/or form a unit with the connection port 9 or adapter 26/sealing element 32 when mounted on the container 4. Alternatively, the connection port 9 and/or adapter 26/sealing element 32 is first mounted on the container 4 and the tube 25 is subsequently inserted into the container 4, in particular from the top.

In the following, the membrane or sealing wall 31 which is preferably comprised in the cartridge 3 is discussed in further detail.

The membrane or sealing wall 31 is preferably embodied as a diaphragm or septum. Preferably, the membrane or sealing wall 31 is integrated in and/or arranged within the closure 7 or connection port 9, particularly preferably at an end face of the closure 7 or connection port 9 facing towards the adapter 26/sealing element 32 or tube 25 and/or facing away from the top of the cartridge 3.

Alternatively, the membrane or sealing wall 31 can also be integrated in, arranged within and/or connected to the adapter 26/sealing element 32. It is also possible to provide more than one membrane sealing wall 31, for example one arranged in the connection port 9 and one in the adapter 26/sealing element 32.

In the following description the membrane or sealing wall 31 is assumed to be arranged in the connection port 9. However, for the person skilled in the art it is readily apparent that the described features can be similarly realized when the membrane or sealing wall 31 is arranged in the adapter 26/sealing element 32.

The membrane or sealing wall 31 preferably forms a seal 8, in particular sealing the closure 7 or connection port 9 from the fluid 2 contained in the container 4.

The shape of the membrane or sealing wall 31 preferably corresponds to the connecting element 14, in particular the membrane or sealing wall 31 being at least essentially circular or disc-like and/or having at least essentially a diameter equal to the outer diameter of the connecting element 14.

In the delivery state, the membrane or sealing wall 31 is preferably integrally formed or formed as one piece with the closure 7 or connection port 9. Particularly preferably, the closure 7 or connection port 9 and the membrane or sealing wall 31 are injection-molded as one piece.

Preferably, the membrane or sealing wall 31 comprises a central or raised portion 31A, a circumferential portion 31B, a connecting portion 31C and/or a film hinge 31D. The membrane or sealing wall 31 and/or the different portions 31A to 31D of the membrane or sealing wall 31 are preferably formed as one piece, in particular being injection-molded.

The central or raised portion 31A is preferably arranged in the center of the membrane or sealing wall 31 and/or embodied as a thickened portion of the membrane or sealing wall 31. The raised portion 31A is preferably formed as a dome or spherical segment. In particular, the central or raised portion 31A is arranged on the side of the membrane or sealing wall 31 facing the tube 25 and/or facing away from the top of the cartridge 3.

Particularly preferably, the membrane or sealing wall 31 is at least essentially flat on the side facing the top of the cartridge 3 and/or curved or bulged on the opposite side, in particular due to providing the raised portion 31A on said side.

The circumferential portion 31B preferably connects the membrane or sealing wall 31 with the connection port 9 in the delivery state. In particular, the circumferential portion 31B forms a ring or a section of a ring which integrally connects the membrane or sealing wall 31 with the connection port 9 in the delivery state.

The circumferential portion 31B is preferably arranged along the circumference of the membrane or sealing wall 31, at least in part. In particular, only the section of the circumference of the membrane or sealing wall 31 which comprises the connecting portion 31C and/or film hinge 31D does not comprise the circumferential portion 31B.

The circumferential portion 31B preferably is embodied very thin and/or forms a predetermined breaking point of the membrane or sealing wall 31.

Preferably, the thickness of the circumferential portion 31B is less than 0.1 mm or 0.05 mm.

The connecting portion 31C is preferably formed web-like or formed as a ridge or reinforcing rib. In particular, the connecting portion 31C extends from the center of the membrane or sealing wall 31 and/or the raised portion 31A to the connection port 9. Particularly preferably, the connecting portion 31C forms a bridge or additional connection from the connection port 9 to the center of the membrane or sealing wall 31 or raised portion 31A.

In particular, the membrane or sealing wall 31 is (integrally) connected to the connection port 9 via the connecting portion 31C, preferably in addition to being (integrally) connected via the circumferential portion 31B.

The connecting portion 31C is preferably integrally formed with the raised portion 31A, membrane or sealing wall 31 and/or connection port 9.

Particularly preferably, the connecting portion 31C and/or raised portion 31A is ten times or twenty times thicker than the circumferential portion 31B.

When manufacturing the connection port 9 and/or membrane or sealing wall 31, in particular by injection-molding, the connecting portion 31C preferably forms a bridge or additional connection from the connection port 9 towards the center of the membrane or sealing wall 31. The connecting portion 31C preferably bridges the circumferential portion 31B, in particular such that molded material, in particular molded plastic, can be injected or can flow via the connecting portion 31C into the center of the membrane or sealing wall 31, thus forming the central or raised portion 31A. In particular, the material can cross the circumferential portion 31B via the connecting portion 31C.

This ensures that the circumferential portion 31B can be formed as thin as desired, since no material needs to be injected or flow through the circumferential portion 31B during the injection molding process.

The membrane or sealing wall 31 or connecting portion 31C preferably forms or comprises a film hinge 31D. In particular, the membrane or sealing wall 31 can swing or hinge away by means of said film hinge 31D.

When the cartridge 3 is connected to the delivery mechanism 10 of the nebulizer 1, the connecting element 14 is preferably inserted into the connection port 9, in particular from the top of the cartridge 3.

The connecting element 14 is preferably adapted to break or pierce through the membrane or sealing wall 31.

Preferably, the closure 7 or connection port 9 comprises an opening for inserting the connecting element 14. The opening preferably has a funnel-shaped or tapered portion which aligns or guides the connecting element 14 to the membrane or sealing wall 31. In particular, the connecting element 14 is positioned and/or constructed such that it can pierce or break the membrane or sealing wall 31 in a defined or precise manner.

When the connecting element 14 is pushed onto the membrane or sealing wall 31 and/or inserted into the connection port 9, the membrane or sealing wall 31 preferably breaks or tears along the circumferential portion 31B or is adapted thereto.

The central/raised portion 31A, connecting portion 31C and/or film hinge 31D preferably remains intact and/or does not tear or break when the connecting element 14 pushes against the membrane or sealing wall 31 or when the connecting element is inserted into the connection port 9. In particular, the membrane or sealing wall 31 remains connected with the connection port 9 via the film hinge 31D during and after insertion of the connecting element 14 into connection port 9.

The membrane or sealing wall 31 preferably swings, hinges or tilts aside when the connecting element 14 is pushed against the membrane or sealing wall 31 or during connection of the cartridge 3 to the delivery mechanism 10 or is adapted thereto.

Particularly preferably, the membrane or sealing wall 31 swings, tilts or hinges into a pocket 9A formed by the connection port 9 or adapter 26/sealing element 32. Preferably, after connecting the cartridge 3 to the delivery mechanism 10 or in the operational state of the nebulizer 1, the membrane or sealing wall 31 remains tilted aside and/or inside pocket 9A, as shown in FIG. 22.

Particularly preferably, the membrane or sealing wall 31 is arranged in the connection port 9 and/or adapter 26/sealing element 32 so as to be inclined with respect to the longitudinal axis of the connection port 9, adapter 26/sealing element 32 or connecting element 14. In particular, said longitudinal axis has a non-rectangular angle with or is not orthogonal to the main plane of extension of the membrane or sealing wall 31. In particular, the main plane of extension of the membrane or sealing wall 31 is not horizontal in the upright position of the cartridge 3.

Preferably, the membrane or sealing wall 31 is inclined such that the film hinge 31D is located at least essentially at the lowermost point of the membrane or sealing wall 31 in the upright position of the cartridge 3. In particular, the film hinge 31D is the point of the membrane or sealing wall 31 closest to the tube 25 and/or point furthest away from the top of the cartridge 3 or closure 7.

Upon insertion of the connecting element 14 into the cartridge 3, the connecting element 14 preferably first touches or pushes against the point of the membrane or sealing wall 31 which is at least essentially opposite of the film hinge 31D. This is in particular due to the inclined arrangement of the membrane or sealing wall 31, with said point opposite of the film hinge 31D being the uppermost point of the membrane or sealing wall 31 and/or being the point closest to the top of the cartridge 3 or closure 7.

Preferably, the membrane or sealing wall 31 or circumferential portion 31B starts to tear or break at said uppermost point or point opposite of the film hinge 31D. In particular, said point or the circumferential portion 31B in the vicinity of that point can be formed so as to be the thinnest portion of the membrane or sealing wall 31.

When pushing the connecting element 14 further down, the membrane or sealing wall 31 preferably further tears along the whole circumferential portion 31B and hinges away, preferably while still being connected to the connection port 9 via the film hinge 31D.

The membrane or sealing wall 31 preferably tears along the circumferential portion 31B and tilts aside in a defined manner and/or in a manner reproducible for similarly manufactured cartridges 3 or is adapted thereto. In particular, the force required to break the membrane or sealing wall 31 is at least essentially the same for similarly manufactured cartridges 3.

This preferably ensures that the membrane or sealing wall 31, when the cartridge 3 is connected to the delivery mechanism 10, does not block or affect the connecting element 14, fixed end 25A of the tube 25 and/or the delivery mechanism 10. In particular, the membrane or sealing wall does not tear completely and/or remains connected with the connection port 9 via the film hinge 31D and/or is kept in the pocket 9A.

The connection port 9, in particular its end face, can further comprise a step or cut-out 9B located adjacent to the film hinge 31D, as in particular shown in FIG. 23. The cut-out 9B can form the pocket 9A or a part thereof. In particular, the cut-out 9B makes it possible or easier for the membrane or sealing wall 31 to tilt or hinge aside.

The cartridge 3 according to the seventh embodiment of the present invention preferably further comprises a housing 33. The housing 33 preferably covers the container 4 and/or closure 7. In particular, the container 4 and/or closure 7 are arranged within the housing 33.

Preferably, the housing 33 has an opening at the top, in particular for inserting the connecting element 14 into the cartridge 3. In the delivery state, the opening is preferably covered by the seal 8, in particular the foil 8A.

The housing 33 preferably comprises an aeration/ventilation 6 (not shown), such as a valve, opening or hole, preferably at the bottom of the cartridge 3.

Preferably, the housing 33 is rigid and/or made of metal, in particular aluminum. However, also other solutions are possible here such as a plastic housing 33.

The housing 33 preferably has a (circumferential) indentation or notch 33A, in particular extending or protruding into a recess formed between the container 4 and closure 7. The notch 33A preferably forms a neck of the cartridge 3.

The holder 11 of the nebulizer 1 preferably comprises engagement portions 11A which correspond to the notch 33A. The engagement portions 11A are preferably flexible and/or are formed as flexible arms. In particular, the engagement portions 11A can engage with the notch 33A when the cartridge 3 is connected to the holder 11 or delivery mechanism 10 of the nebulizer 1. The cartridge 3 is preferably held or fixed in the nebulizer 1 in a force-fit and/or form-fit manner by means of the engagement portions 11A engaging with the notch 33A.

Preferably, the cartridge 3, container 4 and/or bag 5 is/are sealed by the closure 7, in particular by sealing element 32 and/or sealings S1, S4 and S5 between closure 7, connection port 9, adapter 26, sealing element 32 and/or container 4.

In the delivery state, cartridge 3, container 4 and/or bag 5 is/are preferably further sealed by seal(s) 8, in particular foil 8A and/or membrane or sealing wall 31.

When the cartridge 3 is connected to the delivery mechanism 10, the connecting element 14 preferably breaks or pierces said seal(s) 8, and (new) sealings S2 and/or S3 between the connecting element 14 and the closure 7, connection port 9, adapter 26 and/or sealing element 32 are established. Thus, after the cartridge 3 has been connected to the delivery mechanism 10 or in the operational state of the nebulizer 1, the cartridge 3, container 4 and/or bag 5 is/are preferably sealed by sealings S1 to S5.

Preferably, the cartridge 3 comprises a further sealing S7 between the closure 7 and the housing 33. In particular, a gas- and/or liquid tight connection between the closure 7 and housing 33 is formed.

Particularly preferably, the sealing S7 between the closure 7 and the housing 33 is formed by or comprises a sealing member 34.

The sealing S7 or sealing member 34 preferably seals the cartridge 3 in the radial direction.

The sealing member 34 is preferably in the form of a ring, gasket or molded seal. The sealing member 34 is preferably located in a circumferential recess or notch of the closure 7. The closure 7 and sealing member 34 can also be integrally formed, particularly preferably by two-component injection-molding.

The housing 33 can have an protrusion or indentation 33B, protruding towards, abutting and/or pressing on the closure 7 and/or sealing member 34, in particular to provide or increase press/tight-fit between housing 33 and closure 7 and/or sealing member 34, particularly preferably forming the sealing S7 thereby.

The sealing S7 or sealing member 34 preferably seals the cartridge 3 from the environment. Thus, fluid 2 is prevented from escaping the cartridge 3, even if it has escaped the container 4, in particular by escaping through the connection of the container 4 with the closure 7 and/or through the aeration/ventilation 6.

Especially preferably, already escaping of the fluid 2 from the container 4 is prevented, in particular by providing seals or sealings between container 4 and closure 7 as described above. However, the sealing element 34 or sealing S7 is preferably provided in addition, and/or as a fail-safe, such that no fluid 2 can escape the cartridge 3 or housing 33, even if it has escaped the container 4.

Preferably, at least the container 4 and the adapter 26/sealing element 32 are at least essentially resistant against evaporation or diffusion. In particular, sealings formed by the sealing element 32 prevent not only leakage of the fluid 2, but also (long-term) evaporation or diffusion of the fluid 2.

Thus the cartridge 3 is preferably storage-stable and/or can be stored over a longer period of time without substantial loss of fluid 2.

Particularly preferably, also other parts of the cartridge 3, in particular closure 7, connection port 9, housing 33 and/or sealing member 34, are at least essentially resistant against evaporation or diffusion. However, in particular parts which do not come into direct contact with the fluid 2 can be made of materials which are less evaporation/diffusion resistant.

The present invention allows, supports or ensures the withdrawal of fluid 2 from the cartridge 3 in any spatial position of the cartridge 3 and/or even to withdraw a low residual volume of fluid 2, e.g. of less than 0.1 ml, 0.05 ml or 0.01 ml, out of the cartridge 3. Thus, due to the present invention, the total amount of doses that can be dispensed is increased and/or misuse or misapplication of the nebulizer 1 can be prevented or at least the risk of such a misuse or misapplication can be reduced.

Individual features, aspects and/or principles of the different embodiments described can be realized independently from each other and may also be combined with one another in -continued List of reference numerals:

| | |
|---|---|
| S3 | sealing (connecting element - adapter/sealing element) |
| S4 | sealing (connection port - adapter/sealing element) |
| S5 | sealing (container - adapter/sealing element) |
| S6 | sealing (closure - connecting element/holder) |
| S7 | sealing (closure - housing) |

The invention claimed is:

1. A cartridge (3) for a nebulizer (1) for nebulizing of a fluid (2), the fluid (2) being a pharmaceutical composition/formulation and/or a liquid medicament, the cartridge (3) comprising:

a container (4) containing the fluid (2) to be nebulized, a tube (25) disposed within the container (4) for conveying the fluid (2) out of the container (4), and being at least partially flexible and/or bendable, a closure (7) with a connection port (9) cooperating with an opening of the container (4) for fluidically and/or sealingly connecting the container (4) to a nebulizer (1), an adapter (26) mechanically and/or fluidically connecting the tube (25) to the connection port (9) of the closure (7) by sealingly receiving the connection port (9) therein, such that the container (4) is in fluidic communication with a connecting element (14) of the nebulizer (1), and a rigid intermediate piece (29) to fluidically connect the tube (25) to the connecting element (14), wherein the intermediate piece (29) is axially moveably, and axially pushable, into or onto or together with the tube (25) by the connecting element (14) in order to compensate length tolerances of the connecting element (14).

2. The cartridge according to claim 1, wherein the connection port (9) of the closure engages an axial/fixed end (25A) of the tube (25) in a center area of the container (4) such the connection port (9) is fluidically and/or sealingly connected to the tube (25).

3. The cartridge according to claim 1, wherein at least one of:

the tube (25) is constructed as a capillary tube, the tube (25) comprises an inner diameter of less than 1 mm, the tube (25) comprises an inner diameter of less than 0.8 mm, the tube (25) comprises an inner diameter of less than 0.7 mm, the tube (25) comprises an inner diameter of less than 0.5 mm, the tube (25) comprises an inner diameter of more than 0.1 mm, and the tube (25) comprises an inner diameter of more than 0.2 mm.

4. The cartridge according to claim 3, wherein the tube (25) is constructed such that in a delivery state of the cartridge (3) and/or when opening the cartridge (3), the tube (25) is at least partially immersed in the fluid (2) and/or a fluid level within the tube (25) is equal to or above a fluid level outside the tube (25).

5. The cartridge according to claim 1, wherein the tube (25) is at least one of shorter than a height of the container (4) and completely arranged within the container (4), such that a free end (25B) of the tube (25) can reach outermost areas of the container (4), including upper and lower axial ends of the container (4).

6. The cartridge according to claim 1, wherein the tube (25) is made of at least one of: plastic, thermoplastics, thermoplastic elastomers, polyamide, polyethylene, polypropylene, polybutylene terephthalate, and polyether block amide.

7. The cartridge according to claim 1, wherein at least one of:

the tube (25) is surface treated in order to increase its surface energy, the tube (25) is corona treated in order to increase its surface energy, the tube (25) plasma treated in order to increase its surface energy, the tube (25) is flame treated in order to increase its surface energy, and the tube (25) is coated, in order to increase its surface energy.

8. The cartridge according to claim 1, wherein the tube (25) contains at least one additive in order to increase its surface energy.

9. The cartridge according to claim 1, wherein a surface energy of the tube (25) is greater than or equal to a surface tension of the fluid (2).

10. The cartridge according to claim 1, wherein at least one of:

the tube (25) is at least partially wettable with the fluid (2) in such a way that the tube (25) is at least partially immersed in the fluid (2), the tube (25) is wettable with the fluid (2) in such a way that a contact angle between a drop of the fluid (2) and the surface of the tube (25) is less than one of: 70°, 60°, 50°, 30°, and 20°.

11. The cartridge according to claim 10, wherein an inner surface of the container (4) is at least less wettable with the fluid (2) than the tube (25) with the fluid (2).

12. The cartridge according to claim 11, wherein a surface energy of the inner surface of the container (4), is smaller than a surface energy of the tube (25) and/or smaller than a surface tension of the fluid (2).

13. The cartridge according to claim 12, wherein a contact angle between the inner surface of the container (4) and a drop of the fluid (2) is greater than one of: 70°, 90°, 100°, 110°, 130°, 140°, and a contact angle between a surface of the tube (25) and a drop of the fluid (2).

14. The cartridge according to claim 1, wherein the cartridge (3) comprises an immersion element (27) attached to or formed by the tube (25).

15. The cartridge according to claim 14, wherein the immersion element (27) is attached to or formed by a free end (25B) of the tube (25) opposite a fixed end (25A) of the tube (25) at the connection port (9).

16. The cartridge according to claim 15, wherein the immersion element (27) is adapted such that at least the free end (25B) of the tube (25) is kept in the fluid (2).

17. The cartridge according to claim 14, wherein the immersion element (27) has a tube-like or conical shape and encompasses the tube (25) at least in part.

18. The cartridge according to claim 14, wherein a surface energy of the immersion element (27) is greater than or equal to a surface tension of the fluid (2).

19. The cartridge according to claim 1, wherein the tube (25) or an immersion element (27) thereof comprises an at least partially hydrophilic and/or polar surface, and the fluid (2) is aqueous and/or comprises an aqueous solution and/or water as solvent.

20. The cartridge according to claim 1, wherein the container (4) comprises an at least partially hydrophobic and/or non-polar inner surface or layer, and the fluid (2) is aqueous and/or comprises an aqueous solution and/or water as solvent.

21. The cartridge according to claim 1, wherein the fluid (2) contains at least one of: (i) at least one additive, and (ii) benzalkonium chloride, in order to decrease its surface tension.

22. The cartridge according to claim 1, wherein the tube (25) has at least partially a shape of a helix, which is a conical helix and/or is tapered towards a fixed end (25A) of the tube (25) at the connection port (9), opposite a free end (25B) of the tube (25).

23. The cartridge according to claim 22, wherein a largest diameter of the helix at a free end (25B) opposite the fixed end (25A), is at least 5% or 10% smaller than the inner diameter of the container (4).

24. The cartridge according to claim 22, wherein at least one of:
the helix is compressible,
an axial length of the helix is adaptable according to a level of the fluid (2), and
the cartridge (3) comprises a piston (35) which is movable within the container (4), with the free end (25B) of the helix or the tube (25) being attached or fastened to the piston (35).

25. The cartridge according to claim 22, wherein at least one of:
the free end (25B) of the helix or tube (25) is located at or adjacent to a lowest point of the fluid (2) within the fluid (2) in the container (4) for any spatial orientation of the cartridge (3), including when turned upside down, and
the helix or tube (25) is reversible, such that the free end (25B) of the helix or tube (25) is at essentially the lowest point of the helix or tube (25), when turned upside down.

26. The cartridge according to claim 1, wherein a density of the tube (25) and/or of an immersion element (27) thereof is at least one of more than 10%, 25% or 50%, greater than a density of the fluid (2).

27. The cartridge according to claim 1, wherein an axial/fixed end (25A) and/or a free end (25B) of the tube (25) comprises a valve (30) which is designed to open or close automatically depending on a spatial orientation of the valve (30) and/or the free end (25B).

28. The cartridge according to claim 27, wherein the valve (30) is closed when the free end (25B) is not immersed in the fluid (2) and/or points at least essentially into an opposite direction than gravity (G) and is open otherwise.

29. The cartridge according to claim 1, wherein the fluid (2) at least one of: has polar characteristics, is an aqueous pharmaceutical formulation, is an alcoholic pharmaceutical formulation, and is an ethanolic pharmaceutical formulation.

30. The cartridge according to claim 1, wherein at least one of:
the closure (7) or connection port (9) comprises a membrane or sealing wall (31) with a film hinge (31D) and a circumferential portion (31B) of reduced thickness, so that the membrane or sealing wall (31) tears along the circumferential portion (31B) and tilts aside upon insertion of a connecting element (14) of the nebulizer (1), the cartridge (3) comprises a sealing element (32) between the closure (7) and the container (4) for forming a sealing (S1) inbetween, wherein the sealing element (32) is adapted to sealingly receive the connecting element (14) after passing through the connection port (9); and
the membrane or sealing wall (31) is formed as one piece with the closure (7) or connection port (9).

31. The cartridge according to claim 30, wherein the closure (7), connection port (9), adapter (26) and/or sealing element (32) comprise or form a pocket (9A) for receiving the membrane or sealing wall (31) when tilted aside.

32. The cartridge according to claim 30, wherein the membrane or sealing wall (31) comprises a preferably ridge-like connecting portion (31C) of increased thickness, connecting the center of the membrane or sealing wall (31) with the closure (7) or connection port (9).

33. The cartridge according to claim 30, wherein the main plane of extension of the membrane or sealing wall (31) is inclined with respect to the longitudinal axis of the closure (7), connection port (9) and/or connecting element (14) in the closed or unbroken state.

34. The cartridge according to claim 33, wherein the membrane or sealing wall (31) is inclined such that the film hinge (31D) is located at or forms the point farthest A away from an opening, for inserting the connecting element (14), of the cartridge (3), closure (7) and/or connection port (9).

35. The cartridge according to claim 30, wherein the membrane or sealing wall (31) is located between a sealing (S2) formed between the connection port (9) and the connecting element (14) and a sealing (S3) formed between the sealing element (32) and the connecting element (14).

36. The cartridge according to claim 1, wherein the connection port (9) is made of at least one of: rubber, butyl rubber, and flexible plastic.

37. The cartridge according to claim 1, wherein the closure (7) is sterile.

38. The cartridge according to claim 1, wherein the cartridge (3) or the container (4) thereof comprises at least one of: an aeration/ventilation (6), a valve, an opening, a hole, and a sterile filter.

39. The cartridge according to claim 1, wherein the adapter (26) is adapted to sealingly receive the connection port (9) and the connecting element (14) in at least one of: a press/tight fit manner, an axially moveable manner, and a way that a continuous capillary and/or a capillary transition from the tube (25) to the connecting element (14) is formed.

40. The cartridge according to claim 1, wherein at least one of:
the intermediate piece (29) is adapted to form a capillary transition from the tube (25) to the connecting element (14), and
a flow area of an inner diameter of the intermediate piece (29) at least essentially matches a flow area of inner diameters of the tube (25), in order form a continuous capillary and/or a capillary transition from the tube (25) to the connecting element (14).

41. The cartridge according to claim 1, wherein the intermediate piece (29) and the tube (25) are sealingly insertable into each other.

42. The cartridge according to claim 1, wherein the intermediate piece (29) is integrally formed with the tube (25).

43. The cartridge according to claim 1, wherein the tube (25) is made of at least one of: rubber, butyl rubber, plastic, thermoplastics, thermoplastic elastomers, polyamide, polyethylene, polypropylene, polybutylene terephthalate, and polyether block amide.

44. The cartridge according to claim 1, wherein the cartridge comprises a sealing element (32) between the closure (7) an the container (4) for forming a sealing (S1) inbetween, wherein the sealing element (32) is adapted to sealingly receive the connecting element (14) after passing through the connection port.

45. The cartridge according to claim 44, wherein the adapter (26) forms or comprises the sealing element (32) or vice versa.

46. A nebulizer (1) for a fluid (2), comprising:
a cartridge (3) with a container (4) containing the fluid (2),
a housing (20) for receiving the cartridge (3),
a delivery mechanism (10) for pressurizing the fluid (2) after the fluid is withdrawn from the cartridge, and
a connecting element (14) for fluidically connecting the cartridge (3) to the delivery mechanism (10), wherein:
the cartridge (3) comprises a tube (25) disposed within the container (4) for conveying the fluid (2) out of the container (4), and being at least partially flexible and/or bendable,
a closure (7) with a connection port (9) cooperating with an opening of the container (4) for fluidically and/or sealingly connecting the container (4) to the nebulizer (1),
an adapter (26) mechanically and/or fluidically connecting the tube (25) to the connection port (9) of the closure (7) by sealingly receiving the connection port (9) therein, such that the container (4) is in fluidic communication with the connecting element (14) of the nebulizer (1),
the cartridge (3) comprises a rigid intermediate piece (29) to fluidically connect the tube A (25) to the connecting element (14), and wherein
the intermediate piece (29) is axially moveably, and axially pushable, into or onto or together with the tube (25) by the connecting element (14) in order to compensate length tolerances of the connecting element (14).

47. The nebulizer according to claim 46, wherein the cartridge (3) comprises the closure (7) with at least one of a membrane, a sealing wall (31) within the connection port (9), a seal (8), and a foil (8A), which covers the connection port (9) from an exterior.

48. The nebulizer according to claim 47, wherein the connecting element (14) is rigid and/or constructed as a piercing element and/or adapted to pierce and/or open the at least one of the seal (8), the foil (8A), the membrane, and the sealing wall (31).

49. The nebulizer according to claim 47, wherein the closure (7) and/or connection port (9) is adapted to form a sealing (S2) with the connecting element (14).

50. The nebulizer according to claim 46, wherein the adapter (26) is at least one of funnel-shaped or cone-shaped.

51. The nebulizer according to claim 46, wherein at least one of:
the intermediate piece (29) is adapted to form a capillary transition from the tube (25) to the connecting element (14), and
a flow area of an inner diameter of the intermediate piece (29) at least essentially matches a flow area of inner diameters of the tube (25), in order form a continuous capillary and/or a capillary transition from the tube (25) to the connecting element (14).

52. The nebulizer according to claim 46, wherein the intermediate piece (29) and at least one of the tube (25) and the intermediate piece (29), and the connecting element (14) are insertable into each other such that a seal is formed.

53. The nebulizer according to claim 46, wherein the intermediate piece (29) is integrally formed with the tube (25).

54. The nebulizer according to claim 46, wherein the tube (25) is made of at least one of: rubber, butyl rubber, plastic, thermoplastics, thermoplastic elastomers, polyamide, polyethylene, polypropylene, polybutylene terephthalate, and polyether block amide.

55. The nebulizer according to claim 46, wherein the tube (25) is at least one of shorter than a height of the container (4) and completely arranged within the container (4), such that a free end (25B) of the tube (25) can reach outermost areas of the container (4), including upper and lower axial ends of the container (4).

56. The nebulizer according to claim 46, wherein the connection port (9) is made of at least one of: rubber, butyl rubber, and flexible plastic.

57. The nebulizer according to claim 46, wherein the closure (7) or connection port (9) comprises a membrane or sealing wall (31) with a film hinge (31D) and a circumferential portion (31B) of reduced thickness, so that the membrane or sealing wall (31) tears along the circumferential portion (31B) and tilts aside upon insertion of a connecting element (14) of the nebulizer (1).

* * * * *